US010837034B2

(12) United States Patent
Jaitzig et al.

(10) Patent No.: US 10,837,034 B2
(45) Date of Patent: Nov. 17, 2020

(54) RECOMBINANT MICROORGANISM FOR IMPROVED PRODUCTION OF ALANINE

(71) Applicant: BASF SE, Ludwigshafen am Rhein (DE)

(72) Inventors: Jennifer Jaitzig, New York, NY (US); Mukesh Kumar, White Plains, NY (US); Matthew Blankschien, Dobbs Ferry, NY (US); Shakir Ratani, Elmsford, NY (US); Qingzhao Wang, Ardsley, NY (US)

(73) Assignee: BASF SE, Ludwigshafen am Rhein (DE)

( * ) Notice: Subject to any disclaimer, the term of this patent is extended or adjusted under 35 U.S.C. 154(b) by 277 days.

(21) Appl. No.: 15/735,875

(22) PCT Filed: Jun. 9, 2016

(86) PCT No.: PCT/EP2016/063172
§ 371 (c)(1),
(2) Date: Dec. 12, 2017

(87) PCT Pub. No.: WO2016/198529
PCT Pub. Date: Dec. 15, 2016

(65) Prior Publication Data
US 2020/0032304 A1 Jan. 30, 2020

Related U.S. Application Data

(60) Provisional application No. 62/174,529, filed on Jun. 12, 2015, provisional application No. 62/180,081, filed on Jun. 16, 2015.

(51) Int. Cl.
*C12P 13/06* (2006.01)
*C12N 9/02* (2006.01)
*C12N 9/06* (2006.01)

(52) U.S. Cl.
CPC ............ *C12P 13/06* (2013.01); *C12N 9/0008* (2013.01); *C12N 9/0016* (2013.01); *C12Y 102/01011* (2013.01); *C12Y 104/01004* (2013.01)

(58) Field of Classification Search
CPC .............. C12P 13/06; C12N 9/02; C12N 9/06
See application file for complete search history.

(56) References Cited

U.S. PATENT DOCUMENTS

| 5,019,509 | A | 5/1991 | Rozzell |
| 5,565,350 | A | 10/1996 | Kmiec |
| 5,786,313 | A | 7/1998 | Schneider et al. |
| 2009/0098621 | A1 | 4/2009 | Rybak et al. |
| 2010/0047878 | A1 | 2/2010 | Nagai et al. |
| 2015/0376663 | A1 | 12/2015 | Schroeder et al. |
| 2016/0304917 | A1 | 10/2016 | Krawczyk et al. |
| 2016/0355829 | A1 | 12/2016 | Schroder et al. |
| 2017/0211106 | A1 | 7/2017 | Schroder et al. |
| 2018/0030418 | A1 | 2/2018 | Dantas Costa et al. |
| 2018/0148748 | A1 | 5/2018 | Jaitzig et al. |

FOREIGN PATENT DOCUMENTS

| RU | 2268305 C2 | 1/2006 |
| RU | 2006130318 A | 2/2008 |
| RU | 2515044 C2 | 5/2014 |
| WO | WO-8903427 A1 | 4/1989 |
| WO | WO-9429421 A1 | 12/1994 |
| WO | WO-0015815 A1 | 3/2000 |
| WO | WO-2005071062 A1 | 8/2005 |
| WO | WO-2007120198 A2 | 10/2007 |
| WO | WO-2008119009 A2 | 10/2008 |
| WO | WO-2008141226 A2 | 11/2008 |
| WO | WO-2009022754 A1 | 2/2009 |
| WO | WO-2009082029 A1 | 7/2009 |
| WO | WO-2012150155 A1 | 11/2012 |
| WO | WO-2012172822 A1 | 12/2012 |
| WO | WO-2014009435 A1 | 1/2014 |
| WO | WO-2015/028915 A1 | 3/2015 |
| WO | WO-2015044818 A1 | 4/2015 |
| WO | WO-2015087226 A1 | 6/2015 |
| WO | WO-2015/140226 A1 | 9/2015 |
| WO | WO-2016/063172 A1 | 4/2016 |
| WO | WO-2016/193351 A2 | 12/2016 |

OTHER PUBLICATIONS

U.S. Appl. No. 61/882,006, Qingzhao et al.
U.S. Appl. No. 61/882,007, Qingzhao et al.
U.S. Appl. No. 61/915,513, Qingzhao et al.
U.S. Appl. No. 61/915,516, Qingzhao et al.
U.S. Appl. No. 61/915,525, Qingzhao et al.
U.S. Appl. No. 61/915,527, Qingzhao et al.
U.S. Appl. No. 61/915,528, Qingzhao et al.
U.S. Appl. No. 61/881,964, Qingzhao et al.
U.S. Appl. No. 61/881,966, Qingzhao et al.
U.S. Appl. No. 61/881,968, Qingzhao et al.
U.S. Appl. No. 61/881,967, Qingzhao et al.
U.S. Appl. No. 61/881,970, Qingzhao et al.
U.S. Appl. No. 61/881,972, Qingzhao et al.
U.S. Appl. No. 61/881,969, Qingzhao et al.
U.S. Appl. No. 61/915,518, Qingzhao et al.
U.S. Appl. No. 61/915,534, Qingzhao et al.
U.S. Appl. No. 16/915,535, Qingzhao et al.
U.S. Appl. No. 62/174,529, Qingzhao et al.
U.S. Appl. No. 61/915,517, Qingzhao et al.

(Continued)

*Primary Examiner* — Karen Cochrane Carlson
(74) *Attorney, Agent, or Firm* — Faegre Drinker Biddle & Reath LLP

(57) ABSTRACT

The present invention relates to a recombinant nucleic acid molecule, a recombinant micro-organism, to a method for producing alanine and to the use of the recombinant nucleic acid molecule or the recombinant microorganism for the fermentative production of alanine.

Figure 1:
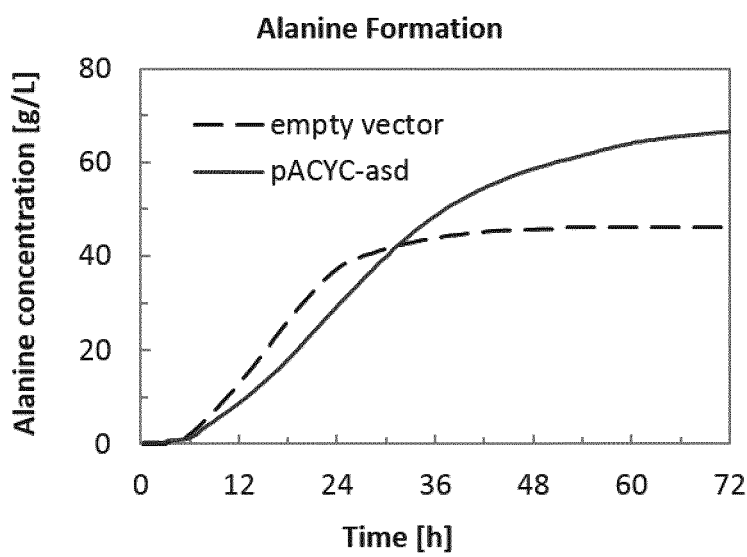

21 Claims, 1 Drawing Sheet
Specification includes a Sequence Listing.

(56) References Cited

OTHER PUBLICATIONS

Atabase EMBL [Online], Sequence 3 from Patent WO2009082029, XP002762308, retrieved from EBI accession No. EM PAT:HB463804, Database accession No. HB463804, 2009.

Fowler et al., "Increased Malonyl Coenzyme A Biosynthesis by Tuning the *Escherichia coli* Metabolic Network and Its Application to Flavanone Production," Applied and Environmental Microbiology, vol. 75, No. 18, pp. 5831-5839, 2009.

Guardiola et al., "*Escherichia coli* K-12 Mutants Altered in the Transport of Branched-Chain Amino Acids," Journal of Bacteriology, vol. 108, No. 3, pp. 1034-1044, 1971.

Lee et al., "Aerobic production of alanine by *Escherichia coli* aceF ldhA mutants expressing the Bacillus sphaericus alaD gene," Applied Genetics and Molecular Biotechnology, No. 65, pp. 56-60, 2004.

Smith et al., "Fed-batch two-phase production of alanine by a metabolically engineered *Escherichia coli*," Biotechnology Letters, vol. 28, pp. 1695-1700, 2006.

Hermann, "Industrial production of amino acids by coryneform bacteria," Journal of Biotechnology, vol. 104, pp. 155-172, 2003.

Xie et al., "Effect of transport proteins on L-isoleucine production with the L-isoleucine-producing strain *Corynebacterium glutamicum* YILW," Journal of Industrial Microbiology & Biotechnology, vol. 39, pp. 1549-1556, 2012.

Zhang et al., "Metabolic evolution of energy-conserving pathways for succinate production in *Escherichia coli*," Proceedings of the National Academy of Sciences, vol. 106, No. 48, pp. 20180-20185, 2009.

Zhang et al., "Production of L-alanine by metabolically engineered *Escherichia coli*," Applied Microbiology and Biotechnology, vol. 77, pp. 355-366, 2007.

Cahyanto et al., "Construction of Lactobacillus Plantarum Strain with Enhanced L-lysine Yield," Journal of Applied Microbiology, vol. 102, pp. 674-679, 2007.

Chen et al., "Cloning, Expression and Characterization of L-Aspartate β-Decarboxylase Gene from *Alcaligenes faecalis* CCRC 11585," Journal of Industrial Microbiology and Biology & Biotechnology, vol. 25, pp. 132-140, 2000.

Raczynska-Pawelec et al., "Characterization of *Campylobacter jejuni* and Gene Cloned in *Escherichia coli*", Acta Microbiologica Polonica, vol. 44, No. 3/4, pp. 227-241, 1995.

Wang et al., "Molecular Cloning of the Aspartate 4-Decarboxylase Gene from *Pseudomonas* sp. ATCC 19121 and Characterization of the Bifunctional Recombinant Enzyme", Applied Microbiology and Biotechnology, vol. 73, pp. 339-349, 2006.

International Search Report for PCT/EP2016/062457 dated Nov. 30, 2016.

International Search Report for PCT/EP2016/063172 dated Nov. 9, 2016.

Written Opinion of the International Searching Authority for PCT/EP2016/062457 dated Nov. 30, 2016.

Written Opinion of the International Searching Authority for PCT/EP2016/063172 dated Nov. 9, 2016.

RECOMBINANT MICROORGANISM FOR IMPROVED PRODUCTION OF ALANINE

CROSS-REFERENCE TO RELATED APPLICATIONS

This application is a national stage application (under 35 U.S.C. § 371) of PCT/EP2016/063172, filed Jun. 9, 2016, which claims benefit of U.S. Application Nos. 62/174,529, filed Jun. 12, 2015, and 62/180,081, filed Jun. 16, 2015, all of which are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sub_074008_1829_571772_ST25. The size of the text file is 111,583 bytes and the text file was created on Feb. 24, 2018.

FIELD OF THE INVENTION

The present invention relates to a recombinant nucleic acid molecule, a recombinant microorganism, to a method for producing alanine and to the use of the recombinant nucleic acid molecule or the recombinant microorganism for the fermentative production of alanine.

DESCRIPTION OF THE INVENTION

Amino acids are organic compounds with a carboxy-group and an amino-group. The most important amino acids are the alpha-amino acids where the amino group is located next to the carboxy-group. Proteins are based on alpha-amino acids.

Alanine has drawn considerable interest because it has been used as an additive in the food, feed and pharmaceutical industries. Moreover alanine is a raw material for the industrial production of alanine, N,N-bis(carboxymethyl)-, trisodium salt (MGDA, trade name Trilon M) which is a strong chelating agent, showing an excellent performance at dissolving organic and inorganic scale (WO94/29421, WO2012/150155). Trilon M grades are readily biodegradable according to standard OECD tests. Due to the superb ecological and toxicological profile, Trilon M grades are particularly suitable for use in products for end-consumers and the demand for such biodegradable complex builders is constantly rising.

Alanine can be produced by fermentation with Coryneform bacteria (Hermann, 2003: Industrial production of amino acids by Coryneform bacteria, J. of Biotechnol, 104, 155-172) or *E. coli*. (WO2007/120198, WO2008/119009).

Alanine production in *E. coli* is more efficient and widely used for industrial production of alanine as raw material for the chemical industry. As the demand of the chemical industry for alanine is increasing, there is a demand for improvement of productivity of fermentative production of alanine.

It is one object of the present invention to provide microorganisms which can be used in fermentative production of alanine with high yield and efficiency.

DETAILED DESCRIPTION OF THE INVENTION

A contribution to achieving the above mentioned aim is provided by a recombinant microorganism of the family of *Escherichia coli* (*E. coli*) having, compared to a respective reference microorganism, an introduced, increased or enhanced activity and/or expression of an asd or a gdhA gene encoding an aspartate-beta-semialdehyde dehydrogenase or a glutamate dehydrogenase in said microorganism compared to a respective control microorganism not comprising said introduced, increased or enhanced activity and/or expression of an asd or a gdhA gene.

Accordingly, one embodiment of the invention at hand is a recombinant microorganism comprising compared to a respective reference microorganism an introduced, increased or enhanced activity and/or expression of an asd or a gdhA gene encoding an aspartate-betasemialdehyde dehydrogenase or a glutamate dehydrogenase and having compared to a respective reference microorganism a higher yield and/or productivity of alanine in fermentative production.

The term "higher", "increase" or "enhanced" e.g. in reference to expression and/or activity of an enzyme or to yield or productivity, means a significantly higher, increased or enhanced expression and/or activity or yield or productivity as compared to a reference or control microorganism.

The term "reduced, repressed or deleted expression and/or activity of an enzyme", means a significantly reduced, repressed or deleted expression and/or activity and also encompasses an undetectable expression and/or activity of the respective enzymes in a reference or control microorganism.

The term "reference microorganism" as used herein means a control microorganism to which the recombinant microorganism is compared. This reference microorganism has substantially the same genotype as the recombinant microorganism with the exception of the difference to be analyzed. Preferably the reference microorganism is the strain from which the recombinant microorganism is originated. For example, a gene has been introduced into a wild type microorganism, thus creating a recombinant microorganism, in this case the wild type would be a suitable reference microorganism for this recombinant microorganism. It is also possible, that into a recombinant microorganism A a further mutation is introduced, thereby creating a recombinant microorganism B. The recombinant microorganism A would then be the suitable reference microorganism for recombinant microorganism B. In the event, the performance of a recombinant microorganism and the respective reference microorganism shall be compared both microorganisms are grown under substantially identical conditions.

It is obvious for the skilled person that a microorganism having an increased yield and/or productivity of alanine can also be used for the production of other metabolites that are closely related to alanine, for example metabolites that are intermediates in the alanine pathway, that share common intermediates with the alanine pathway or that are metabolites which use alanine as intermediate in their pathway. The microorganisms of the invention can also be easily adapted for having an increased yield and/or productivity of such related metabolites by increasing or introducing certain enzyme activities or by knocking out or decreasing certain enzyme activities.

Such metabolites are for example pyruvate, succinate, aspartate, malate, lactate, valine and leucine.

For example, in order to use the recombinant microorganism of the invention to produce succinate, the genes ldh, pfl, pta and adhE have to be knocked out and a PEP carboxylase gene and/or a pyruvate carboxylase gene have to be introduced in the genome of the microorganism of the invention. The respective pathway and necessary mutations are described for example in Zhang et al. (2009), PNAS (106) pp 20180-20185.

Accordingly, another embodiment of the invention at hand is a recombinant microorganism comprising compared to a respective reference microorganism an introduced, increased or enhanced activity and/or expression of an asd or a gdhA gene encoding an aspartate-betasemialdehyde dehydrogenase or a glutamate dehydrogenase and having compared to a respective reference microorganism a higher yield and/or productivity of pyruvate, succinate, aspartate, malate, lactate, valine and/or leucine in fermentative production.

Furthermore another embodiment of the invention at hand is a recombinant microorganism comprising compared to a respective reference microorganism an introduced, increased or enhanced activity and/or expression of an asd and a gdhA gene and having compared to a respective reference microorganism a higher yield and/or productivity of alanine in fermentative production.

In some embodiments, the microorganism is a prokaryotic cell. Suitable prokaryotic cells include Gram-positive, Gram negative and Gram-variable bacterial cells, preferably Gramnegative.

Thus, microorganisms that can be used in the present invention include, but are not limited to, *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, Brevibacterium divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus sp. CCM825, Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus sp. ATCC 15592, Rhodococcus sp. ATCC 19070, Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces avermitilis, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Xanthomonas citri* and so forth.

In some embodiments, the microorganism is a eukaryotic cell. Suitable eukaryotic cells include yeast cells, as for example *Saccharomyces* spec, such as *Saccharomyces cerevisiae, Hansenula* spec, such as *Hansenula polymorpha, Schizosaccharomyces* spec, such as *Schizosaccharomyces pombe, Kluyveromyces* spec, such as *Kluyveromyces lactis* and *Kluyveromyces marxianus, Yarrowia* spec, such as *Yarrowia lipolytica, Pichia* spec, such as *Pichia methanolica, Pichia stipites* and *Pichia pastoris, Zygosaccharomyces* spec, such as *Zygosaccharomyces rouxii* and *Zygosaccharomyces bailii, Candida* spec, such as *Candida boidinii, Candida utilis, Candida freyschussii, Candida glabrata* and *Candida sonorensis, Schwanniomyces* spec, such as *Schwanniomyces occidentalis, Arxula* spec, such as *Arxula adeninivorans, Ogataea* spec such as *Ogataea minuta, Klebsiella* spec, such as *Klebsiella pneumonia.*

Numerous bacterial industrial strains are especially suitable for use in the methods disclosed herein. In some embodiments, the microorganism is a species of the genus *Corynebacterium*, e.g. *C. acetophilum, C. glutamicum, C. callunae, C. acetoacidophilum, C. acetoglutamicum*. In some embodiments, the microorganism is a species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformis, B. clausii, B. stearothermophilus, B. halodurans, B. subtilis, B. pumilus*, and *B. amyloliquefaciens*. In some embodiments, the microorganism is a species of the genus *Erwinia*, e.g., *E. uredovora, E. carotovora, E. ananas, E. herbicola, E. punctata* and *E. terreus*. In some embodiments, the microorganism is a species of the genus *Escherichia*, e.g., *E. coli*. In other embodiments the microorganism is a species of the genus *Pantoea*, e.g., *P. citrea* or *P. agglomerans*. In still other embodiments, the microorganism is a species of the genus *Streptomyces*, e.g., *S. ambofaciens, S. achromogenes, S. avermitilis, S. coelicolor, S. aureofaciens, S. aureus, S. fungicidicus, S. griseus* or *S. lividans*. In further embodiments, the microorganism is a species of the genus *Zymomonas*, e.g., *Z. mobilis* or *Z. lipolytica*. In further embodiments, the microorganism is a species of the genus *Rhodococcus*, e.g. *R. opacus*.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (a) a reduced, repressed or deleted activity and/or expression of a pflB gene encoding a pyruvate formate lyase I, wherein the reduction, repression or deletion of the activity and/or expression of the pflB gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase), wherein the reduction, repression or deletion of the activity and/or expression of the adhE gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (c) a reduced, repressed or deleted activity and/or expression of a ldhA gene encoding a NAD-dependent fermentative D-lactate dehydrogenase, wherein the reduction, repression or deletion of the activity and/or expression of the ldhA gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (d) a reduced, repressed or deleted activity and/or expression of a pta gene encoding a phosphate acetyltransferase and/or a reduced, repressed or deleted activity and/or expression of an ackA gene encoding an acetate kinase A and propionate kinase 2, wherein the reduction, repression or deletion of the activity and/or expression of the pta gene and/or the ackA gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (e) a reduced, repressed or deleted activity and/or expression of a frdA gene encoding a fumarate reductase, wherein the reduction, repression or deletion of the activity and/or expression of the frdA gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (f) an introduced, increased or enhanced activity and/or expression of an alaD gene encoding an alanine dehydrogenase, wherein the increase or enhancement of the activity and/or expression of the alaD gene is determined compared to a respective reference microorganism.

In addition to the introduced, increased or enhanced activity and/or expression of an asd or a gdhA gene encoding an aspartate-beta-semialdehyde dehydrogenase or a glutamate dehydrogenase, the recombinant microorganism of the invention may further comprise (g) a reduced, repressed or deleted activity and/or expression of a dadX gene encoding a alanine racemase, wherein the reduction, repression or deletion of the activity and/or expression of the dadX gene is determined compared to a respective reference microorganism.

Preferably, the recombinant microorganism of the invention comprising the introduced, increased or enhanced activity and/or expression of an asd or a gdhA gene encoding an aspartate-beta-semialdehyde dehydrogenase or a glutamate dehydrogenase is additionally having at least two, more preferably at least three, even more preferably at least four, even more preferably at least five, most preferably all of the features selected from the group of (a) a reduced, repressed or deleted activity and/or expression of a pflB gene encoding a pyruvate formate lyase I and (b) a reduced, repressed or deleted activity and/or expression of a adhE gene encoding a bifunctional acetaldehyde-CoA dehydrogenase/iron-dependent alcohol dehydrogenase/pyruvate-formate lyase deactivase) and (c) a reduced, repressed or deleted activity and/or expression of a ldhA gene encoding a NAD-dependent fermentative D-lactate dehydrogenase and (d) a reduced, repressed or deleted activity and/or expression of a pta gene encoding a phosphate acetyltransferase and/or a reduced, repressed or deleted activity and/or expression of an ackA gene encoding an acetate kinase A and propionate kinase 2 and (e) a reduced, repressed or deleted activity and/or expression of a frdA gene encoding a fumarate reductase and (f) an introduced, increased or enhanced activity and/or expression of an alaD gene encoding an alanine dehydrogenase, (g) a reduced, repressed or deleted activity and/or expression of a dadX gene encoding an alanine racemase wherein the reduction, repression, deletion, introduction, increase or enhancement of the activity and/or expression of a gene is determined compared to a respective reference microorganism.

The alaD gene may be derived from any organism or may be a synthetic gene designed by man, for example having codon usage optimized for expression in the recombinant microorganism of the invention or being optimized for enzyme activity, e.g. having improved Vmax or Km. Preferably the alaD gene is derived from a microorganism of one of the the geni *Bacillus, Geobacillus, Paenibacillus, Halobacillus, Brevibacillus*. In a more preferred embodiment the alaD gene is derived from a microorganism of the genus *Geobacillus*. In a most preferred embodiment, the alaD gene is derived from *Geobacillus stearothermophilus*.

In a preferred embodiment the alaD gene has been codon optimized for the expression in the recombinant microorganism of the invention.

The microorganism of the invention may comprise further genetic modifications, such as mutations, knock-outs or enhanced or introduced enzyme activities that further improve yield and/or productivity of alanine, pyruvate, succinate, aspartate, malate, lactate, valine and/or leucine, preferably succinate or alanine, more preferably alanine. For example, the microorganism of the invention may further comprise an enhanced or increased expression and/or activity of the ygaW gene from *E. coli* or homologs or functional equivalents thereof which has recently been described to improve alanine productivity of a microorganism when overexpressed (WO2012/172822).

In a further example, the microorganism of the invention may in addition comprise any one of, any combination of or all of the genes that are specified and described in detail in the applications PCT/IB2014/064426 and PCT/IB2014/066686 and that are beneficial for production of alanine, pyruvate, succinate, aspartate, malate, lactate, valine and/or leucine, preferably succinate or alanine, more preferably alanine.

In one embodiment the asd gene encoding an aspartate-beta-semialdehyde dehydrogenase, is selected from the group of (i) a nucleic acid molecule comprising a sequence of SEQ ID NO: 25, or (ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 25, or (iii) a nucleic acid molecule hybridizing to a nucleic acid molecule having SEQ ID NO: 25 under medium stringent conditions, more preferably under high stringent conditions, most preferably under very high stringent conditions, or (iv) a nucleic acid molecule encoding a polypeptide of SEQ ID NO: 26, or (v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 26, wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 26.

In one embodiment the gdhA gene encoding a glutamate dehydrogenase, is selected from the group of (i) a nucleic acid molecule comprising a sequence of SEQ ID NO: 37, or (ii) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 37, or (iii) a nucleic acid molecule hybridizing to a nucleic acid molecule having SEQ ID NO: 37 under medium stringent conditions, more preferably under high stringent conditions, most preferably under very high stringent conditions, or (iv) a nucleic acid molecule encoding a polypeptide of SEQ ID NO: 38, or (v) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 38, wherein the polypeptide encoded by (ii), (iii) or (v) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 38.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise any one, two, three, four, five, six or all of the features as defined above under (a) to (g), wherein the pflB gene is selected from the group consisting of (A) a nucleic acid molecule comprising a sequence of SEQ ID NO: 5, or (B) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 5, or (C) a nucleic acid molecule hybridizing to a nucleic acid molecule having SEQ ID NO: 5 under medium stringent conditions, more preferably under high stringent conditions, most preferably under very high stringent conditions, or (D) a nucleic acid molecule encoding a polypeptide of SEQ ID NO: 6, or (E) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 6, wherein the polypeptide encoded by (B), (C) or (E) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 6 and wherein the adhE gene is selected from the group consisting of (F) a nucleic acid molecule comprising a sequence of SEQ ID NO: 7, or (G) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 7, or (H) a nucleic acid molecule hybridizing to a nucleic acid molecule having SEQ ID NO: 7 under medium stringent conditions, more preferably under high stringent conditions, most preferably under very high stringent conditions, or (I) a nucleic acid molecule encoding a polypeptide of SEQ ID NO: 8, or (J) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 8, wherein the polypeptide encoded by (G), (H) or (J) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 8 and wherein the IdhA gene is selected from the group consisting of (K) a nucleic acid molecule comprising a sequence of SEQ ID NO: 9, or (L) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 9, or (M) a nucleic acid molecule hybridizing to a nucleic acid molecule having SEQ ID NO: 9 under medium stringent conditions, more preferably under high stringent conditions, most preferably under very high stringent conditions, or (N) a nucleic acid molecule encoding a polypeptide of SEQ ID NO: 10, or (0) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 10, wherein the polypeptide encoded by (L), (M) or (0) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 10 and wherein the pta gene is selected from the group consisting of (P1) a nucleic acid molecule comprising a sequence of SEQ ID NO: 11, or (Q1) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 11, or (R1) a nucleic acid molecule hybridizing to a nucleic acid molecule having SEQ ID NO: 11 under medium stringent conditions, more preferably under high stringent conditions, most preferably under very high stringent conditions, or (S1) a nucleic acid molecule encoding a polypeptide of SEQ ID NO: 12, or (T1) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 12, wherein the polypeptide encoded by (Q1), (R1) or (T1) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 12 and wherein the ackA gene is selected from the group consisting of (P2) a nucleic acid molecule comprising a sequence of SEQ ID NO: 32, or (Q2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 32, or (R2) a nucleic acid molecule hybridizing to a nucleic acid molecule having SEQ ID NO: 32 under medium stringent conditions, more preferably under high stringent conditions, most preferably under very high stringent conditions, or (S2) a nucleic acid molecule encoding a polypeptide of SEQ ID NO: 33, or (T2) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 33, wherein the polypeptide encoded by (Q2), (R2) or (T2) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 33 and wherein the frdA gene is selected from the group consisting of (U) a nucleic acid molecule comprising a sequence of SEQ ID NO: 13, or (V) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 13, or (W) a nucleic acid molecule hybridizing to a nucleic acid molecule having SEQ ID NO: 13 under medium stringent conditions, more preferably under high stringent conditions, most preferably under very high stringent conditions, or (X) a nucleic acid molecule encoding a polypeptide of SEQ ID NO: 14, or (Y) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 14, wherein the polypeptide encoded by (V), (W) or (Y) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 14 and wherein the alaD gene is selected from the group consisting of (Z) a nucleic acid molecule comprising a sequence of SEQ ID NO: 1, or (AA) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 1, or (BB) a nucleic acid molecule hybridizing to a nucleic acid molecule having SEQ ID NO: 1 under medium stringent conditions, more preferably under high stringent conditions, most preferably under very high stringent conditions, or (CC) a nucleic acid molecule encoding a polypeptide of SEQ ID NO: 2, or (DD) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 2, wherein the polypeptide encoded by (AA), (BB) or (DD) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 2 and wherein the dadX gene is selected from the group consisting of (EE) a nucleic acid molecule comprising a sequence of SEQ ID NO: 15, or (FF) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 15, or (GG) a nucleic acid molecule hybridizing to a nucleic acid molecule having SEQ ID NO: 15 under medium stringent conditions, more preferably under high stringent conditions, most preferably under very high stringent conditions, or (HH) a nucleic acid molecule encoding a polypeptide of SEQ ID NO: 16, or (II) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 16, wherein the polypeptide encoded by (FF), (GG) or (II) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 16.

In a further example, the microorganism of the invention may in addition comprise any one of, any combination of or all of the genes that are specified and described in detail in the applications WO2015/044818 and PCT/IB2014/066686 and that are beneficial for production of alanine.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (h) a reduced, repressed or deleted activity and/or expression of a brnQ gene encoding a brnQ protein having a branched chain amino acid transporter activity, wherein the reduction, repression or deletion of the activity and/or expression of the brnQ gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (i) a reduced, repressed or deleted activity and/or expression of a gcvB gene encoding a non-protein encoding RNA, wherein the reduction, repression or deletion of the activity and/or expression of the gcvB gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (j) an increased or enhanced activity and/or expression of a zipA gene encoding a cell division protein involved in Z ring assembly, wherein the an increased or enhanced activity and/or expression of the zipA gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (k) an increased or enhanced activity and/or expression of a lpd gene encoding a lipoamide dehydrogenase, wherein the an increased or enhanced activity and/or expression of the lpd gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (l) a mutated IpxD gene encoding an UDP-3-O-(3-hydroxymyristoyl)-glucosamine N-acyltransferase protein, wherein IpxD gene is mutated compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (m) an increased or enhanced activity and/or expression of a gcvA gene encoding a DNA-binding protein, wherein the an increased or enhanced activity and/or expression of the gcvA gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase may further comprise (n) an increased or enhanced activity and/or expression of an ygaW gene encoding an alanine transporter, wherein the an increased or enhanced activity and/or expression of the ygaW gene is determined compared to a respective reference microorganism.

Preferably, the recombinant microorganism of the invention comprising the introduced, increased or enhanced activity and/or expression of an asd or a gdhA gene encoding an aspartate-beta-semialdehyde dehydrogenase or a glutamate dehydrogenase having the features as defined above under a) to g) is additionally having at least one, preferably at least two, more preferably at least three, more preferably at least four, more preferably at least five, even more preferably at least six, most preferably all of the features selected from the group of (h) a reduced, repressed or deleted activity and/or expression of a brnQ gene encoding a brnQ protein having a branched chain amino acid transporter activity and (i) a reduced, repressed or deleted activity and/or expression of a gcvB gene encoding a non-protein encoding RNA and (j) an increased and/or enhanced activity and/or expression of a zipA gene encoding cell division protein involved in Z ring assembly and (k) an increased and/or enhanced activity and/or expression of a lpd gene encoding a lipoamide dehydrogenase and (l) a changed activity of a IpxD gene encoding encoding an UDP-3-O-(3-hydroxymyristoyl)-glucosamine N-acyltransferase protein and (m) an increased and/or enhanced activity and/or expression of a gcvA gene encoding a DNA-binding protein and (n) an increased and/or enhanced activity and/or expression of a ygaW gene encoding an alanine transporter, wherein the reduction, repression, deletion, increase, enhancement or change of the activity and/or expression of a gene is determined compared to a respective reference microorganism.

The recombinant microorganism of the invention comprising the introduced, increased or enhanced activity and/or expression of an asd or a gdhA gene encoding an aspartate-betasemialdehyde dehydrogenase or a glutamate dehydrogenase and comprising any one, two, three, four, five, six or all of the features as defined above under (a) to (g) and/or (A) to (II), may further comprise any one, two, three, four, five, six or all of the features as defined above under (h) to (n)

wherein the brnQ gene is selected from the group consisting of
(1) a nucleic acid molecule comprising a sequence of SEQ ID NO: 23, or
(2) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 23, or
(3) a nucleic acid molecule hybridizing to a nucleic acid molecule having SEQ ID NO: 23 under medium stringent conditions, more preferably under high stringent conditions, most preferably under very high stringent conditions, or
(4) a nucleic acid molecule encoding a polypeptide of SEQ ID NO: 24, or
(5) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 24,
wherein the polypeptide encoded by (2), (3) or (5) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 23 and
wherein the gcvB gene is selected from the group consisting of
(6) a nucleic acid molecule comprising a sequence of SEQ ID NO: 31, or
(7) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 31, or
wherein the nucleic acid molecule under (7) is having at least 10%, 20% preferably at least 30% or 50%, more preferably at least 60% or 70%, even more preferably at least 75%, 80%, 85% or 90%, most preferred at least 95% of the activity as the nucleic acid molecule having SEQ ID NO: 31 and
wherein the zipA gene is selected from the group consisting of
(8) a nucleic acid molecule comprising a sequence of SEQ ID NO: 19, or
(9) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 19, or
(10) a nucleic acid molecule hybridizing to a nucleic acid molecule having SEQ ID NO: 19 under medium stringent conditions, more preferably under high stringent conditions, most preferably under very high stringent conditions, or
(11) a nucleic acid molecule encoding a polypeptide of SEQ ID NO: 20, or
(12) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 20,
wherein the polypeptide encoded by (9), (10) or (12) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 20 and
wherein the lpd gene is selected from the group consisting of
(13) a nucleic acid molecule comprising a sequence of SEQ ID NO: 21, or
(14) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 21, or
(15) a nucleic acid molecule hybridizing to a nucleic acid molecule having SEQ ID NO: 21 under medium stringent conditions, more preferably under high stringent conditions, most preferably under very high stringent conditions, or
(16) a nucleic acid molecule encoding a polypeptide of SEQ ID NO: 22, or
(17) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 22,
wherein the polypeptide encoded by (14), (15) or (17) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 22 and
wherein the lpxD gene is selected from the group consisting of
(23) a nucleic acid molecule comprising a sequence of SEQ ID NO: 27, or
(24) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 27, or
(25) a nucleic acid molecule hybridizing to a nucleic acid molecule having SEQ ID NO: 27 under medium stringent conditions, more preferably under high stringent conditions, most preferably under very high stringent conditions, or
(26) a nucleic acid molecule encoding a polypeptide of SEQ ID NO: 28, or
(27) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 28,
wherein the polypeptide encoded by (24), (25) or (27) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 28 and wherein the polypeptide encoded by (24) to (27) comprises at the position equivalent to position 15 of SEQ ID NO: 28 a threonine, and wherein the gcvA gene is selected from the group consisting of
- (28) a nucleic acid molecule comprising a sequence of SEQ ID NO: 29, or
- (29) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 29, or
- (30) a nucleic acid molecule hybridizing to a nucleic acid molecule having SEQ ID NO: 29 under medium stringent conditions, more preferably under high stringent conditions, most preferably under very high stringent conditions, or
- (31) a nucleic acid molecule encoding a polypeptide of SEQ ID NO: 30, or
- (32) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 30, wherein the polypeptide encoded by (29), (30) or (32) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 30 and wherein the ygaW gene is selected from the group consisting of
- (33) a nucleic acid molecule comprising a sequence of SEQ ID NO: 17, or
- (34) a nucleic acid molecule having at least 80%, preferably at least 85% for example at least 90%, more preferably at least 95% for example at least 96%, even more preferably at least 97% for example at least 98%, most preferably at least 99% identity to a nucleic acid molecule of SEQ ID NO: 17, or
- (35) a nucleic acid molecule hybridizing to a nucleic acid molecule having SEQ ID NO: 17 under medium stringent conditions, more preferably under high stringent conditions, most preferably under very high stringent conditions, or
- (36) a nucleic acid molecule encoding a polypeptide of SEQ ID NO: 18, or
- (37) a nucleic acid molecule encoding a polypeptide having at least 60% preferably at least 70% for example at least 75%, more preferably at least 80% for example at least 85%, even more preferably at least 90% for example at least 95%, most preferably at least 96%, at least 97%, at least 98% or at least 99% homology to a polypeptide of SEQ ID NO: 18, wherein the polypeptide encoded by (34), (35) or (37) is having at least 10%, 20% preferably at least 30% or 50%, more preferably at least 60% or 70%, even more preferably at least 75%, 80%, 85% or 90%, most preferred at least 95% of the activity as the polypeptide having SEQ ID NO: 18 and wherein the polypeptide encoded by (34) to (37) preferably comprises at the position equivalent to position 5 of SEQ ID NO: 18 preferably a histidine, asparagine, arginine or tyrosine.

Preferably the recombinant microorganism of the invention comprising the introduced, increased or enhanced activity and/or expression of an asd or a gdhA gene encoding an aspartate-beta-semialdehyde dehydrogenase or a glutamate dehydrogenase is comprising all of the features as defined above under (a) to (g) or (A) to (II) and (j), (k) and (n) or (13) to (17) and (33) to (37).

A further embodiment of the invention is a composition comprising one or more recombinant microorganisms of the invention as defined above. The composition may further comprise a medium that allows grow of the recombinant microorganism of the invention. The medium may additionally comprise a carbon source such as hexoses, pentoses or polyols for example sucrose, glucose, fructose, galactose, mannose, raffinose, xylose, arabinose, xylulose, glycerol, mannitol, arabitol, xylitol, starch, cellulose, lignocellulose or combinations thereof. Preferably the carbon source is glucose of sucrose, more preferably the carbon source is glucose.

In a preferred embodiment the composition comprises the microorganism of the invention and NBS medium, AM1 medium or PPMO1 medium. More preferably the composition further comprises a carbon source, preferably a sugar. The ingredients of these media are known to a skilled person.

Preferably NBS medium comprises per liter
1-5 g, preferably 3.5 g $KH_2PO_4$ and
1-10 g, preferably 5.0 g $K_2HPO_4$ and
1-5 g, preferably 3.5 g $(NH_4)_2HPO_4$ and
0.1-1 g, preferably 0.25 g $MgSO_4$-$7H_2O$ and
5-25 mg, preferably 15 mg $CaCL_2$-$2H_2O$ and
0.1-1 mg, preferably 0.5 mg Thiamine and
0.1-5 ml, preferably 1 ml trace metal stock, wherein the trace metal stock comprises 0.5-5 g, preferably 1.6 g $FeCL_3$-$6H_2O$; 0.05-0.5 g, preferably 0.2 g $CoCl_2$-$6H_2O$; 0.01-0.5 g, preferably 0.1 g $CuCl_2$-$2H_2O$; 0.1-0.5 g, preferably 0.2 g $ZnCl_2$; 0.05-0.5 g, preferably 0.2 g $NaMoO_4$-$2H_2O$; 0.001-0.1 g, preferably 0.05 g $H_3BO_3$ per liter 0.01-1 M, preferably 0.1 M HCL.

The preferred carbon source in the NBS medium is glucose or sucrose, preferably 2%-18% glucose or 2%-16% sucrose.

Preferably AM 1 medium comprises per liter 0.1-10 mM, preferably 1 mM betain solution
1-10 g, preferably 2.6 g $(NH4)_2HPO_4$ and
0.1-5 g, preferably 0.87 g $NH_4H_2PO_4$ and
0.05-2.5 g, preferably 0.15 g KCl and
0.05-5 g, preferably 0.37 g $MgSO_4$-$7H_2O$ and
0.1-5 ml, preferably 1 ml trace metal stock, wherein the trace metal stock comprises per liter 0.01-1 M, preferably 0.12 M HCL, 1-5 g, preferably 2.4 g $FeCL_3$-$6H_2O$; 0.1-1 g, preferably 0.3 g $CoCl_2$-$6H_2O$; 0.1-1 g, preferably 0.21 g $CuCl_2$-$2H_2O$; 0.1-1 g, preferably 0.3 g $ZnCl_2$; 0.1-1 g, preferably 0.27 g $NaMoO4$-$2H_2O$; 0.01-0.5 g, preferably 0.068 g $H_3BO_3$ and 0.1-1 g, preferably 0.5 g $MnCl_2$-$4H_2O$, and optionally 1-30 g, preferably 15 g $(NH_4)_2SO_4$.

The preferred carbon source in the NBS medium is glucose or sucrose, preferably 2%-18% glucose or 2%-16% sucrose.

Preferably PPM01 medium comprises per liter
0.05-5 g, preferably 0.37 g $MgSO_4$-$7H_2O$ and
0.1-10 g, preferably 1 g $(NH_4)_2SO_4$ and
0.05-5 g, preferably 0.46 g betaine and
0.001-0.5 g, preferably 0.05 g Cyanocobalamin (B12) and
1-10 g, preferably 3.74 g $KH_2PO_4$ and
0.1-5 ml, preferably 1 ml trace metal stock, wherein the trace metal stock comprises per liter 10-100 mM, preferably 60 mM sulfuric acid, 1-10 g, preferably 3.48 g $(NH_4)_2Fe(II)(SO_4)_2\text{-}7H_2O$; 0.1-1 g, preferably 0.35 g $CoSO_4\text{-}7H_2O$; 0.1-1 g, preferably 0.31 g $CuSO_4\text{-}5H_2O$; 0.1-5 g, preferably 0.63 g $ZnSO_4\text{-}7H_2O$; 0.1-1 g, preferably 0.27 g $MnSO_4\text{—}H_2O$; 0.01-1 g, preferably 0.07 g $NaMoO_4\text{-}2H_2O$ and 0.1-5 g, preferably 0.43 g $H_3BO_3$.

The preferred carbon source in the PPM01 medium is glucose monohydrate, preferably 10-500 g, more preferably 140 g glucose monohydrate per liter medium.

A further embodiment of the invention is a method for producing a recombinant microorganism with enhanced alanine yield or productivity, which comprises the following steps:
  (I) introducing, increasing or enhancing of one or more activity and/or expression of the asd gene or the gdhA gene or as defined above under (i) to (v) in a microorganism; and
  (II) generating, identifying and isolating a recombinant microorganism with enhanced alanine yield or productivity compared to a corresponding microorganism without introduced, increased or enhanced activity and/or expression of the asd gene or the gdhA gene or as defined above under (i) to (v).

In a preferred embodiment of the method for producing a recombinant microorganism of the invention the method further comprises the step of reducing, repressing or deleting the activity and/or expression of at least one, at least two, at least three, at least four, at least five, at least six or all of the pflB gene, adhE gene, IdhA gene, pta gene, ackA gene, frdA gene or dadX gene for example as defined above under (A) to (Y) and (EE) to (II) and/or the step of introducing, increasing or enhancing activity and/or expression of an alaD gene, lpd gene, zipA gene and ygaW gene for example as defined above under (Z) to (DD), (8) to (17) and (33) to (37).

A more preferred method for producing a recombinant microorganism of the invention comprises the step of reducing, repressing or deleting the activity and/or expression of all of the pflB gene, adhE gene, IdhA gene, ackA gene and frdA gene and the step of introducing, increasing or enhancing activity and/or expression of an alaD gene, lpd gene, zipA gene and ygaW gene.

In one embodiment of the method for producing a recombinant microorganism of the invention the microorganism is selected from the group consisting of species of the genus *Corynebacterium*, e.g. *C. acetophilum, C. glutamicum, C. callunae, C. acetoacidophilum, C. acetoglutamicum*, species of the genus *Bacillus*, e.g., *B. thuringiensis, B. anthracis, B. megaterium, B. subtilis, B. lentils, B. circulans, B. pumilus, B. lautus, B. coagulans, B. brevis, B. firmus, B. alkaophius, B. licheniformis, B. clausii, B. stearothermophilus, B. halodurans, B. subtilis, B. pumilus*, and *B. amyloliquefaciens*, species of the genus *Erwinia*, e.g., *E. uredovora, E. carotovora, E. ananas, E. herbicola, E. punctate, E. terreus*, species of the genus *Escherichia*, e.g., *E. coli*, species of the genus *Pantoea*, e.g., *P. citrea, P. agglomerans*, species of the genus *Streptomyces*, e.g., *S. ambofaciens, S. achromogenes, S. avermitilis, S. coelicolor, S. aureofaciens, S. aureus, S. fungicidicus, S. griseus, S. lividans*, species of the genus *Zymomonas*, e.g., *Z. mobilis* or *Z. lipolytica* species of the genus *Rhodococcus*, e.g. *R. opacus*, species of the genus *Saccharomyces* spec, such as *Saccharomyces cerevisiae*, species of the genus *Hansenula* spec, such as *Hansenula polymorpha*, species of the genus *Schizosaccharomyces* spec, such as *Schizosaccharomyces pombe*, species of the genus *Kluyveromyces* spec, such as *Kluyveromyces lactis* and *Kluyveromyces marxianus*, species of the genus *Yarrowia* spec, such as *Yarrowia lipolytica*, species of the genus *Pichia* spec, such as *Pichia methanolica, Pichia stipites* and *Pichia pastoris*, species of the genus *Zygosaccharomyces* spec, such as *Zygosaccharomyces rouxii* and *Zygosaccharomyces bailii*, species of the genus *Candida* spec, such as *Candida boidinii, Candida utilis, Candida freyschussii, Candida glabrata* and *Candida sonorensis*, species of the genus *Schwanniomyces* spec, such as *Schwanniomyces occidentalis*, species of the genus *Arxula* spec, such as *Arxula adeninivorans*, species of the genus *Ogataea* spec such as *Ogataea minuta*, species of the genus *Klebsiella* spec, such as *Klebsiella* pneumoniaand.

Preferably the microorganism is selected from the family of Enterobacteriaceae, preferably of the genus *Escherichia*, for example *Escherichia coli* (*E. coli*), preferably the strain *E. coli* W, which corresponds to DSMZ 1116, which corresponds to ATCC9637.

A further embodiment of the invention is a method of producing alanine, preferably L-alanine, comprising culturing one or more recombinant microorganism as defined above under conditions that allow for the production of alanine, preferably L-alanine.

In some embodiments, the recombinant microorganisms encompassed by the invention are grown under batch or continuous fermentations conditions. Classical batch fermentation is a closed system, wherein the compositions of the medium is set at the beginning of the fermentation and is not subject to artificial alterations during the fermentation. A variation of the batch system is a fed-batch fermentation. In this variation, the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation which also finds use in the present invention is a system where a defined fermentation medium is added continuously to a bioreactor and an equal amount of conditioned medium (e.g., containing the desired end-products) is removed simultaneously for processing. Continuous fermentation generally maintains the cultures at a constant high density where cells are primarily in the growth phase where production of end products is enhanced. Continuous fermentation systems strive to maintain steady state growth conditions. Methods for modulating nutrients and growth factors for continuous fermentation processes as well as techniques for maximizing the rate of product formation are well known in the art of industrial microbiology.

In some embodiments, fermentations are carried out in a temperature within the range of from about 10° C. to about 60° C., from about 15° C. to about 50° C., from about 20° C. to about 45° C., from about 25° C. to about 45° C., from about 30° C. to about 45° C. and from about 25° C. to about 40° C. In a preferred embodiment the temperature is about 34° C., 35° C. or 36° C. In a most preferred embodiment the temperature is about 37° C. or 38° C.

In some other embodiments, the fermentation is carried out for a period of time within the range of from about 8 hours to 240 hours, from about 8 hours to about 168 hours, from about 10 hours to about 144 hours, from about 15 hours to about 120 hours, or from about 20 hours to about 72 hours. Preferably the fermentation is carried out from about 20 hours to about 40 hours.

In some other embodiments, the fermentation is carried out at a pH in the range of about 4 to about 9, in the range of about 4.5 to about 8.5, in the range of about 5 to about 8, or in the range of about 5.5 to about 7.5. Preferably the fermentation will be carried out at a pH of 7.

In one embodiment of the method of producing alanine, more preferably L-alanine, the microorganism is cultured in a medium comprising between 1% and 30% (w/v) of a sugar, between 5% and 25% (w/v) of a sugar, between 10% and 20% (w/v) of a sugar, between 12% and 18% (w/v) of a sugar. Preferably the microorganism is cultured in a medium comprising between 13% and 15% (w/v) of a sugar.

In another embodiment of the method for producing alanine, more preferably L-alanine the yield of alanine is at least 80% for example at least 81%, at least 82%, at least 83%, at least 84% or at least 85%. Preferably the yield is at least 86%, at least 87%, at least 88%, at least 89% or at least 90%. More preferably the yield is at least 90.5%, at least 91%, at least 91.5%, at least 92%, at least 92.5%, at least 93%, at least 93.5%, at least 94% or at least 94.5%. In an even more preferred embodiment the yield is at least 95% or at least 95.5%. In a most preferred embodiment, the yield is at least 96%. The percent yield is calculated as gram product produced from gram glucose in the medium. Hence, when the medium contained 100 g glucose and the fermentation yielded 98 g alanine, the yield would be 98%. In another embodiment of the method for producing alanine preferably L-alanine is produced, wherein the chiral purity of L-alanine is at least 90%, at least 91%, at least 92%, at least 93% or at least 94%. In a preferred embodiment the chiral purity of L-alanine is at least 95% or at least 95.5%. In a more preferred embodiment, the chiral purity of L-alanine is at least 96% or at least 96.5% or at least 97%. In an even more preferred embodiment the chiral purity of L-alanine is at least 97.5%, at least 98% or at least 98.5% for example at least 99%. Even more preferably the chiral purity of L-alanine is at least 99.5% or at least 99.6% for example at least 99.7%, at least 99.8%, or at least 99.9%. In a most preferred embodiment chiral pure L-alanine is produced.

Another embodiment of the invention is a method of culturing or growing any of the genetically modified microorganisms as defined above, the method comprising inoculating a culture medium with one or more genetically modified microorganism and culturing or growing said genetically modified microorganism in culture medium under conditions as defined above.

The use of a recombinant microorganism as defined above or a composition as defined above for the fermentative production of alanine, preferably L-alanine is an additional embodiment of the invention.

The recombinant microorganism according to the present invention is characterized in that, compared to a respective reference microorganism for example a wild type or an alanine high production strain, the expression and/or the activity of the enzyme that is encoded by the asd gene or the gdhA gene is increased or enhanced.

Furthermore the recombinant microorganism according to the present invention is characterized in that, compared to a respective reference microorganism for example a wild type or an alanine high production strain the expression and/or the activity of both enzymes encoded by the asd gene and the gdhA gene are increased or enhanced.

In one embodiment the decrease of the expression and/or activity of a genes is achieved by a deactivation, mutation or knock-out of the gene. This could be done by deletion of part or total of the coding region and/or the promoter of the gene, by mutation of the gene such as insertion or deletion of a number of nucleotides for example one or two nucleotides leading to a frameshift in the coding region of the gene, introduction of stop codons in the coding region, inactivation of the promoter of the gene by for example deleting or mutating promoter boxes such as ribosomal entry sides, the TATA box and the like. The decrease may also be achieved by degrading the transcript of the gene for example by means of introduction of ribozymes, dsRNA, antisense RNA or antisense oligonucleotides. The decrease of the activity of a gene may be achieved by expressing antibodies or aptamers in the cell specifically binding the target enzyme. Other methods for the decrease of the expression and/or activity of a gene are known to a skilled person.

The reduced expression and/or activity of the enzymes disclosed herein can be a reduction of the expression and/or enzymatic activity by at least 50%, compared to the expression and/or activity of said enzyme in a respective reference microorganism for example the wild type of the microorganism, or a reduction of the expression and/or enzymatic activity by at least 90%, or more preferably a reduction of expression and/or the enzymatic activity by at least 95%, or more preferably an expression and/or reduction of the enzymatic activity by at least 98%, or even more preferably a reduction of the expression and/or enzymatic activity by at least 99% or even more preferably a reduction of the expression and/or the enzymatic activity by at least 99.9%. In a most preferred embodiment the expression and/or activity of the enzymes is not detectable in the microorganism of the invention.

The enhanced or increased expression and/or activity of the enzymes disclosed herein can be an increase of the expression and/or enzymatic activity by at least 25%, compared to the expression and/or activity of said enzyme in a respective reference microorganism for example the wild type of the microorganism, or an increase of the expression and/or enzymatic activity by at least 50%, or more preferably an increase of expression and/or the enzymatic activity by at least 100%, or more preferably an increase of the expression and/or of the enzymatic activity by at least 3 fold, for example at least 5 fold, or even more preferably an increase of the expression and/or enzymatic activity by at least 10 fold or even more preferably an increase of the expression and/or the enzymatic activity by at least 20 fold.

The increase of the expression and/or activity of the asd gene or the gdhA gene leads to an improved yield and/or productivity of alanine in the recombinant microorganism of the invention compared to a respective reference microorganism. Therefore the increase of the expression and/or activity of the asd gene or the gdhA gene may be determined by measuring alanine yield or productivity of the recombinant microorganism of the invention compared to a respective reference microorganism. Methods for fermentative production of metabolites, for example alanine are known to a skilled person and also described herein. Improved yield of e.g. alanine in fermentation by the microorganism of the invention compared to yield of alanine in fermentation by a respective reference microorganism is a measure for the increase of the expression and or activity of the asd gene or the gdhA gene.

Methods for determining the lactate dehydrogenase (ldhA) expression or activity are, for example, disclosed by Bunch et al. in "The ldhA gene encoding the fermentative lactate de hydrogenase of *Escherichia Coli*", Microbiology (1997), Vol. 143, pages 187-155; or Bergmeyer, H. U., Bergmeyer J. and Grassl, M. (1983-1986) in "Methods of Enzymatic Analysis", 3rd Edition, Volume III, pages 126-133, Verlag Chemie, Weinheim; or Enzymes in Industry: Production and Applications, Second Edition (2004), Wolfgang Aehle, page 23. Preferred is the last method.

Methods for determining the pyruvate formate lyase I (pflB) expression or activity are, for example, disclosed in Knappe J, Blaschkowski H P, Grobner P, Schmitt T (1974). "Pyruvate formate-lyase of *Escherichia coli*: the acetyl-enzyme intermediate." Eur J Biochem 1974; 50(1); 253-63. PMID: 4615902; in KNAPPE, Joachim, et al. "Pyruvate Formate-Lyase of *Escherichia coli*: the Acetyl-Enzyme Intermediate." European Journal of Biochemistry 50.1 (1974): 253-263; in Wong, Kenny K., et al. "Molecular properties of pyruvate formatelyase activating enzyme." Biochemistry 32.51 (1993): 14102-14110 and in Nnyepi, Mbako R., Yi Peng, and Joan B. Broderick. "Inactivation of *E. coli* pyruvate formate-lyase: Role of AdhE and small molecules." Archives of biochemistry and biophysics 459.1 (2007): 1-9.

Methods for determining the bifunctional acetaldehyde-CoA dehydrogenase/iron-dependent alcohol dehydrogenase/pyruvate-formate lyase deactivase (adhE) expression or activity are, for example, disclosed in Membrillo-Hernandez, Jorge, et al. "Evolution of the adhE Gene Product of *Escherichia coli* from a Functional Reductase to a Dehydrogenase GENETIC AND BIOCHEMICAL STUDIES OF THE MUTANT PROTEINS." Journal of Biological Chemistry 275.43 (2000): 33869-33875 and in Mbako R. Nnyepi, Yi Peng, Joan B. Broderick, Inactivation of *E. coli* pyruvate formate-lyase: Role of AdhE and small molecules, Archives of Biochemistry and Biophysics, Volume 459, Issue 1, 1 Mar. 2007, Pages 1-9.

Methods for determining the phosphate acetyltransferase (pta) expression or activity are, for example, disclosed in Dittrich, Cheryl R., George N. Bennett, and Ka-Yiu San. "Characterization of the Acetate-Producing Pathways in *Escherichia coli*." Biotechnology progress 21.4 (2005): 1062-1067 and in Brown, T. D. K., M. C. Jones-Mortimer, and H. L. Kornberg. "The enzymic interconversion of acetate and acetyl-coenzyme A in *Escherichia coli*." Journal of general microbiology 102.2 (1977): 327-336.

Methods for determining the fumarate reductase (frdA) expression or activity are, for example, disclosed in Dickie, Peter, and Joel H. Weiner. "Purification and characterization of membrane-bound fumarate reductase from anaerobically grown *Escherichia coli*." Canadian journal of biochemistry 57.6 (1979): 813-821; in Cecchini, Gary, et al. "Reconstitution of quinone reduction and characterization of *Escherichia coli* fumarate reductase activity." Journal of Biological Chemistry 261.4 (1986): 1808-1814 or in Schröder, I., et al. "Identification of active site residues of *Escherichia coli* fumarate reductase by site-directed mutagenesis." Journal of Biological Chemistry 266.21 (1991): 13572-13579.

Methods for determining the alanine dehydrogenase (alaD) expression or activity are, for example, disclosed in Sakamoto, Y., Nagata, S., Esaki, N., Tanaka, H., Soda, K. "Gene cloning, purification and characterization of thermostable alanine dehydrogenase of *Bacillus stearothermophilus*" J Fermen. Bioeng. 69 (1990):154-158.

The term "reduced expression of an enzyme" includes, for example, the expression of the enzyme by said genetically manipulated (e.g., genetically engineered) microorganism at a lower level than that expressed by a respective reference microorganism for example the wild type of said microorganism. Genetic manipulations for reducing the expression of an enzyme can include, but are not limited to, deleting the gene or parts thereof encoding for the enzyme, altering or modifying regulatory sequences or sites associated with expression of the gene encoding the enzyme (e.g., by removing strong promoters or repressible promoters), modifying proteins (e.g., regulatory proteins, suppressors, enhancers, transcriptional activators and the like) involved in transcription of the gene encoding the enzyme and/or the translation of the gene product, or any other conventional means of decreasing expression of a particular gene routine in the art (including, but not limited to, the use of antisense nucleic acid molecules or other methods to knock-out or block expression of the target protein). Further on, one may introduce destabilizing elements into the mRNA or introduce genetic modifications leading to deterioration of ribosomal binding sites (RBS) of the RNA. It is also possible to change the codon usage of the gene in a way, that the translation efficiency and speed is decreased.

A reduced activity of an enzyme can also be obtained by introducing one or more deleterious gene mutations which lead to a reduced activity of the enzyme. Furthermore, a reduction of the activity of an enzyme may also include an inactivation (or the reduced expression) of activating enzymes which are necessary in order to activate the enzyme the activity of which is to be reduced. By the latter approach the enzyme the activity of which is to be reduced is preferably kept in an inactivated state.

A deleterious mutation according to this application is any mutation within a gene comprising promoter and coding region that lead to a decreased or deleted protein activity of the protein encoded by the coding region of the gene. Such deleterious mutations comprise for example frameshifts, introduction of stop-codons in the coding region, mutation of promoter elements such as the TATA box that prevent transcription and the like.

Microorganisms having an increased or enhanced expression and/or activity of the enzyme encoded by the asd gene or the gdhA gene may occur naturally, i.e. due to spontaneous mutations. A microorganism can be modified to have significantly increased activity of the enzyme that is encoded by one or more of said genes by various techniques, such as chemical treatment or radiation. To this end, microorganisms will be treated by, e.g., a mutagenizing chemical agent, X-rays, or UV light. In a subsequent step, those microorganisms which have an increased expression and/or activity of the enzyme that is encoded by one or more of said genes will be selected. Recombinant microorganisms are also obtainable by homologous recombination techniques which aim to substitute one or more of said genes with a corresponding gene that encodes for an enzyme which, compared to the enzyme encoded by the wild type gene, has an increased expression and/or activity.

According to one embodiment of the recombinant microorganism according to the present invention, an increase of the expression and/or activity of the enzyme encoded by the asd gene or the gdhA gene may be achieved by a modification of the asd gene or the gdhA gene, wherein this/these gene modification(s) is(are) preferably realized by multiplication of the copy-number of the asd gene or the gdhA gene in the genome of the microorganism, by introducing the gene on a self-replicating expression vector into the microorganism, by exchanging the promoter of the asd gene or the gdhA gene against a stronger promoter or by converting the endogenous promoter of the gene into a stronger promoter, e.g. by introducing point-mutations into the promoter sequence.

Further the activity of the asd gene or the gdhA gene may be enhanced by mutating the gene in order to achieve amino acid exchanges in the protein which improve activity of the gene. Such methods are known to a skilled person.

A mutation into the above-gene can be introduced, for example, by site-directed or random mutagenesis, followed by an introduction of the modified gene into the genome of the microorganism by recombination. Variants of the genes can be are generated by mutating the gene sequences by means of PCR. The "Quickchange Site-directed Mutagenesis Kit" (Stratagene) can be used to carry out a directed mutagenesis. A random mutagenesis over the entire coding sequence, or else only part thereof, can be performed with the aid of the "GeneMorph II Random Mutagenesis Kit" (Stratagene). The mutagenesis rate is set to the desired amount of mutations via the amount of the template DNA used. Multiple mutations are generated by the targeted combination of individual mutations or by the sequential performance of several mutagenesis cycles.

In the following, a suitable technique for recombination, in particular for introducing a mutation or for deleting sequences, is described.

This technique is also sometimes referred to as the "Campbell recombination" herein (Leenhouts et al., *Appl Env Microbio* (1989), Vol. 55, pages 394-400). "Campbell in", as used herein, refers to a transformant of an original host cell in which an entire circular double stranded DNA molecule (for example a plasmid) has integrated into a chromosome by a single homologous recombination event (a cross in event), and that effectively results in the insertion of a linearized version of said circular DNA molecule into a first DNA sequence of the chromosome that is homologous to a first DNA sequence of the said circular DNA molecule. "Campbelled in" refers to the linearized DNA sequence that has been integrated into the chromosome of a "Campbell in" transformant. A "Campbell in" contains a duplication of the first homologous DNA sequence, each copy of which includes and surrounds a copy of the homologous recombination crossover point.

"Campbell out", as used herein, refers to a cell descending from a "Campbell in" transformant, in which a second homologous recombination event (a cross out event) has occurred between a second DNA sequence that is contained on the linearized inserted DNA of the "Campbelled in" DNA, and a second DNA sequence of chromosomal origin, which is homologous to the second DNA sequence of said linearized insert, the second recombination event resulting in the deletion (jettisoning) of a portion of the integrated DNA sequence, but, importantly, also resulting in a portion (this can be as little as a single base) of the integrated Campbelled in DNA remaining in the chromosome, such that compared to the original host cell, the "Campbell out" cell contains one or more intentional changes in the chromosome (for example, a single base substitution, multiple base substitutions, insertion of a heterologous gene or DNA sequence, insertion of an additional copy or copies of a homologous gene or a modified homologous gene, or insertion of a DNA sequence comprising more than one of these aforementioned examples listed above). A "Campbell out" cell is, preferably, obtained by a counter-selection against a gene that is contained in a portion (the portion that is desired to be jettisoned) of the "Campbelled in" DNA sequence, for example the *Bacillus subtillis* sacB-gene, which is lethal when expressed in a cell that is grown in the presence of about 5% to 10% sucrose. Either with or without a counter-selection, a desired "Campbell out" cell can be obtained or identified by screening for the desired cell, using any screenable phenotype, such as, but not limited to, colony morphology, colony color, presence or absence of antibiotic resistance, presence or absence of a given DNA sequence by polymerase chain reaction, presence or absence of an auxotrophy, presence or absence of an enzyme, colony nucleic acid hybridization, antibody screening, etc. The term "Campbell in" and "Campbell out" can also be used as verbs in various tenses to refer to the method or process described above.

It is understood that the homologous recombination events that leads to a "Campbell in" or "Campbell out" can occur over a range of DNA bases within the homologous DNA sequence, and since the homologous sequences will be identical to each other for at least part of this range, it is not usually possible to specify exactly where the crossover event occurred. In other words, it is not possible to specify precisely which sequence was originally from the inserted DNA, and which was originally from the chromosomal DNA. Moreover, the first homologous DNA sequence and the second homologous DNA sequence are usually separated by a region of partial non-homology, and it is this region of non-homology that remains deposited in a chromosome of the "Campbell out" cell.

Preferably, first and second homologous DNA sequence are at least about 200 base pairs in length, and can be up to several thousand base pairs in length. However, the procedure can be made to work with shorter or longer sequences. For example, a length for the first and second homologous sequences can range from about 500 to 2000 bases, and the obtaining of a "Campbell out" from a "Campbell in" is facilitated by arranging the first and second homologous sequences to be approximately the same length, preferably with a difference of less than 200 base pairs and most preferably with the shorter of the two being at least 70% of the length of the longer in base pairs.

In one embodiment the induction of the expression and/or activity of asd is achieved by an activation of the asd gene which encodes the aspartate-beta-semialdehyde dehydrogenase.

In one embodiment the induction of the expression and/or activity of gdhA is achieved by an activation of the gdhA gene which encodes the glutamate dehydrogenase.

The terms "alanine, pyruvate, succinate, aspartate, malate, lactate, valine and/or leucine", as used in the context of the present invention, has to be understood in their broadest sense and also encompasses salts thereof, as for example alkali metal salts, like $Na^+$ and $K^+$-salts, or earth alkali salts, like $Mg^{2+}$ and $Ca^{2+}$-salts, or ammonium salts or anhydrides of alanine, pyruvate, succinate, aspartate, malate, lactate, valine and/or leucine.

Preferably, alanine, pyruvate, succinate, aspartate, malate, lactate, valine and/or leucine, preferably succinate or alanine, more preferably alanine is produced under microaerobic conditions. Aerobic or anaerobic conditions may be also used.

Microaerobic means that the concentration of oxygen is less than that in air. According to one embodiment microaerobic means oxygen tension between 5 and 27 mm Hg, preferably between 10 and 20 Hg (Megan Falsetta et al. (2011), The composition and metabolic phenotype of *Neisseria gonorrhoeae* biofilms, Frontiers in Microbiology, Vol 2, page 1 to 11). Preferably the microaerobic conditions are established with 0.1 to 1 vvm air flow.

Anaerobic conditions may be established by means of conventional techniques, as for example by degassing the constituents of the reaction medium and maintaining anaerobic conditions by introducing carbon dioxide or nitrogen or mixtures thereof and optionally hydrogen at a flow rate of, for example, 0.1 to 1 or 0.2 to 0.5 vvm. Aerobic conditions may be established by means of conventional techniques, as for example by introducing air or oxygen at a flow rate of, for example, 0.1 to 1 or 0.2 to 0.5 vvm. If appropriate, a slight over pressure of 0.1 to 1.5 bar may be applied in the process.

According to one embodiment of the process according to the present invention the assimilable carbon source may be glucose, glycerin, glucose, maltose, maltodextrin, fructose, galactose, mannose, xylose, sucrose, arabinose, lactose, raffinose and combinations thereof.

In a preferred embodiment the assimilable carbon source is glucose, sucrose, xylose, arabinose, glycerol or combinations thereof. Preferred carbon sources are glucose, sucrose, glucose and sucrose, glucose and xylose and/or glucose, arabinose and xylose. According to one embodiment of the process according to the present invention the assimilable carbon source may be sucrose, glycerin and/or glucose.

The initial concentration of the assimilable carbon source, preferably the initial concentration is, preferably, adjusted to a value in a range of 5 to 250 g/l, preferably 50 to 200 g/l and more preferably 125 to 150 g/l, most preferably about 140 g/l and may be maintained in said range during cultivation. The pH of the reaction medium may be controlled by addition of suitable bases as for example, gaseous ammonia, $NH_4OH$, $NH_4HCO_3$, $(NH_4)_2COO_3$, $NaOH$, $Na_2CO_3$, $NaHCO_3$, $KOH$, $K_2CO_3$, $KHCO_3$, $Mg(OH)_2$, $MgCO_3$, $Mg(HCO_3)_2$, $Ca(OH)_2$, $CaCO_3$, $Ca(HCO_3)_2$, $CaO$, $CH_6N_2O_2$, $C_2H_7N$ and/or mixtures thereof.

Another embodiment of the invention is a process for fermentative production of alanine, pyruvate, succinate, aspartate, malate, lactate, valine and/or leucine, preferably succinate or alanine, more preferably alanine, most preferably L-alanine comprising the steps of
I) growing the microorganism according to the invention as defined above in a fermenter and
II) recovering alanine, pyruvate, succinate, aspartate, malate, lactate, valine and/or leucine, preferably succinate or alanine, more preferably alanine, most preferably L-alanine from the fermentation broth obtained in I).

The fermentation step I) according to the present invention can, for example, be performed in stirred fermenters, bubble columns and loop reactors. A comprehensive overview of the possible method types including stirrer types and geometric designs can be found in Chmiel: "Bioprozesstechnik: Einführung in die Bioverfahrenstechnik", Volume 1. In the process according to the present invention, typical variants available are the following variants known to those skilled in the art or explained, for example, in Chmiel, Hammes and Bailey: "Biochemica/Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

Particularly preferred conditions for producing alanine, pyruvate, succinate, aspartate, malate, lactate, valine and/or leucine, preferably succinate or alanine, more preferably alanine, most preferably L-alanine in process step I) are:
Assimilable carbon source: glucose
Temperature: 30 to 45° C.
pH: 6.0 to 7.0
Microaerobic conditions In process step II) the product is recovered from the fermentation broth obtained in process step I).

Usually, the recovery process comprises the step of separating the recombinant microorganisms from the fermentation broth as the so called "biomass". Processes for removing the biomass are known to those skilled in the art, and comprise filtration, sedimentation, flotation or combinations thereof. Consequently, the biomass can be removed, for example, with centrifuges, separators, decanters, filters or in a flotation apparatus. For maximum recovery of the product of value, washing of the biomass is often advisable, for example in the form of a diafiltration. The selection of the method is dependent upon the biomass content in the fermentation broth and the properties of the biomass, and also the interaction of the biomass with the organic compound (e. the product of value). In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The recovery process may further comprise additional purification steps in which the fermentation product is further purified. If, however, the fermentation product is converted into a secondary organic product by chemical reactions, a further purification of the fermentation product might, depending on the kind of reaction and the reaction conditions, not necessarily be required. For the purification of the fermentation product obtained in process step II) methods known to the person skilled in the art can be used, as for example crystallization, filtration, electrodialysis and chromatography. The resulting solution may be further purified by means of ion exchange chromatography in order to remove undesired residual ions.

Definitions

It is to be understood that this invention is not limited to the particular methodology or protocols. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth. The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list and also includes any combination of members of that list. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. For clarity, certain terms used in the specification are defined and used as follows:

Coding region: As used herein the term "coding region" when used in reference to a structural gene refers to the nucleotide sequences which encode the amino acids found in the nascent polypeptide as a result of translation of a mRNA molecule. The coding region is bounded, in eukaryotes, on the 5'-side by the nucleotide triplet "ATG" which encodes the initiator methionine, prokaryotes also use the triplets "GTG" and "TTG" as startcodon. On the 3'-side it is bounded by one of the three triplets which specify stop codons (i.e., TAA, TAG, TGA). In addition a gene may include sequences located on both the 5'- and 3'-end of the sequences which are present on the RNA transcript. These sequences are referred to as "flanking" sequences or regions (these flanking sequences are located 5' or 3' to the non-translated sequences present on the mRNA transcript). The 5'-flanking region may contain regulatory sequences such as promoters and enhancers which control or influence the transcription of the gene. The 3'-flanking region may contain sequences which direct the termination of transcription, post-transcriptional cleavage and polyadenylation.

Complementary: "Complementary" or "complementarity" refers to two nucleotide sequences which comprise antiparallel nucleotide sequences capable of pairing with one another (by the base-pairing rules) upon formation of hydrogen bonds between the complementary base residues in the antiparallel nucleotide sequences. For example, the sequence 5'-AGT-3' is complementary to the sequence 5'-ACT-3'. Complementarity can be "partial" or "total." "Partial" complementarity is where one or more nucleic acid bases are not matched according to the base pairing rules. "Total" or "complete" complementarity between nucleic acid molecules is where each and every nucleic acid base is matched with another base under the base pairing rules. The degree of complementarity between nucleic acid molecule strands has significant effects on the efficiency and strength of hybridization between nucleic acid molecule strands. A "complement" of a nucleic acid sequence as used herein refers to a nucleotide sequence whose nucleic acid molecules show total complementarity to the nucleic acid molecules of the nucleic acid sequence.

Endogenous: An "endogenous" nucleotide sequence refers to a nucleotide sequence, which is present in the genome of a wild type microorganism.

Enhanced expression: "enhance" or "increase" the expression of a nucleic acid molecule in a microorganism are used equivalently herein and mean that the level of expression of a nucleic acid molecule in a microorganism is higher compared to a reference microorganism, for example a wild type. The terms "enhanced" or "increased" as used herein mean herein higher, preferably significantly higher expression of the nucleic acid molecule to be expressed. As used herein, an "enhancement" or "increase" of the level of an agent such as a protein, mRNA or RNA means that the level is increased relative to a substantially identical microorganism grown under substantially identical conditions. As used herein, "enhancement" or "increase" of the level of an agent, such as for example a preRNA, mRNA, rRNA, tRNA, expressed by the target gene and/or of the protein product encoded by it, means that the level is increased 50% or more, for example 100% or more, preferably 200% or more, preferably 5 fold or more, even more preferably 10 fold or more, preferably 20 fold or more for example 50 fold relative to a suitable reference microorganism. The enhancement or increase can be determined by methods with which the skilled worker is familiar. Thus, the enhancement or increase of the nucleic acid or protein quantity can be determined for example by an immunological detection of the protein. Moreover, techniques such as protein assay, fluorescence, Northern hybridization, nuclease protection assay, reverse transcription (quantitative RT-PCR), ELISA (enzyme-linked immunosorbent assay), Western blotting, radioimmunoassay (RIA) or other immunoassays and fluorescence-activated cell analysis (FACS) can be employed to measure a specific protein or RNA in a microorganism. Depending on the type of the induced protein product, its activity or the effect on the phenotype of the microorganism may also be determined. Methods for determining the protein quantity are known to the skilled worker. Examples, which may be mentioned, are: the micro-Biuret method (Goa J (1953) Scand J Clin Lab Invest 5:218-222), the Folin-Ciocalteau method (Lowry OH et al. (1951) J Biol Chem 193:265-275) or measuring the absorption of CBB G-250 (Bradford M M (1976) Analyt Biochem 72:248-254).

Expression: "Expression" refers to the biosynthesis of a gene product, preferably to the transcription and/or translation of a nucleotide sequence, for example an endogenous gene or a heterologous gene, in a cell. For example, in the case of a structural gene, expression involves transcription of the structural gene into mRNA and—optionally—the subsequent translation of mRNA into one or more polypeptides. In other cases, expression may refer only to the transcription of the DNA harboring an RNA molecule.

Foreign: The term "foreign" refers to any nucleic acid molecule (e.g., gene sequence) which is introduced into a cell by experimental manipulations and may include sequences found in that cell as long as the introduced sequence contains some modification (e.g., a point mutation, the presence of a selectable marker gene, etc.) and is therefore different relative to the naturally-occurring sequence.

Functional linkage: The term "functional linkage" or "functionally linked" is equivalent to the term "operable linkage" or "operably linked" and is to be understood as meaning, for example, the sequential arrangement of a regulatory element (e.g. a promoter) with a nucleic acid sequence to be expressed and, if appropriate, further regulatory elements (such as e.g., a terminator) in such a way that each of the regulatory elements can fulfill its intended function to allow, modify, facilitate or otherwise influence expression of said nucleic acid sequence. As a synonym the wording "operable linkage" or "operably linked" may be used. The expression may result depending on the arrangement of the nucleic acid sequences in relation to sense or antisense RNA. To this end, direct linkage in the chemical sense is not necessarily required. Genetic control sequences such as, for example, enhancer sequences, can also exert their function on the target sequence from positions which are further away, or indeed from other DNA molecules. Preferred arrangements are those in which the nucleic acid sequence to be expressed recombinantly is positioned behind the sequence acting as promoter, so that the two sequences are linked covalently to each other.

In a preferred embodiment, the nucleic acid sequence to be transcribed is located behind the promoter in such a way that the transcription start is identical with the desired beginning of the chimeric RNA of the invention. Functional linkage, and an expression construct, can be generated by means of customary recombination and cloning techniques as described (e.g., in Maniatis T, Fritsch E F and Sambrook J (1989) Molecular Cloning: A Laboratory Manual, 2nd Ed., Cold Spring Harbor Laboratory, Cold Spring Harbor (N.Y.); Silhavy et al. (1984) Experiments with Gene Fusions, Cold Spring Harbor Laboratory, Cold Spring Harbor (N.Y.); Ausubel et al. (1987) Current Protocols in Molecular Biology, Greene Publishing Assoc. and Wiley Interscience; Gelvin et al. (Eds) (1990) Plant Molecular Biology Manual; Kluwer Academic Publisher, Dordrecht, The Netherlands). However, further sequences, which, for example, act as a linker with specific cleavage sites for restriction enzymes, or as a signal peptide, may also be positioned between the two sequences. The insertion of sequences may also lead to the expression of fusion proteins. Preferably, the expression construct, consisting of a linkage of a regulatory region for example a promoter and nucleic acid sequence to be expressed, can exist in a vector-integrated form or can be inserted into the genome, for example by transformation.

Gene: The term "gene" refers to a region operably linked to appropriate regulatory sequences capable of regulating the expression of the gene product (e.g., a polypeptide or a functional RNA) in some manner. A gene includes untranslated regulatory regions of DNA (e.g., promoters, enhancers, repressors, etc.) preceding (up-stream) and following (downstream) the coding region (open reading frame, ORF). The term "structural gene" as used herein is intended to mean a DNA sequence that is transcribed into mRNA which is then translated into a sequence of amino acids characteristic of a specific polypeptide.

Genome and genomic DNA: The terms "genome" or "genomic DNA" is referring to the heritable genetic information of a host organism. Said genomic DNA comprises the DNA of the nucleoid but also the DNA of the self replicating plasmid.

Heterologous: The term "heterologous" with respect to a nucleic acid molecule or DNA refers to a nucleic acid molecule which is operably linked to, or is manipulated to become operably linked to, a second nucleic acid molecule to which it is not operably linked in nature, or to which it is operably linked at a different location in nature. A heterologous expression construct comprising a nucleic acid molecule and one or more regulatory nucleic acid molecule (such as a promoter or a transcription termination signal) linked thereto for example is a constructs originating by experimental manipulations in which either a) said nucleic acid molecule, or b) said regulatory nucleic acid molecule or c) both (i.e. (a) and (b)) is not located in its natural (native) genetic environment or has been modified by experimental manipulations, an example of a modification being a substitution, addition, deletion, inversion or insertion of one or more nucleotide residues. Natural genetic environment refers to the natural genomic locus in the organism of origin, or to the presence in a genomic library. In the case of a genomic library, the natural genetic environment of the sequence of the nucleic acid molecule is preferably retained, at least in part. The environment flanks the nucleic acid sequence at least at one side and has a sequence of at least 50 bp, preferably at least 500 bp, especially preferably at least 1,000 bp, very especially preferably at least 5,000 bp, in length. A naturally occurring expression construct—for example the naturally occurring combination of a promoter with the corresponding gene—becomes a transgenic expression construct when it is modified by non-natural, synthetic "artificial" methods such as, for example, mutagenization. Such methods have been described (U.S. Pat. No. 5,565,350; WO 00/15815). For example a protein encoding nucleic acid molecule operably linked to a promoter, which is not the native promoter of this molecule, is considered to be heterologous with respect to the promoter. Preferably, heterologous DNA is not endogenous to or not naturally associated with the cell into which it is introduced, but has been obtained from another cell or has been synthesized. Heterologous DNA also includes an endogenous DNA sequence, which contains some modification, non-naturally occurring, multiple copies of an endogenous DNA sequence, or a DNA sequence which is not naturally associated with another DNA sequence physically linked thereto. Generally, although not necessarily, heterologous DNA encodes RNA or proteins that are not normally produced by the cell into which it is expressed.

Hybridization: The term "hybridization" as used herein includes "any process by which a strand of nucleic acid molecule joins with a complementary strand through base pairing." (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules. As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% \text{ G+C})$, when a nucleic acid molecule is in aqueous solution at 1 M NaCl [see e.g., Anderson and Young, Quantitative Filter Hybridization, in Nucleic Acid Hybridization (1985)]. Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6. Suitable hybridization conditions are for example hybridizing under conditions equivalent to hybridization in 7% sodium dodecyl sulfate (SDS), 0.5 M NaPO4, 1 mM EDTA at 50° C. with washing in 2×SSC, 0.1% SDS at 50° C. (low stringency) to a nucleic acid molecule comprising at least 50, preferably at least 100, more preferably at least 150, even more preferably at least 200, most preferably at least 250 consecutive nucleotides of the complement of a sequence. Other suitable hybridizing conditions are hybridization in 7% sodium dodecyl sulfate (SDS), 0.5 M NaPO4, 1 mM EDTA at 50° C. with washing in 1×SSC, 0.1% SDS at 50° C. (medium stringency) or 65° C. (high stringency) to a nucleic acid molecule comprising at least 50, preferably at least 100, more preferably at least 150, even more preferably at least 200, most preferably at least 250 consecutive nucleotides of a complement of a sequence. Other suitable hybridization conditions are hybridization in 7% sodium dodecyl sulfate (SDS), 0.5 M NaPO4, 1 mM EDTA at 50° C. with washing in 0.1×SSC, 0.1% SDS at 65° C. (very high stringency) to a nucleic acid molecule comprising at least 50, preferably at least 100, more preferably at least 150, even more preferably at least 200, most preferably at least 250 consecutive nucleotides of a complement of a sequence.

"Identity": "Identity" when used in respect to the comparison of two or more nucleic acid or amino acid molecules means that the sequences of said molecules share a certain degree of sequence similarity, the sequences being partially identical.

To determine the percentage identity (homology is herein used interchangeably if referring to nucleic acid sequences) of two amino acid sequences or of two nucleic acid molecules, the sequences are written one underneath the other for an optimal comparison (for example gaps may be inserted into the sequence of a protein or of a nucleic acid in order to generate an optimal alignment with the other protein or the other nucleic acid).

The amino acid residues or nucleic acid molecules at the corresponding amino acid positions or nucleotide positions are then compared. If a position in one sequence is occupied by the same amino acid residue or the same nucleic acid molecule as the corresponding position in the other sequence, the molecules are identical at this position. The percentage identity between the two sequences is a function of the number of identical positions shared by the sequences (i.e. % identity=number of identical positions/total number of positions×100). The terms "homology" and "identity" are thus to be considered as synonyms when referring to nucleic acid sequences. When referring to amino acid sequences the term identity refers to identical amino acids at a specific position in a sequence, the term homology refers to homologous amino acids at a specific position in a sequence. Homologous amino acids are amino acids having a similar side chain. Families of amino acid residues having similar side chains have been defined in the art.

A nucleic acid molecule encoding a protein homologous to a protein of the invention can be created by introducing one or more nucleotide substitutions, additions or deletions into a nucleotide sequence such that one or more amino acid substitutions, additions or deletions are introduced into the encoded protein. Mutations can be introduced into one of the sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in a protein of the invention is preferably replaced with another amino acid residue from the same side chain family.

Alternatively, in another embodiment, mutations can be introduced randomly along all or part of a coding sequence, such as by saturation mutagenesis, and the resultant mutants can be screened for the respective activity described herein to identify mutants that retain their activity. Following mutagenesis of one of the sequences of the invention, the encoded protein can be expressed recombinantly and the activity of the protein can be determined using, for example, assays described herein.

For the determination of the percentage identity of two or more amino acids or of two or more nucleotide sequences several computer software programs have been developed. The identity of two or more sequences can be calculated with for example the software fasta, which presently has been used in the version fasta 3 (W. R. Pearson and D. J. Lipman, PNAS 85, 2444(1988); W. R. Pearson, Methods in Enzymology 183, 63 (1990); W. R. Pearson and D. J. Lipman, PNAS 85, 2444 (1988); W. R. Pearson, Enzymology 183, 63 (1990)). Another useful program for the calculation of identities of different sequences is the standard blast program, which is included in the Biomax pedant software (Biomax, Munich, Federal Republic of Germany). This leads unfortunately sometimes to suboptimal results since blast does not always include complete sequences of the subject and the query. Nevertheless as this program is very efficient it can be used for the comparison of a huge number of sequences. The following settings are typically used for such a comparisons of sequences:

-p Program Name [String]; -d Database [String]; default=nr; -i Query File [File In]; default=stdin; -e Expectation value (E) [Real]; default=10.0; -m alignment view options: 0=pairwise; 1=query-anchored showing identities; 2=query-anchored no identities; 3=flat query-anchored, show identities; 4=flat query-anchored, no identities; 5=query-anchored no identities and blunt ends; 6=flat query-anchored, no identities and blunt ends; 7=XML Blast output; 8=tabular; 9 tabular with comment lines [Integer]; default=0; -o BLAST report Output File [File Out] Optional; default=stdout; -F Filter query sequence (DUST with blastn, SEG with others) [String]; default=T; -G Cost to open a gap (zero invokes default behavior) [Integer]; default=0; -E Cost to extend a gap (zero invokes default behavior) [Integer]; default=0; -X X dropoff value for gapped alignment (in bits) (zero invokes default behavior); blastn 30, megablast 20, tblastx 0, all others 15 [Integer]; default=0; -I Show GI's in deflines [T/F]; default=F; -q Penalty for a nucleotide mismatch (blastn only) [Integer]; default=−3; -r Reward for a nucleotide match (blastn only) [Integer]; default=1; -v Number of database sequences to show one-line descriptions for (V) [Integer]; default=500; -b Number of database sequence to show alignments for (B) [Integer]; default=250; -f Threshold for extending hits, default if zero; blastp 11, blastn 0, blastx 12, tblastn 13; tblastx 13, megablast 0 [Integer]; default=0; -g Perfom gapped alignment (not available with tblastx) [T/F]; default=T; -Q Query Genetic code to use [Integer]; default=1; -D DB Genetic code (for tblast [nx] only) [Integer]; default=1; -a Number of processors to use [Integer]; default=1; -O SeqAlign file [File Out] Optional; -J Believe the query defline [T/F]; default=F; -M Matrix [String]; default=BLOSUM62; -W Word size, default if zero (blastn 11, megablast 28, all others 3) [Integer]; default=0; -z Effective length of the database (use zero for the real size) [Real]; default=0; -K Number of best hits from a region to keep (off by default, if used a value of 100 is recommended) [Integer]; default=0; -P 0 for multipie hit, 1 for single hit [Integer]; default=0; -Y Effective length of the search space (use zero for the real size) [Real]; default=0; -S Query strands to search against database (for blast[nx], and tblastx); 3 is both, 1 is top, 2 is bottom [Integer]; default=3; -T Produce HTML output [T/F]; default=F; -I Restrict search of database to list of GI's [String] Optional; -U Use lower case filtering of FASTA sequence [T/F] Optional; default=F; -y X dropoff value for ungapped extensions in bits (0.0 invokes default behavior); blastn 20, megablast 10, all others 7 [Real]; default=0.0; -Z X dropoff value for final gapped alignment in bits (0.0 invokes default behavior); blastn/megablast 50, tblastx 0, all others 25 [Integer]; default=0; -R PSI-TBLASTN checkpoint file [File In] Optional; -n MegaBlast search [T/F]; default=F; -L Location on query sequence [String] Optional; -A Multiple Hits window size, default if zero (blastn/megablast 0, all others 40 [Integer]; default=0; -w Frame shift penalty (OOF algorithm for blastx) [Integer]; default=0; -t Length of the largest intron allowed in tblastn for linking HSPs (0 disables linking) [Integer]; default=0.

Results of high quality are reached by using the algorithm of Needleman and Wunsch or Smith and Waterman. Therefore programs based on said algorithms are preferred. Advantageously the comparisons of sequences can be done with the program PileUp (J. Mol. Evolution., 25, 351 (1987), Higgins et al., CABIOS 5, 151 (1989)) or preferably with the programs "Gap" and "Needle", which are both based on the algorithms of Needleman and Wunsch (J. Mol. Biol. 48; 443 (1970)), and "BestFit", which is based on the algorithm of Smith and Waterman (Adv. Appl. Math. 2; 482 (1981)). "Gap" and "BestFit" are part of the GCG software-package (Genetics Computer Group, 575 Science Drive, Madison, Wis., USA 53711 (1991); Altschul et al., (Nucleic Acids Res. 25, 3389 (1997)), "Needle" is part of the The European Molecular Biology Open Software Suite (EMBOSS) (Trends in Genetics 16 (6), 276 (2000)). Therefore preferably the calculations to determine the percentages of sequence identity are done with the programs "Gap" or "Needle" over the whole range of the sequences. The following standard adjustments for the comparison of nucleic acid sequences were used for "Needle": matrix: EDNAFULL, Gap_penalty: 10.0, Extend_penalty: 0.5. The following standard adjustments for the comparison of nucleic acid sequences were used for "Gap": gap weight: 50, length weight: 3, average match: 10.000, average mismatch: 0.000.

For example a sequence, which is said to have 80% identity with sequence SEQ ID NO: 1 at the nucleic acid level is understood as meaning a sequence which, upon comparison with the sequence represented by SEQ ID NO: 1 by the above program "Needle" with the above parameter set, has a 80% identity. Preferably the identity is calculated on the complete length of the query sequence, for example SEQ ID NO: 1.

Isolated: The term "isolated" as used herein means that a material has been removed by the hand of man and exists apart from its original, native environment and is therefore not a product of nature. An isolated material or molecule (such as a DNA molecule or enzyme) may exist in a purified form or may exist in a non-native environment such as, for example, in a transgenic host cell. For example, a naturally occurring nucleic acid molecule or polypeptide present in a living cell is not isolated, but the same nucleic acid molecule or polypeptide, separated from some or all of the coexisting materials in the natural system, is isolated. Such nucleic acid molecules can be part of a vector and/or such nucleic acid molecules or polypeptides could be part of a composition, and would be isolated in that such a vector or composition is not part of its original environment. Preferably, the term "isolated" when used in relation to a nucleic acid molecule, as in "an isolated nucleic acid sequence" refers to a nucleic acid sequence that is identified and separated from at least one contaminant nucleic acid molecule with which it is ordinarily associated in its natural source. Isolated nucleic acid molecule is nucleic acid molecule present in a form or setting that is different from that in which it is found in nature. In contrast, non-isolated nucleic acid molecules are nucleic acid molecules such as DNA and RNA, which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs, which encode a multitude of proteins. However, an isolated nucleic acid sequence comprising for example SEQ ID NO: 1 includes, by way of example, such nucleic acid sequences in cells which ordinarily contain SEQ ID NO: 1 where the nucleic acid sequence is in a genomic or plasmid location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

Non-coding: The term "non-coding" refers to sequences of nucleic acid molecules that do not encode part or all of an expressed protein. Non-coding sequences include but are not limited enhancers, promoter regions, 3' untranslated regions, and 5' untranslated regions.

Nucleic acids and nucleotides: The terms "nucleic acids" and "Nucleotides" refer to naturally occurring or synthetic or artificial nucleic acid or nucleotides. The terms "nucleic acids" and "nucleotides" comprise deoxyribonucleotides or ribonucleotides or any nucleotide analogue and polymers or hybrids thereof in either single- or double-stranded, sense or antisense form. Unless otherwise indicated, a particular nucleic acid sequence also implicitly encompasses conservatively modified variants thereof (e.g., degenerate codon substitutions) and complementary sequences, as well as the sequence explicitly indicated. The term "nucleic acid" is used inter-changeably herein with "gene", "cDNA, "mRNA", "oligonucleotide," and "nucleic acid molecule". Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. Short hairpin RNAs (shRNAs) also can comprise non-natural elements such as non-natural bases, e.g., ionosin and xanthine, non-natural sugars, e.g., 2'-methoxy ribose, or non-natural phosphodiester linkages, e.g., methylphosphonates, phosphorothioates and peptides.

Nucleic acid sequence: The phrase "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. In one embodiment, a nucleic acid can be a "probe" which is a relatively short nucleic acid, usually less than 100 nucleotides in length. Often a nucleic acid probe is from about 50 nucleotides in length to about 10 nucleotides in length. A "target region" of a nucleic acid is a portion of a nucleic acid that is identified to be of interest. A "coding region" of a nucleic acid is the portion of the nucleic acid, which is transcribed and translated in a sequence-specific manner to produce into a particular polypeptide or protein when placed under the control of appropriate regulatory sequences. The coding region is said to encode such a polypeptide or protein.

Oligonucleotide: The term "oligonucleotide" refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

Overhang: An "overhang" is a relatively short single-stranded nucleotide sequence on the 5'- or 3'-hydroxyl end of a double-stranded oligonucleotide molecule (also referred to as an "extension," "protruding end," or "sticky end").

Polypeptide: The terms "polypeptide", "peptide", "oligopeptide", "polypeptide", "gene product", "expression product" and "protein" are used interchangeably herein to refer to a polymer or oligomer of consecutive amino acid residues.

Promoter: The terms "promoter", or "promoter sequence" are equivalents and as used herein, refer to a DNA sequence which when operably linked to a nucleotide sequence of interest is capable of controlling the transcription of the nucleotide sequence of interest into RNA. A promoter is located 5' (i.e., upstream), proximal to the transcriptional start site of a nucleotide sequence of interest whose transcription into mRNA it controls, and provides a site for specific binding by RNA polymerase and other transcription factors for initiation of transcription. The promoter does not comprise coding regions or 5' untranslated regions. The promoter may for example be heterologous or homologous to the respective cell. A nucleic acid molecule sequence is "heterologous to" an organism or a second nucleic acid molecule sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is not naturally associated with the promoter (e.g. a genetically engineered coding sequence or an allele from a different ecotype or variety). Suitable promoters can be derived from genes of the host cells where expression should occur or from pathogens for this host.

Purified: As used herein, the term "purified" refers to molecules, either nucleic or amino acid sequences that are removed from their natural environment, isolated or separated. "Substantially purified" molecules are at least 60% free, preferably at least 75% free, and more preferably at least 90% free from other components with which they are naturally associated. A purified nucleic acid sequence may be an isolated nucleic acid sequence.

Recombinant: The term "recombinant" with respect to nucleic acid molecules refers to nucleic acid molecules produced by recombinant DNA techniques. The term also comprises nucleic acid molecules which as such does not exist in nature but are modified, changed, mutated or otherwise manipulated by man. Preferably, a "recombinant nucleic acid molecule" is a non-naturally occurring nucleic acid molecule that differs in sequence from a naturally occurring nucleic acid molecule by at least one nucleic acid. A "recombinant nucleic acid molecule" may also comprise a "recombinant construct" which comprises, preferably operably linked, a sequence of nucleic acid molecules not naturally occurring in that order. Preferred methods for producing said recombinant nucleic acid molecule may comprise cloning techniques, directed or non-directed mutagenesis, synthesis or recombination techniques.

Significant increase: An increase for example in enzymatic activity, gene expression, productivity or yield of a certain product, that is larger than the margin of error inherent in the measurement technique, preferably an increase by about 10% or 25% preferably by 50% or 75%, more preferably 2-fold or-5 fold or greater of the activity, expression, productivity or yield of the control enzyme or expression in the control cell, productivity or yield of the control cell, even more preferably an increase by about 10-fold or greater.

Significant decrease: A decrease for example in enzymatic activity, gene expression, productivity or yield of a certain product, that is larger than the margin of error inherent in the measurement technique, preferably a decrease by at least about 5% or 10%, preferably by at least about 20% or 25%, more preferably by at least about 50% or 75%, even more preferably by at least about 80% or 85%, most preferably by at least about 90%, 95%, 97%, 98% or 99%.

Substantially complementary: In its broadest sense, the term "substantially complementary", when used herein with respect to a nucleotide sequence in relation to a reference or target nucleotide sequence, means a nucleotide sequence having a percentage of identity between the substantially complementary nucleotide sequence and the exact complementary sequence of said reference or target nucleotide sequence of at least 60%, more desirably at least 70%, more desirably at least 80% or 85%, preferably at least 90%, more preferably at least 93%, still more preferably at least 95% or 96%, yet still more preferably at least 97% or 98%, yet still more preferably at least 99% or most preferably 100% (the latter being equivalent to the term "identical" in this context). Preferably identity is assessed over a length of at least 19 nucleotides, preferably at least 50 nucleotides, more preferably the entire length of the nucleic acid sequence to said reference sequence (if not specified otherwise below). Sequence comparisons are carried out using default GAP analysis with the University of Wisconsin GCG, SEQWEB application of GAP, based on the algorithm of Needleman and Wunsch (Needleman and Wunsch (1970) J Mol. Biol. 48: 443-453; as defined above). A nucleotide sequence "substantially complementary" to a reference nucleotide sequence hybridizes to the reference nucleotide sequence under low stringency conditions, preferably medium stringency conditions, most preferably high stringency conditions (as defined above).

Transgene: The term "transgene" as used herein refers to any nucleic acid sequence, which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence, which is naturally found in the cell into which it is introduced so long as it does not contain some modification (e.g., a point mutation, the presence of a selectable marker gene, etc.) relative to the naturally-occurring sequence.

Transgenic: The term transgenic when referring to an organism means transformed, preferably stably transformed, with a recombinant DNA molecule that preferably comprises a suitable promoter operatively linked to a DNA sequence of interest.

Vector: As used herein, the term "vector" refers to a nucleic acid molecule capable of transporting another nucleic acid molecule to which it has been linked. One type of vector is a genomic integrated vector, or "integrated vector", which can become integrated into the genomic DNA of the host cell. Another type of vector is an episomal vector, i.e., a plasmid or a nucleic acid molecule capable of extra-chromosomal replication. Vectors capable of directing the expression of genes to which they are operatively linked are referred to herein as "expression vectors". In the present specification, "plasmid" and "vector" are used interchangeably unless otherwise clear from the context.

Wild type: The term "wild type", "natural" or "natural origin" means with respect to an organism that said organism is not changed, mutated, or otherwise manipulated by man. With respect to a polypeptide or nucleic acid sequence, that the polypeptide or nucleic acid sequence is naturally occurring or available in at least one naturally occurring organism which is not changed, mutated, or otherwise manipulated by man.

A wild type of a microorganism refers to a microorganism whose genome is present in a state as before the introduction of a genetic modification of a certain gene. The genetic modification may be e.g. a deletion of a gene or a part thereof or a point mutation or the introduction of a gene.

The terms "production" or "productivity" are art-recognized and include the concentration of the fermentation product (for example, alanine) formed within a given time and a given fermentation volume (e.g., kg product per hour per liter). The term "efficiency of production" includes the time required for a particular level of production to be achieved (for example, how long it takes for the cell to attain a particular rate of output of a fine chemical).

The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules or of useful recovered molecules of that compound in a given amount of culture over a given amount of time is increased.

The term "recombinant microorganism" includes microorganisms which have been genetically modified such that they exhibit an altered or different genotype and/or phenotype (e.g., when the genetic modification affects coding nucleic acid sequences of the microorganism) as compared to the wild type microorganism from which it was derived. A recombinant microorganism comprises at least one recombinant DNA molecule.

The term "recombinant" with respect to DNA refers to DNA molecules produced by man using recombinant DNA techniques. The term comprises DNA molecules which as such do not exist in nature or do not exist in the organism from which the DNA is derived, but are modified, changed, mutated or otherwise manipulated by man. Preferably, a "recombinant DNA molecule" is a non-naturally occurring nucleic acid molecule that differs in sequence from a naturally occurring nucleic acid molecule by at least one nucleic acid. A "recombinant DNA molecule" may also comprise a "recombinant construct" which comprises, preferably operably linked, a sequence of nucleic acid molecules not naturally occurring in that order. Preferred methods for producing said recombinant DNA molecule may comprise cloning techniques, directed or non-directed mutagenesis, gene synthesis or recombination techniques.

The term "directed evolution" is used synonymously with the term "metabolic evolution" herein and involves applying a selection pressure that favors the growth of mutants with the traits of interest. The selection pressure can be based on different culture conditions, ATP and growth coupled selection and redox related selection. The selection pressure can be carried out with batch fermentation with serial transferring inoculation or continuous culture with the same pressure.

An example of such a recombinant DNA is a plasmid into which a heterologous DNA-sequence has been inserted or a gene or promoter which has been mutated compared to gene or promoter from which the recombinant DNA derived. The mutation may be introduced by means of directed mutagenesis technologies known in the art or by random mutagenesis technologies such as chemical, UV light or x-ray mutagenesis or directed evolution technologies.

The term "expression" or "gene expression" means the transcription of a specific gene(s) or specific genetic vector construct. The term "expression" or "gene expression" in particular means the transcription of gene(s) or genetic vector construct into mRNA. The process includes transcription of DNA and may include processing of the resulting RNA-product. The term "expression" or "gene expression" may also include the translation of the mRNA and therewith the synthesis of the encoded protein, i.e. protein expression.

FIG. 1

Alanine formation in a batch fermentation of *E. coli* QZ20 with empty plasmid control and *E. coli* QZ20/pACYC-asd in 500 mL AM 1 medium with 120 g/L glucose. The fermentation was controlled at 37 C, 400 rpm, at pH 6.8 with 5 N NH4OH without aeration.

FIG. 2

Alanine formation in a batch fermentation of *E. coli* QZ20 with empty plasmid control and *E. coli* QZ20/pACYC-gdhA in 500 mL AM 1 medium with 120 g/L glucose. The fermentation was controlled at 37 C, 400 rpm, at pH 6.8 with 5 N $NH_4OH$ without aeration.

EXAMPLES

Chemicals and Common Methods

Unless indicated otherwise, cloning procedures carried out for the purposes of the present invention including restriction digest, agarose gel electrophoresis, purification of nucleic acids, ligation of nucleic acids, transformation, selection and cultivation of bacterial cells are performed as described (Sambrook et al., 1989). Sequence analyses of recombinant DNA are performed with a laser fluorescence DNA sequencer (Applied Biosystems, Foster City, Calif., USA) using the Sanger technology (Sanger et al., 1977). Unless described otherwise, chemicals and reagents are obtained from Sigma Aldrich (Sigma Aldrich, St. Louis, USA), from Promega (Madison, Wis., USA), Duchefa (Haarlem, The Netherlands) or Invitrogen (Carlsbad, Calif., USA). Restriction endonucleases are from New England Biolabs (Ipswich, Mass., USA) or Roche Diagnostics GmbH (Penzberg, Germany). Oligonucleotides are synthesized by Eurofins MWG Operon (Ebersberg, Germany).

Example 1

*E. coli* W (LU17032) was engineered for L-alanine production by inactivation of the ackA, adhE, frdABCD and pflB ORFs and replacement of the ldhA ORF by a codon-optimized variant of the alaD gene (alaD-gstear).

The ackA, adhE, frdABCD and pflB ORFs were inactivated by insertion of an FRT-flanked kanamycin resistance cassette, followed by removal of the antibiotic resistance cassette by FLP recombination.

The IdhA gene was replaced by alaD-gstear and a downstream FRT-flanked zeocin resistance cassette, which was finally removed by FLP recombination.

The procedure has been described previously for example in WO2015/044818 which is hereby incorporated by reference.

Disruption of ackA has been described previously for example in Causey et al (2004), PNAS, 101 (8) pages 2235-2240.

Further, in said strain comprising an inactivated ackA, adhE, frdABCD, pflB and IdhA and an introduced alaD activity, the activity of the genes lpd, zipA and ygaW have been increased as described previously in WO2015/044818 and the activity of the alaD has been further enhanced by mutating the promoter controlling said gene as described previously in WO2015/044818.

Bacterial Culture

E. coli W (LU17032) was cultured in Luria-Bertani (LB) liquid medium or on Luria-Bertani solid medium. Occasionally, clones were passaged over M9 minimal agar containing 10 mM Sucrose to confirm W strain identity. Antibiotics were added to the liquid and solid media as appropriate, to final concentrations of 15 µg/ml (kanamycin, chloramphenicol), 25 µg/ml (zeocin) or 3 µg/ml (tetracyclin).

Red/ET recombination

Red/ET recombination was performed using standard protocols of Gene Bridges GmbH (www.genebridges.com). Briefly, Red/ET-proficient E. coli W was aerobically grown at 30° C. to an OD600 nm of ~0.3. Expression of red genes was induced by adding 50 µl of 10% (w/v) L-arabinose, followed by a temperature increase to 37° C. Arabinose was omitted from uninduced control cultures. After 35 min of incubation at 37° C. the cells were washed twice with ice cold 10% (v/v) glycerol and electroporated with 500 ng of PCR product at 1.35 kV, 10 µF, 600Ω. The cells were then resuspended in 1 ml ice-cold LB medium and aerobically grown at 37° C. for approximately 1.5 h. Cultures were then plated on LB agar containing 15 µg/ml kanamycin (knockouts) or 25 µg/ml zeocin (knockin).

FLP Recombination

Flanking FRT sites allowed removal of antibiotic resistance markers by FLP recombination following modification of the E. coli chromosome. FLP recombination leaves a single FRT site (34 bp) as well as short flanking sequences (approx. 20 bp each) which are used as primer binding sites in the amplification of the cassettes.

To perform FLP recombination, plasmid 708-FLPe (Tab. 1) encoding FLP recombinase was introduced into the Red/ET recombinants by electroporation. KanR CmR or ZeoR CmR transformants were used to inoculate 0.2 ml LB cultures, which were incubated at 30° C. for 3 h. FLP activity was then induced by a temperature shift to 37° C., followed by a three-hour incubation at 37° C. Single colonies obtained from these cultures were subsequently screened for a CmS and KanS or ZeoS phenotype.

DNA Preparation and Analysis

E. coli genomic DNA (gDNA) was isolated from overnight cultures with the Gentra Puregene Yeast/Bact. Kit B (Qiagen, Hilden, Germany). PCR products harbouring knockout or knockin cassettes were amplified from template plasmids with PRECISOR high-fidelity DNA polymerase (BioCat, Heidelberg) and analytical PCR reactions were performed with the PCR Extender System (5PRIME GmbH, Hamburg, Germany), according to the manufacturer's recommendations. PCR amplicons were purified using the GeneJET PCR Purification Kit or the GeneJET Gel Extraction Kit (Fermentas, St. Leon-Rot, Germany) and sequencing was performed by GATC BioTech (Konstanz, Germany) or BioSpring (Frankfurt am Main, Germany).

TABLE 1

Plasmids and primers

| plasmids | Relevant characteristics/oligo sequences (5' → 3') | Source |
| --- | --- | --- |
| pRed/ET | red expression plasmid, pSC101-based, Tc$^R$ | Gene Bridges |
| 708-FLPe | FLP recombinase expression plasmid, pSC101-based, Cm$^R$ | Gene Bridges |

| primers (BioSpring) | SEQ ID NO |
| --- | --- |
| pACYC-asd-F | 35 |
| pACYC-asd-R | 36 |
| pACYC-gdhA-F | 40 |
| pACYC-gdhA-R | 41 |

Example 2 HPLC Detection and Quantification of Alanine

The following HPLC method for the alanine detection in the cell culture media was used:

Column: Aminex HPX-87C column (Bio-Rad), 300×7.8 mm, i.d. particle size 9 µm

Mobile phase: Ca(NO3)$_2$ at 0.1 mol/L 90%, Acetonitrile 10%

Flow rate: 0.6 mL/min

Column temperature: 60° C.

Detection: Refractive index detector

Under above method, major estimated components in the cell culture sample matrix can be well separated from alanine, without interfering alanine's quantitation.

The amount of the alanine in the sample was determined by external standard calibration method. Standard samples containing alanine from 0.5 to 10.0 g/L were injected and the peak areas were used for calibration. Linear regression coefficient of the calibration curve was 0.9995.

Samples are injected once at 20 µL. Peak areas are used to calculate the amount presenting in the sample by Waters LC Millenium software.

Example 3 HPLC Detection and Quantification of of Glucose, Succinate, Lactate, Formate, Acetate and Ethanol HPLC Method Used Column: Aminex HPX-87H column (Bio-Rad), 300×7.8 mm, i.d. particle size 9 µm Mobile phase: H2SO4 4 mM Flow rate: 0.4 mL/min Column temperature: 45° C.

Detection: Refractive index detector

The amount of the analytes was determined by external standard calibration method. Standard samples containing glucose from 0.1 to 38.0 g/L, succinate, lactate, formate, acetate and ethanol from 0.05 to 10.0 g/L were injected and the peak areas were used for calibration. Linear regression coefficients for all six calibration curves were better than 0.999.

Samples are injected once at 20 µL. Peak areas are used to calculate the amount presenting in the sample by Waters LC Millenium software.

Example 4 Effect of the Increased Expression of the Asd Gene on Alanine Productivity An additional copy of the asd gene (SEQ ID NO: 25) was introduced into the pACYC184 plasmid under the control of an IPTG-inducible Ptrc promoter. The vector, designated as pACYC-asd (SEQ ID NO: 34), was constructed via commercial InFusion cloning technology (Clontech, Mountain View, Calif., USA). The pACYC184 vector (NEB) was linearized with HindIII and SaiI restriction endonucleases (NEB). The generated vector backbone was purified by agarose gel extraction. The asd gene was PCR amplified from wild-type E. coli W genomic DNA with primers asd-pACYC_F (SEQ ID NO: 35) and asd-pACYC_R (SEQ ID NO: 36). The primers contained additional 15 bp homologous overhangs to the vector backbone and a double-stranded DNA fragment with the Ptrc promoter that was synthesized by IDT. The amplified asd gene, the upstream Ptrc promoter and the pACYC184 vector backbone were cloned together according to the InFusion cloning manual. The resulting pACYC-asd vector was transformed into E. coli via electroporation and selected for on LB chloramphenicol plates. Positive constructs were confirmed by DNA sequencing.

The effect of asd overexpression on alanine productivity was tested by comparative cultivation of E. coli with an empty control pACYC vector and E. coli harbouring the asd overexpression plasmid pACYC-asd (SEQ ID NO: 34). Precultures were grown in shake flasks with LB medium, 20% filling volume at 37 C and 200 rpm overnight. The fermentation was performed in the DASGIP 1.5 L parallel bioreactor system (Eppendorf) in 500 mL AM 1 medium (2.6 g/L (NH4)2HPO4, 0.87 g/L NH4H2PO4, 0.15 g/L Kill, 0.37 g/L MgSO4 ·7H2O, 15 g/L (NH4)2SO4, 1 mM betaine, 1 ml/L trace metal stock solution). The trace metal stock comprised 1.6 g/L FeCL3 ·6H2O; 0.2 g/L CoCl2 ·6H2O; 0.1 g/L CuCl2 ·2H2O; 0.2 g/L ZnCl2; 0.2 g/L NaMoO4 ·2H2O; 0.05 g/L H3BO3, 0.1 M HCL. 120 g/L Glucose were used as carbon source in the fermentation medium. 25 ug/mL chloramphenicol were added to stably maintain the plasmid. Expression of the asd gene from the Ptrc promoter was induced with 250 uM isopropyl β-D-1-thiogalactopyranoside (IPTG) during the early logarithmic growth phase. Each strain was run in duplicates at 37 C and 400 rpm stirrer speed. 5N NH$_4$OH was used to control the pH to 6.8 and provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for alanine and glucose concentrations.

After 72 h of fermentation time E. coli QZ20 in which the asd gene (SEQ ID NO: 25) was overexpressed from the pACYC-asd plasmid (SEQ ID NO: 34) reached a significantly higher L-alanine titer of 66.58±0.50 g/L compared to the strain harbouring the empty control plasmid with 46.00±1.85 g/L (FIG. 1).

Example 5 Effect of the Increased Expression of the gdhA Gene on Alanine Productivity An additional copy of the gdhA gene (SEQ ID NO: 37) was introduced into the pACYC184 plasmid under the control of an IPTG-inducible Ptrc promoter. The vector, designated as pACYC-gdhA (SEQ ID NO: 39), was constructed via commercial InFusion cloning technology (Clontech, Mountain View, Calif., USA). The pACYC184 vector (NEB) was linearized with HindIII and SaiI restriction endonucleases (NEB). The generated vector backbone was purified by agarose gel extraction. The gdhA gene was PCR amplified from wild-type E. coli W genomic DNA with primers gdhA-pACYC_F (SEQ ID NO: 40) and gdhA-pACYC_R (SEQ ID NO: 41). The primers contained additional 15 bp homologous overhangs to the vector backbone and a double-stranded DNA fragment with the Ptrc promoter that was synthesized by IDT. The amplified gdhA gene, the upstream Ptrc promoter and the pACYC184 vector backbone were cloned together according to the InFusion cloning manual. The resulting pACYC-gdhA vector was transformed into E. coli via electroporation and selected for on LB chloramphenicol plates. Positive constructs were confirmed by DNA sequencing.

The effect of gdhA overexpression on alanine productivity was tested by comparative cultivation of E. coli with an empty control pACYC vector and E. coli harbouring the gdhA overexpression plasmid pACYC-gdhA (SEQ ID NO: 39). Precultures were grown in shake flasks with LB medium, 20% filling volume at 37 C and 200 rpm overnight. The fermentation was performed in the DASGIP 1.5 L parallel bioreactor system (Eppendorf) in 500 mL AM 1 medium (2.6 g/L (NH4)2HPO4, 0.87 g/L NH4H2PO4, 0.15 g/L Kill, 0.37 g/L MgSO4 ·7H2O, 15 g/L (NH4)2SO4, 1 mM betaine, 1 ml/L trace metal stock solution). The trace metal stock comprised 1.6 g/L FeCL3 ·6H2O; 0.2 g/L CoCl2 ·6H2O; 0.1 g/L CuCl$_2$·2H2O; 0.2 g/L ZnCl2; 0.2 g/L NaMoO4 ·2H2O; 0.05 g/L H3BO3, 0.1 M HCL. 120 g/L Glucose were used as carbon source in the fermentation medium. 25 ug/mL chloramphenicol were added to stably maintain the plasmid. Expression of the gdhA gene from the Ptrc promoter was induced with 250 uM isopropyl β-D-1-thiogalactopyranoside (IPTG) during the early logarithmic growth phase. Each strain was run in duplicates at 37 C and 400 rpm stirrer speed. 5N NH$_4$OH was used to control the pH to 6.8 and provide the culture with ammonium as an alanine precursor throughout the fermentation. No air was sparged during the fermentation and the vessel was not pressurized so that after the initial consumption of dissolved oxygen in the medium by the cells the fermentation was run under microaerobic conditions. Samples were taken throughout the fermentation and analyzed by HPLC for alanine and glucose concentrations.

Figure 2:
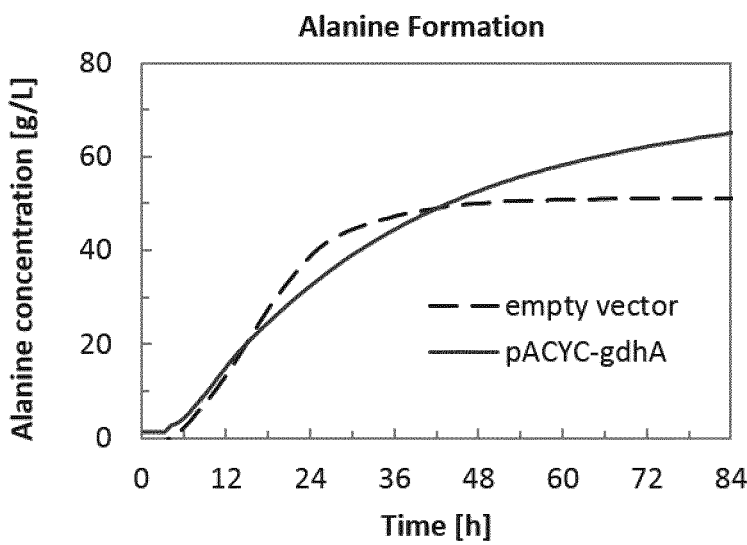

After 72 h of fermentation time E. coli QZ20 in which the gdhA gene (SEQ ID NO: 37) was overexpressed from the pACYC-gdhA plasmid (SEQ ID NO: 39) reached a significantly higher L-alanine titer of 62.18±0.37 g/L compared to the strain harbouring the empty control plasmid with 50.96±3.41 g/L (FIG. 2).

We claim:

1. A recombinant microorganism having a higher yield and/or productivity of alanine in a fermentative production compared to a respective control microorganism, the recombinant microorganism comprising:
   (a) an asd gene encoding and expressing an aspartate-beta semialdehyde dehydrogenase, wherein the asd gene is introduced into the recombinant microorganism or the asd gene expression is increased when compared to the microorganism without increased expression of the asd gene;
   (b) an alaD gene encoding and expressing an alanine dehydrogenase, wherein the alaD gene is introduced into the recombinant microorganism or the alaD gene expression is increased when compared to the microorganism without increased expression of the alaD gene; and
   (c) an IdhA gene encoding a NAO-dependent fermentative D-lactate dehydrogenase, wherein the IdhA gene is deleted or the IdhA gene expression is reduced when compared to the microorganism without reduced expression of the IdhA gene.

2. The recombinant microorganism of claim 1, wherein the asd gene is derived from the wild type E. coli W genomic DNA.

3. The recombinant microorganism of claim 1, wherein the asd gene is selected from the group consisting of:
   (a) a nucleic acid molecule comprising the sequence of SEQ ID NO: 25
   (b) a nucleic acid molecule having at least 80% identity to the nucleic acid molecule of SEQ ID NO: 25,
   (c) a nucleic acid molecule encoding the polypeptide of SEQ ID NO: 26, and
   (d) a nucleic acid molecule encoding a polypeptide having at least 60% identity to the polypeptide of SEQ ID NO: 26.

4. The recombinant microorganism of claim 1, wherein the alaD gene is selected from the group consisting of:
   (a) a nucleic acid molecule comprising the sequence of SEQ ID NO: 1,
   (b) a nucleic acid molecule having at least 80% identity to the nucleic acid molecule of SEQ ID NO: 1,
   (c) a nucleic acid molecule encoding the polypeptide of SEQ ID NO: 2, and
   (d) a nucleic acid molecule encoding a polypeptide having at least 60% identity to the polypeptide of SEQ ID NO: 2.

5. The recombinant microorganism of claim 1, wherein the IdhA gene is selected from the group consisting of:
   (a) a nucleic acid molecule comprising the sequence of SEQ ID NO: 9,
   (b) a nucleic acid molecule having at least 80% identity to the nucleic acid molecule of SEQ ID NO: 9,
   (c) a nucleic acid molecule encoding the polypeptide of SEQ ID NO: 10, and
   (d) a nucleic acid molecule encoding a polypeptide having at least 60% identity to the polypeptide of SEQ ID NO: 10.

6. The recombinant microorganism of claim 1, further comprising at least one of a deleted gene or a gene with reduced expression when compared to the microorganism without reduced expression of the gene, wherein said gene is selected from:
   (a) a pflB gene encoding a pyruvate formate lyase 1,
   (b) adhE gene encoding a bifunctional acetaldehyde-CoA dehydrogenase/ iron-dependent alcohol dehydrogenase/pyruyate-formate lyase deactivase,
   (c) a pta gene encoding a phosphate acetyltransferase,
   (d) an ackA gene encoding an acetate kinase A and propionate kinase 2,
   (e) are frdA gene encoding a fumarate reductase,
   (f) a dadX gene encoding an alanine racemase,
   (g) a brnQ gene encoding a brnQ protein having branched chain amino acid transforming activity, and
   (h) a gcvB gene encoding a non-protein encoding RNA;
   and/or at least one of a gene that is introduced into the recombinant microorganism or a gene with increased expression when compared to the microorganism without increased expression of the gene, wherein said gene is selected from:
   (i) a zipA gene encoding a cell division protein involved in Z ring assembly,
   (j) an Ipd gene encoding a lipoamide dehydrogenase,
   (k) gcvA gene encoding a DNA binding protein, and
   (l) a ygaW gene encoding an alanine transporter protein.

7. The recombinant microorganism of claim 6, wherein the pflB gene is selected from the group consisting of:
   (a) a nucleic acid molecule comprising the sequence of SEQ ID NO: 5,
   (b) a nucleic acid molecule having at least 80% identity to the nucleic acid molecule of SEQ ID NO: 5,
   (c) a nucleic acid molecule encoding the polypeptide of SEQ ID NO: 6, and
   (d) a nucleic acid molecule encoding a polypeptide having at least 60% identity to the polypeptide of SEQ ID NO: 6.

8. The recombinant microorganism of claim 6, wherein the adhE gene is selected from the group consisting of:
   (a) a nucleic acid molecule comprising the sequence of SEQ ID NO: 7,
   (b) a nucleic acid molecule having at least 80% identity to the nucleic acid molecule of SEQ ID NO: 7,
   (c) a nucleic acid molecule encoding the polypeptide of SEQ ID NO: 8, and
   (d) a nucleic acid molecule encoding a polypeptide having at least 60% identity to the polypeptide of SEQ ID NO: 8.

9. The recombinant microorganism of claim 6, wherein the pta gene is selected from the group consisting of:
   (a) a nucleic acid molecule comprising the sequence of SEQ ID NO: 11, (b) a nucleic acid molecule having at least 80% identity to the nucleic acid molecule of SEQ ID NO: 11,
(c) a nucleic acid molecule encoding the polypeptide of SEQ ID NO: 12,
(d) a nucleic acid molecule encoding a polypeptide haying at least 60% identity to the polypeptide of SEQ ID NO: 12.

10. The recombinant microorganism of claim 6, wherein the ackA gene is selected from the group consisting of:
(a) a nucleic acid molecule comprising the sequence of SEQ ID NO: 32,
(b) a nucleic acid molecule having at least 80% identity to the nucleic acid molecule of SEQ ID NO: 32,
(c) a nucleic acid molecule encoding the polypeptide of SEQ ID NO: 33, and
(d) a nucleic acid molecule encoding a polypeptide haying at least 60% identity to the polypeptide of SEQ ID NO: 33.

11. The recombinant microorganism of claim 6, wherein the frdA gene is selected from the group consisting of:
(a) a nucleic acid molecule comprising the sequence of SEQ ID NO: 13,
(b) a nucleic acid molecule having at least 80% identity to the nucleic acid molecule of SEQ ID NO: 13,
(c) a nucleic acid molecule encoding the polypeptide of SEQ ID NO: 14, and
(d) a nucleic acid molecule encoding a polypeptide having at least 60% identity to the polypeptide of SEQ ID NO: 14.

12. The recombinant microorganism of claim 6, wherein the dadX gene is selected from the group consisting of:
(a) a nucleic acid molecule comprising the sequence of SEQ ID NO: 15,
(b) a nucleic acid molecule having at least 80% identity to the nucleic acid molecule of SEQ ID NO: 15,
(c) a nucleic acid molecule encoding the polypeptide of SEQ ID NO: 16, and
(d) a nucleic acid molecule encoding a polypeptide having at least 60% identity to the polypeptide of SEQ ID NO: 16.

13. The recombinant microorganism of claim 6, wherein the brnQ gene is selected from the group consisting of:
(a) a nucleic acid molecule comprising the sequence of SEQ ID NO: 23,
(b) a nucleic acid molecule having at least 80% identity to the nucleic acid molecule of SEQ ID NO: 23,
(c) a nucleic acid molecule encoding the polypeptide of SEQ ID NO: 24, and
(d) a nucleic acid molecule encoding a polypeptide having at least 60% identity to the polypeptide of SEQ ID NO: 24.

14. The recombinant microorganism of claim 6, wherein the gcvB gene is selected from the group consisting of:
(a) a nucleic acid molecule comprising the sequence of SEQ ID NO: 31, and
(b) a nucleic acid molecule having at least 80% identity to the nucleic acid molecule of SEQ ID NO: 31.

15. The recombinant microorganism of claim 6, wherein the zipA gene is selected from the group consisting of:
(a) a nucleic acid molecule comprising the sequence of SEQ ID NO: 19,
(b) a nucleic acid molecule having at least 80% identity to the nucleic acid molecule of SEQ ID NO: 19,
(c) a nucleic acid molecule encoding the polypeptide of SEQ ID NO: 20, and
(d) a nucleic acid molecule encoding a polypeptide having at least 60% identity to the polypeptide of SEQ ID NO: 20.

16. The recombinant microorganism of claim 6, wherein the Ipd gene is selected from the group consisting of:
(a) a nucleic acid molecule comprising the sequence of SEQ ID NO: 21,
(b) a nucleic acid molecule having at least 80% identity to the nucleic acid molecule of SEQ ID NO: 21,
(c) a nucleic acid molecule encoding the polypeptide of SEQ ID NO: 22, and
(d) a nucleic acid molecule encoding a polypeptide having at least 60% identity to the polypeptide of SEQ ID NO: 22.

17. The recombinant microorganism of claim 6, wherein the gcvA gene is selected from the group consisting of:
(a) a nucleic acid molecule comprising the sequence of SEQ ID NO: 29,
(b) a nucleic acid molecule having at least 80% identity to the nucleic acid molecule of SEQ ID NO: 29,
(c) a nucleic acid molecule encoding the polypeptide of SEQ ID NO: 30, and
(d) a nucleic acid molecule encoding a polypeptide having at least 60% identity to the polypeptide of SEQ ID NO: 30.

18. The recombinant microorganism of claim 6, wherein the ygaW gene is selected from the group consisting of:
(a) a nucleic acid molecule comprising the sequence of SEQ ID NO: 17,
(b) a nucleic acid molecule having at least 80% identity to the nucleic acid molecule of SEQ ID NO: 17,
(c) a nucleic acid molecule encoding the polypeptide of SEQ ID NO: 18, and
(d) a nucleic acid molecule encoding a polypeptide having at least 60% identity to the polypeptide of SEQ ID NO: 18.

19. The recombinant microorganism of claim 1, wherein the microorganism is selected from a genus of the group consisting of Corynebacterium, Bacillus, Erwinia, Escherichia, Pantoea, Streptomyces, Zymomonas, Rhodococcus, Saccharomyces, Candida, and Pichia.

20. A method of producing alanine comprising culturing one or more recombinant microorganism according to claim 1 under conditions that allow for the production of alanine.

21. The method of claim 20, comprising:
(a) growing the one or more recombinant microorganism in a fermenter to obtain fermentation broth, and
(b) recovering alanine from the fermentation broth.

* * * * *

SEQUENCE LISTING

<160> NUMBER OF SEQ ID NOS: 41

<210> SEQ ID NO 1
<211> LENGTH: 1119
<212> TYPE: DNA
<213> ORGANISM: G.stearothermophilus
<220> FEATURE:
<221> NAME/KEY: misc_feature
<222> LOCATION: (1)..(1119)
<223> OTHER INFORMATION: alaD

<400> SEQUENCE: 1

```
atgaaaattg gcatccctaa agagattaag aacaatgaaa accgtgtagc aatcaccccg        60
gcaggtgtta tgactctggt taaagcgggc acgatgtgt acgtcgaaac cgaagcgggt       120
gccggcagcg gcttcagcga cagcgagtat gagaaggcgg tgcggttat tgtgactaag       180 gcggaggacg cttgggcagc cgaaatggtt ctgaaggtga agaaccgct ggcggaggag       240 tttcgctatt ttcgtccggg tctgattttg ttcacctacc tgcacctggc tgcggccgag       300
gcgctgacca aggcactggt ggagcagaag gttgttggca tcgcgtacga aacggttcaa       360
ctggcgaatg gttccctgcc gctgctgacc cctatgtctg aagttgcggg tcgcatgagc       420
gttcaagtcg gcgctcagtt tctggagaaa ccgcacggtg gcaagggcat tttgctgggt       480
ggtgttccgg gtgtccgccg tggtaaagtg acgatcattg gcggtggtac ggccggtacg       540
aacgcggcca agattgccgt aggtctgggt gcagatgtga ccattctgga catcaacgcg       600
gaacgtttgc gtgagctgga cgacctgttt ggcgaccaag tcaccaccct gatgagcaac       660
agctaccaca tcgcggagtg cgtccgtgaa agcgatttgg tcgttggtgc ggtgctgatc       720
ccgggtgcaa aagccccgaa actggtgacc gaggagatgg tccgtagcat gaccccgggt       780
tcggttctgg tcgacgtggc aattgaccag ggcggtatct tcgaaaccac cgaccgcgtc       840
acgacccatg atgacccgac ctatgtgaaa catggcgtgg ttcactatgc ggtcgcgaat       900
atgccgggtg cagtgccgcg cacgtccacg ttcgcgctga cgaacgtgac gattccatac       960
gctctgcaga tcgccaataa gggctatcgt gcggcgtgtc tggataatcc ggcattgctg      1020
aaaggcatca ataccctgga tggtcatatc gtttacgagg ctgtggctgc agcacacaac      1080
atgccgtaca ctgatgtcca tagcttgctg caaggctaa                             1119
```

<210> SEQ ID NO 2
<211> LENGTH: 372
<212> TYPE: PRT
<213> ORGANISM: G.stearothermophilus
<220> FEATURE:
<221> NAME/KEY: MISC_FEATURE
<222> LOCATION: (1)..(372)
<223> OTHER INFORMATION: alaD

<400> SEQUENCE: 2

```
Met Lys Ile Gly Ile Pro Lys Glu Ile Lys Asn Asn Glu Asn Arg Val
1               5                   10                  15

Ala Ile Thr Pro Ala Gly Val Met Thr Leu Val Lys Ala Gly His Asp
            20                  25                  30

Val Tyr Val Glu Thr Glu Ala Gly Ala Gly Ser Gly Phe Ser Asp Ser
        35                  40                  45

Glu Tyr Glu Lys Ala Gly Ala Val Ile Val Thr Lys Ala Glu Asp Ala
    50                  55                  60

Trp Ala Ala Glu Met Val Leu Lys Val Lys Glu Pro Leu Ala Glu Glu
65                  70                  75                  80
```

Phe Arg Tyr Phe Arg Pro Gly Leu Ile Leu Phe Thr Tyr Leu His Leu
                 85                  90                  95

Ala Ala Ala Glu Ala Leu Thr Lys Ala Leu Val Glu Gln Lys Val Val
            100                 105                 110

Gly Ile Ala Tyr Glu Thr Val Gln Leu Ala Asn Gly Ser Leu Pro Leu
            115                 120                 125

Leu Thr Pro Met Ser Glu Val Ala Gly Arg Met Ser Val Gln Val Gly
130                 135                 140

Ala Gln Phe Leu Glu Lys Pro His Gly Gly Lys Gly Ile Leu Leu Gly
145                 150                 155                 160

Gly Val Pro Gly Val Arg Arg Gly Lys Val Thr Ile Ile Gly Gly Gly
                165                 170                 175

Thr Ala Gly Thr Asn Ala Ala Lys Ile Ala Val Gly Leu Gly Ala Asp
                180                 185                 190

Val Thr Ile Leu Asp Ile Asn Ala Glu Arg Leu Arg Glu Leu Asp Asp
                195                 200                 205

Leu Phe Gly Asp Gln Val Thr Thr Leu Met Ser Asn Ser Tyr His Ile
210                 215                 220

Ala Glu Cys Val Arg Glu Ser Asp Leu Val Val Gly Ala Val Leu Ile
225                 230                 235                 240

Pro Gly Ala Lys Ala Pro Lys Leu Val Thr Glu Glu Met Val Arg Ser
                245                 250                 255

Met Thr Pro Gly Ser Val Leu Val Asp Val Ala Ile Asp Gln Gly Gly
                260                 265                 270

Ile Phe Glu Thr Thr Asp Arg Val Thr Thr His Asp Asp Pro Thr Tyr
                275                 280                 285

Val Lys His Gly Val Val His Tyr Ala Val Ala Asn Met Pro Gly Ala
    290                 295                 300

Val Pro Arg Thr Ser Thr Phe Ala Leu Thr Asn Val Thr Ile Pro Tyr
305                 310                 315                 320

Ala Leu Gln Ile Ala Asn Lys Gly Tyr Arg Ala Ala Cys Leu Asp Asn
                325                 330                 335

Pro Ala Leu Leu Lys Gly Ile Asn Thr Leu Asp Gly His Ile Val Tyr
                340                 345                 350

Glu Ala Val Ala Ala Ala His Asn Met Pro Tyr Thr Asp Val His Ser
                355                 360                 365

Leu Leu Gln Gly
    370

<210> SEQ ID NO 3
<211> LENGTH: 269
<212> TYPE: DNA
<213> ORGANISM: E.coli
<220> FEATURE:
<221> NAME/KEY: misc_feature
<222> LOCATION: (1)..(269)
<223> OTHER INFORMATION: ldhA mut Promoter

<400> SEQUENCE: 3
catagtaaat tcccccacca gtttaaccgg cggctgattt tcaaacgcga cgacatccag    60
ttcgctgact gtaagttgtt gccctttcag ctggccttga aatttaactt tttcgccctg   120
ataacgcagt tgctggatat cagaggttaa tgcgagagag agttttccct gccattcctg   180
ccagggagaa aaaatcagtt tatcgatatt gattttgtaa aatattttta gtagcttaaa   240
tgtgattcaa catcactgga gaaagtctt                                     269

<210> SEQ ID NO 4
<211> LENGTH: 50
<212> TYPE: DNA
<213> ORGANISM: E.coli
<220> FEATURE:
<221> NAME/KEY: misc_feature
<222> LOCATION: (1)..(50)
<223> OTHER INFORMATION: ldhA mut Promoter fragment

<400> SEQUENCE: 4
tattgatttt gtaaaatatt tttagtagct taaatgtgat tcaacatcac          50

<210> SEQ ID NO 5
<211> LENGTH: 2283
<212> TYPE: DNA
<213> ORGANISM: E.coli
<220> FEATURE:
<221> NAME/KEY: misc_feature
<222> LOCATION: (1)..(2283)
<223> OTHER INFORMATION: pflB

<400> SEQUENCE: 5

```
atgtccgagc ttaatgaaaa gttagccaca gcctgggaag gttttaccaa aggtgactgg     60
cagaatgaag taaacgtccg tgacttcatt cagaaaaact acactccgta cgagggtgac    120
gagtccttcc tggctggcgc tactgaagcg accaccaccc tgtgggacaa agtaatggaa    180
ggcgttaaac tggaaaaccg cactcacgcg ccagttgact ttgacaccgc tgttgcttcc    240
accatcacct ctcacgacgc tggctacatc aacaaagcgt ggaaaaagt tgttggtcta    300 cagactgaag ctccgctgaa acgtgctctt atcccgttcg gtggtatcaa aatgatcgag    360
ggttcctgca aagcgtacaa ccgcgaactg gacccgatga tcaaaaaaat cttcactgaa    420
taccgtaaaa ctcacaacca gggcgtgttc gacgtttaca ctccggacat cctgcgttgc    480
cgtaaatccg gtgttctgac cggtctgcca gatgcttatg ccgtggccg tatcatcggt    540 gactaccgtc gcgttgcgct gtacggtatc gactacctga tgaaagacaa atacgctcag    600
ttcacctctc tgcaggctga tctggaaaac ggcgtaaacc tggaacagac tatccgtctg    660
cgcgaagaaa tcgctgaaca gcaccgcgct ctgggtcaga tgaaagaaat ggctgcgaaa    720
tacggctacg acatctctgg tccggctacc aacgctcagg aagctatcca gtggactac    780 ttcggctacc tggctgctgt taagtctcag aacggtgctg caatgtcctt cggtcgtacc    840
tccaccttcc tggatgtgta catcgaacgt gacctgaaag ctggcaagat caccgaacaa    900
gaagcgcagg aaatggttga ccacctggtc atgaaactgc gtatggttcg cttcctgcgt    960
actccggaat acgatgaact gttctctggc gacccgatct gggcaaccga atctatcggt   1020
ggtatgggcc tcgacggtcg tacccctggtt accaaaaaca gcttccgttt cctgaacacc   1080
ctgtacacca tgggtccgtc tccggaaccg aacatgacca ttctgtggtc tgaaaaactg   1140
ccgctgaact tcaagaaatt cgccgctaaa gtgtccatcg acacctcttc tctgcaatat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca gtacagcta cgaagcctct ctgatggcgc tgcacgaccg tgacgttatc   1560
cgcaccatgg cgtgtggtat cgctggtctg tccgttgctg ctgactccct gtctgcaatc   1620
```

```
aaatatgcga aagttaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac tggtaacacc   1860
ccagacggtc gtcgtgctgg cgcgccgttc ggaccgggtg ctaacccgat gcacggtcgt   1920
gaccagaaag gtgctgtagc gtctctgact tccgttgcta aactaccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160 gaaaaccc gg aaaatatcc gcagctgacc atccgtgtat ctggctacgc agtacgtttc   2220
aactcgctga ctaagaaca gcagcaggac gttattactc gtaccttcac tcaatctatg   2280
taa                                                                 2283
```

<210> SEQ ID NO 6
<211> LENGTH: 760
<212> TYPE: PRT
<213> ORGANISM: E.coli
<220> FEATURE:
<221> NAME/KEY: MISC_FEATURE
<222> LOCATION: (1)..(760)
<223> OTHER INFORMATION: pflB

<400> SEQUENCE: 6

```
Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
    50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Ala Leu Glu Lys
                85                  90                  95

Val Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly
                165                 170                 175

Arg Ile Ile Gly Asp Tyr Arg Arg Val Ala Leu Tyr Gly Ile Asp Tyr
            180                 185                 190

Leu Met Lys Asp Lys Tyr Ala Gln Phe Thr Ser Leu Gln Ala Asp Leu
        195                 200                 205

Glu Asn Gly Val Asn Leu Glu Gln Thr Ile Arg Leu Arg Glu Glu Ile
    210                 215                 220
```

```
Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
            245                 250                 255

Gln Trp Thr Tyr Phe Gly Tyr Leu Ala Ala Val Lys Ser Gln Asn Gly
        260                 265                 270

Ala Ala Met Ser Phe Gly Arg Thr Ser Thr Phe Leu Asp Val Tyr Ile
    275                 280                 285

Glu Arg Asp Leu Lys Ala Gly Lys Ile Thr Glu Gln Glu Ala Gln Glu
290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
            325                 330                 335

Glu Ser Ile Gly Gly Met Gly Leu Asp Gly Arg Thr Leu Val Thr Lys
        340                 345                 350

Asn Ser Phe Arg Phe Leu Asn Thr Leu Tyr Thr Met Gly Pro Ser Pro
    355                 360                 365

Glu Pro Asn Met Thr Ile Leu Trp Ser Glu Lys Leu Pro Leu Asn Phe
370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Tyr Ala
            405                 410                 415

Ile Ala Cys Cys Val Ser Pro Met Ile Val Gly Lys Gln Met Gln Phe
            420                 425                 430

Phe Gly Ala Arg Ala Asn Leu Ala Lys Thr Met Leu Tyr Ala Ile Asn
        435                 440                 445

Gly Gly Val Asp Glu Lys Leu Lys Met Gln Val Gly Pro Lys Ser Glu
    450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
            485                 490                 495

Ile Ile His Tyr Met His Asp Lys Tyr Ser Tyr Glu Ala Ser Leu Met
        500                 505                 510

Ala Leu His Asp Arg Asp Val Ile Arg Thr Met Ala Cys Gly Ile Ala
    515                 520                 525

Gly Leu Ser Val Ala Ala Asp Ser Leu Ser Ala Ile Lys Tyr Ala Lys
    530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
            565                 570                 575

Leu Ala Val Asp Leu Val Glu Arg Phe Met Lys Ile Gln Lys Leu
        580                 585                 590

His Thr Tyr Arg Asp Ala Ile Pro Thr Gln Ser Val Leu Thr Ile Thr
    595                 600                 605

Ser Asn Val Val Tyr Gly Lys Lys Thr Gly Asn Thr Pro Asp Gly Arg
    610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
```

```
                    645                 650                 655
Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
        675                 680                 685

Leu Met Asp Gly Tyr Phe His His Glu Ala Ser Ile Glu Gly Gly Gln
    690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
                725                 730                 735

Ala Val Arg Phe Asn Ser Leu Thr Lys Glu Gln Gln Gln Asp Val Ile
            740                 745                 750

Thr Arg Thr Phe Thr Gln Ser Met
        755                 760

<210> SEQ ID NO 7
<211> LENGTH: 2676
<212> TYPE: DNA
<213> ORGANISM: E.coli
<220> FEATURE:
<221> NAME/KEY: misc_feature
<222> LOCATION: (1)..(2676)
<223> OTHER INFORMATION: adhE

<400> SEQUENCE: 7
```

| | | | | | |
|---|---|---|---|---|---|
| atggctgtta | ctaatgtcgc | tgaacttaac | gcactcgtag | agcgtgtaaa | aaaagcccag | 60 |
| cgtgaatatg | ccagtttcac | tcaagagcaa | gtagacaaaa | tcttccgcgc | cgccgctctg | 120 |
| gctgctgcag | atgctcgaat | cccactcgcg | aaaatggccg | ttgccgaatc | cggcatgggt | 180 |
| atcgtcgaag | ataaagtgat | caaaaaccac | tttgcttctg | aatatatcta | caacgcctat | 240 |
| aaagatgaaa | aaacctgtgg | tgttctgtct | gaagacgaca | cttttggtac | catcactatc | 300 |
| gctgaaccaa | tcggtattat | tgcggtatc | gttccgacca | ctaacccgac | ttcaactgct | 360 |
| atcttcaaat | cgctgatcag | tctgaagacc | cgtaacgcca | ttatcttctc | cccgcacccg | 420 |
| cgtgcaaaag | atgccaccaa | caaagcggct | gatatcgttc | tgcaggctgc | tatcgctgcc | 480 |
| ggtgctccga | agatctgat | cggctggatc | gatcaacctt | ctgttgaact | gtctaacgca | 540 |
| ctgatgcacc | acccagacat | caacctgatc | ctcgcgactg | gtggtccggg | catggttaaa | 600 |
| gccgcataca | gctccggtaa | accagctatc | ggtgtaggcg | cgggcaacac | tccagttgtt | 660 |
| atcgatgaaa | ctgctgatat | caaacgtgca | gttgcatctg | tactgatgtc | caaaaccttc | 720 |
| gacaacggcg | taatctgtgc | ttctgaacag | tctgttgttg | ttgttgactc | tgtttatgac | 780 |
| gctgtacgtg | aacgttttgc | aacccacggc | ggctatctgt | tgcagggtaa | agagctgaaa | 840 |
| gctgttcagg | atgttatcct | gaaaaacggt | gcgctgaacg | cggctatcgt | tggtcagcca | 900 |
| gcctataaaa | ttgctgaact | ggcaggcttc | tctgtaccag | aaaacaccaa | gattctgatc | 960 |
| ggtgaagtga | ccgttgttga | tgaaagcgaa | ccgttcgcac | atgaaaaact | gtccccgact | 1020 |
| ctggcaatgt | accgcgctaa | agatttcgaa | gacgcggtag | aaaaagcaga | gaaactggtt | 1080 |
| gctatgggcg | gtatcggtca | tacctcttgc | ctgtacactg | accaggataa | ccaaccggct | 1140 |
| cgcgtttctt | acttcggtca | gaaaatgaaa | acggctcgta | tcctgattaa | caccccagcg | 1200 |
| tctcagggtg | gtatcggtga | cctgtataac | ttcaaactcg | caccttccct | gactctgggt | 1260 |
| tgtggttctt | ggggtggtaa | ctccatctct | gaaaacgttg | gtccgaaaca | cctgatcaac | 1320 |

| | | |
|---|---|---|
| aagaaaaccg ttgctaagcg agctgaaaac atgttgtggc acaaacttcc gaaatctatc | 1380 | |
| tacttccgcc gtggctccct gccaatcgcg ctggatgaag tgattactga tggccacaaa | 1440 | |
| cgtgcgctca tcgtgactga ccgcttcctg ttcaacaatg gttatgctga tcagatcact | 1500 | |
| tccgtactga aagcagcagg cgttgaaact gaagtcttct tcgaagtaga agcggacccg | 1560 | |
| accctgagca tcgttcgtaa aggtgcagaa ctggcaaact ccttcaaacc agacgtgatt | 1620 | |
| atcgcgctgg gtggtggttc cccgatggac gccgcgaaga tcatgtgggt tatgtacgaa | 1680 | |
| catccggaaa ctcacttcga agagctggcg ctgcgcttta tggatatccg taaacgtatc | 1740 | |
| tacaagttcc cgaaaatggg cgtgaaagcg aaaatgatcg ctgtcaccac cacttctggt | 1800 | |
| acaggttctg aagtcactcc gtttgcggtt gtaactgacg acgctactgg tcagaaatat | 1860 | |
| ccgctggcag actatgcgct gactccggat atggcgattg tcgacgccaa cctggttatg | 1920 | |
| gacatgccga agtccctgtg tgctttcggt ggtctggacg cagtaactca cgccatggaa | 1980 | |
| gcttatgttt ctgtactggc atctgagttc tctgatggtc aggctctgca ggcactgaaa | 2040 | |
| ctgctgaaag aatatctgcc agcgtcctac acgaagggt ctaaaaatcc ggtagcgcgt | 2100 | |
| gaacgtgttc acagtgcagc gactatcgcg ggtatcgcgt ttgcgaacgc cttcctgggt | 2160 | |
| gtatgtcact caatggcgca caaactgggt tcccagttcc atattccgca cggtctggca | 2220 | |
| aacgccctgc tgatttgtaa cgttattcgc tacaatgcga acgacaaccc gaccaagcag | 2280 | |
| actgcattca gccagtatga ccgtccgcag gctcgccgtc gttatgctga aattgccgac | 2340 | |
| cacttgggtc tgagcgcacc gggcgaccgt actgctgcta agatcgagaa actgctggca | 2400 | |
| tggctggaaa cgctgaaagc tgaactgggt attccgaaat ctatccgtga agctggcgtt | 2460 | |
| caggaagcag acttcctggc gaacgtggat aaactgtctg aagatgcgtt cgatgaccag | 2520 | |
| tgcaccggcg ctaacccgcg ttacccgctg atctccgagc tgaaacagat cctgctggat | 2580 | |
| acctactacg gtcgtgatta tgtagaaggt gaaactgcag cgaaaaaaga gccgctccg | 2640 | |
| gctaaagctg agaaaaaagc gaaaaaatcc gcttaa | 2676 | |

<210> SEQ ID NO 8
<211> LENGTH: 891
<212> TYPE: PRT
<213> ORGANISM: E.coli
<220> FEATURE:
<221> NAME/KEY: MISC_FEATURE
<222> LOCATION: (1)..(891)
<223> OTHER INFORMATION: adhE

<400> SEQUENCE: 8

Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

```
Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
130                 135                 140

Ala Thr Asn Lys Ala Ala Asp Ile Val Leu Gln Ala Ala Ile Ala Ala
145                 150                 155                 160

Gly Ala Pro Lys Asp Leu Ile Gly Trp Ile Asp Gln Pro Ser Val Glu
                165                 170                 175

Leu Ser Asn Ala Leu Met His His Pro Asp Ile Asn Leu Ile Leu Ala
            180                 185                 190

Thr Gly Gly Pro Gly Met Val Lys Ala Ala Tyr Ser Ser Gly Lys Pro
        195                 200                 205

Ala Ile Gly Val Gly Ala Gly Asn Thr Pro Val Val Ile Asp Glu Thr
    210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
    290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
                325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
    370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
                405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
    450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
                485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
```

```
                    530             535             540
Gly Gly Ser Pro Met Asp Ala Ala Lys Ile Met Trp Val Met Tyr Glu
545                 550             555                 560

His Pro Glu Thr His Phe Glu Leu Ala Leu Arg Phe Met Asp Ile
                565             570             575

Arg Lys Arg Ile Tyr Lys Phe Pro Lys Met Gly Val Lys Ala Lys Met
                580             585             590

Ile Ala Val Thr Thr Thr Ser Gly Thr Gly Ser Glu Val Thr Pro Phe
                595             600             605

Ala Val Val Thr Asp Asp Ala Thr Gly Gln Lys Tyr Pro Leu Ala Asp
                610             615             620

Tyr Ala Leu Thr Pro Asp Met Ala Ile Val Asp Ala Asn Leu Val Met
625                 630             635                 640

Asp Met Pro Lys Ser Leu Cys Ala Phe Gly Gly Leu Asp Ala Val Thr
                645             650             655

His Ala Met Glu Ala Tyr Val Ser Val Leu Ala Ser Glu Phe Ser Asp
                660             665             670

Gly Gln Ala Leu Gln Ala Leu Lys Leu Leu Lys Glu Tyr Leu Pro Ala
                675             680             685

Ser Tyr His Glu Gly Ser Lys Asn Pro Val Ala Arg Glu Arg Val His
                690             695             700

Ser Ala Ala Thr Ile Ala Gly Ile Ala Phe Ala Asn Ala Phe Leu Gly
705                 710             715                 720

Val Cys His Ser Met Ala His Lys Leu Gly Ser Gln Phe His Ile Pro
                725             730             735

His Gly Leu Ala Asn Ala Leu Leu Ile Cys Asn Val Ile Arg Tyr Asn
                740             745             750

Ala Asn Asp Asn Pro Thr Lys Gln Thr Ala Phe Ser Gln Tyr Asp Arg
                755             760             765

Pro Gln Ala Arg Arg Arg Tyr Ala Glu Ile Ala Asp His Leu Gly Leu
                770             775             780

Ser Ala Pro Gly Asp Arg Thr Ala Ala Lys Ile Glu Lys Leu Leu Ala
785                 790             795                 800

Trp Leu Glu Thr Leu Lys Ala Glu Leu Gly Ile Pro Lys Ser Ile Arg
                805             810             815

Glu Ala Gly Val Gln Glu Ala Asp Phe Leu Ala Asn Val Asp Lys Leu
                820             825             830

Ser Glu Asp Ala Phe Asp Asp Gln Cys Thr Gly Ala Asn Pro Arg Tyr
                835             840             845

Pro Leu Ile Ser Glu Leu Lys Gln Ile Leu Leu Asp Thr Tyr Tyr Gly
850                 855             860

Arg Asp Tyr Val Glu Gly Glu Thr Ala Lys Lys Glu Ala Ala Pro
865                 870             875             880

Ala Lys Ala Glu Lys Lys Ala Lys Lys Ser Ala
                885             890
```

<210> SEQ ID NO 9
<211> LENGTH: 990
<212> TYPE: DNA
<213> ORGANISM: E.coli
<220> FEATURE:
<221> NAME/KEY: misc_feature
<222> LOCATION: (1)..(990)
<223> OTHER INFORMATION: ldhA

<400> SEQUENCE: 9

```
atgaaactcg ccgtttatag cacaaaacag tacgacaaga agtacctgca acaggtgaac    60
gagtcctttg gctttgagct ggaattttt gactttctgc tgacggaaaa aaccgctaaa   120
actgccaatg gctgcgaagc ggtatgtatt ttcgtaaacg atgacggcag ccgcccggtg   180
ctggaagagc tgaaaaagca cggcgttaaa tatatcgccc tgcgctgtgc cggtttcaat   240
aacgtcgacc ttgacgcggc aaaagaactg gggctgaaag tagtccgtgt ccagcctat    300
gatccagagg ccgttgctga acacgccatc ggtatgatga tgacgctgaa ccgccgtatt   360
caccgcgcgt atcagcgtac ccgtgacgct aacttctctc tggaaggtct gaccggcttt   420
actatgtatg gcaaaacggc aggcgttatc ggtaccggta aaatcggtgt ggcgatgctg   480
cgcattctga aaggttttgg tatgcgtctg ctggcgttcg atccgtatcc aagtgcagcg   540
gcgctggaac tcggtgtgga gtatgtcgat ctgccaaccc tgttctctga atcagacgtt   600
atctctctgc actgcccgct gacaccggaa actaccatc tgttgaacga agccgccttc   660
gatcagatga aaaatggcgt gatgatcgtc aataccagtc gcggtgcatt gattgattct   720
caggcagcaa ttgaagcgct gaaaaatcag aaaattggtt cgttgggtat ggacgtgtat   780
gagaacgaac gcgatctatt ctttgaagat aaatccaacg acgtaattca ggatgacgta   840
ttccgtcgcc tgtctgcctg ccacaacgtg ctatttaccg ggcaccaggc attcctgaca   900
gcagaagctc tgaccagtat ttctcagact acgctgcaaa acttaagcaa tctggaaaaa   960
ggcgaaacct gcccgaacga actggtttaa                                   990
```

<210> SEQ ID NO 10
<211> LENGTH: 329
<212> TYPE: PRT
<213> ORGANISM: E.coli
<220> FEATURE:
<221> NAME/KEY: MISC_FEATURE
<222> LOCATION: (1)..(329)
<223> OTHER INFORMATION: ldhA

<400> SEQUENCE: 10

Met Lys Leu Ala Val Tyr Ser Thr Lys Gln Tyr Asp Lys Lys Tyr Leu
1               5                   10                  15

Gln Gln Val Asn Glu Ser Phe Gly Phe Glu Leu Glu Phe Phe Asp Phe
                20                  25                  30

Leu Leu Thr Glu Lys Thr Ala Lys Thr Ala Asn Gly Cys Glu Ala Val
            35                  40                  45

Cys Ile Phe Val Asn Asp Asp Gly Ser Arg Pro Val Leu Glu Glu Leu
        50                  55                  60

Lys Lys His Gly Val Lys Tyr Ile Ala Leu Arg Cys Ala Gly Phe Asn
65                  70                  75                  80

Asn Val Asp Leu Asp Ala Ala Lys Glu Leu Gly Leu Lys Val Val Arg
                85                  90                  95

Val Pro Ala Tyr Asp Pro Glu Ala Val Ala Glu His Ala Ile Gly Met
                100                 105                 110

Met Met Thr Leu Asn Arg Arg Ile His Arg Ala Tyr Gln Arg Thr Arg
            115                 120                 125

Asp Ala Asn Phe Ser Leu Glu Gly Leu Thr Gly Phe Thr Met Tyr Gly
        130                 135                 140

Lys Thr Ala Gly Val Ile Gly Thr Gly Lys Ile Gly Val Ala Met Leu
145                 150                 155                 160

Arg Ile Leu Lys Gly Phe Gly Met Arg Leu Leu Ala Phe Asp Pro Tyr
                165                 170                 175

```
Pro Ser Ala Ala Ala Leu Glu Leu Gly Val Glu Tyr Val Asp Leu Pro
            180                 185                 190

Thr Leu Phe Ser Glu Ser Asp Val Ile Ser Leu His Cys Pro Leu Thr
        195                 200                 205

Pro Glu Asn Tyr His Leu Leu Asn Glu Ala Ala Phe Asp Gln Met Lys
    210                 215                 220

Asn Gly Val Met Ile Val Asn Thr Ser Arg Gly Ala Leu Ile Asp Ser
225                 230                 235                 240

Gln Ala Ala Ile Glu Ala Leu Lys Asn Gln Lys Ile Gly Ser Leu Gly
                245                 250                 255

Met Asp Val Tyr Glu Asn Glu Arg Asp Leu Phe Phe Glu Asp Lys Ser
            260                 265                 270

Asn Asp Val Ile Gln Asp Val Phe Arg Arg Leu Ser Ala Cys His
        275                 280                 285

Asn Val Leu Phe Thr Gly His Gln Ala Phe Leu Thr Ala Glu Ala Leu
    290                 295                 300

Thr Ser Ile Ser Gln Thr Thr Leu Gln Asn Leu Ser Asn Leu Glu Lys
305                 310                 315                 320

Gly Glu Thr Cys Pro Asn Glu Leu Val
                325
```

<210> SEQ ID NO 11
<211> LENGTH: 2145
<212> TYPE: DNA
<213> ORGANISM: E.coli
<220> FEATURE:
<221> NAME/KEY: misc_feature
<222> LOCATION: (1)..(2145)
<223> OTHER INFORMATION: pta

<400> SEQUENCE: 11

```
gtgtcccgta ttattatgct gatccctacc ggaaccagcg tcggtctgac cagcgtcagc    60
cttggcgtga tccgtgcaat ggaacgcaaa ggcgttcgtc tgagcgtttt caaacctatc   120
gctcagccgc gtaccggtgg cgatgcgccc gatcagacta cgactatcgt gcgtgcgaac   180
tcttccacca cgacggccgc tgaaccgctg aaaatgagct acgttgaagg tctgctttcc   240
agcaatcaga aagatgtgct gatggaagag atcgtcgcaa actaccacgc taacaccaaa   300
gacgctgaag tcgttctggt tgaaggtctg gtcccgacac gtaagcacca gtttgcccag   360
tctctgaact acgaaatcgc taaaacgctg aatgcggaaa tcgtcttcgt tatgtctcag   420
ggcactgaca ccccggaaca gctgaaagag cgtatcgaac tgacccgcaa cagcttcggc   480
ggtgccaaaa acaccaacat caccggcgtt atcgttaaca aactgaacgc accggttgat   540
gaacagggtc gtactcgccc ggatctgtcc gagattttcg acgactcttc caaagctaaa   600
gtaaacaatg ttgatccggc gaagctgcaa gaatccagcc cgctgccggt tctcggcgct   660
gtgccgtgga gctttgacct gatcgcgact cgtgcgatcg atatggctcg ccacctgaat   720
gcgaccatca tcaacgaagg cgacatcaat actcgccgcg ttaaatccgt cactttctgc   780
gcacgcagca ttccgcacat gctggagcac ttccgtgccg ttctctgct ggtgacttcc   840
gcagaccgtc ctgacgtgct ggtggccgct tgcctggcag ccatgaacgg cgtagaaatc   900
ggtgccctgc tgctgactgg cggctacgaa atggacgcgc gcatttctaa actgtgcgaa   960
cgtgctttcg ctaccggcct gccggtattt atggtgaaca ccaacacctg cagacctct  1020
ctgagcctgc agagcttcaa cctggaagtt ccggttgacg atcacgagcg tatcgagaaa  1080
```

-continued

```
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa tccggcagag    1320
atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt ccggtgctg ttcacactac cgcaaacacc    1560
atccgtccgc cgctgcagct gatcaaaact gcaccgggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac cgcgcgttgc tatgctctcc tactccaccg gtacttctgg tgcaggtagc    1800
gacgtagaaa aagttcgcga agcaactcgt ctggcgcagg aaaaacgtcc tgacctgatg    1860
atcgacggtc cgctgcagta cgacgctgcg gtaatggctg acgttgcgaa atccaaagcg    1920
ccgaactctc cggttgcagg tcgcgctacc gtgttcatct cccggatct gaacaccggt    1980 aacaccacct acaaagcggt acagcgttct gccgacctga tctccatcgg gcgatgctg    2040 cagggtatgc gcaagccggt taacgacctg tcccgtggcg cactggttga cgatatcgtc    2100
tacaccatcg cgctgactgc gattcagtct gcacagcagc agtaa                   2145
```

<210> SEQ ID NO 12
<211> LENGTH: 714
<212> TYPE: PRT
<213> ORGANISM: E.coli
<220> FEATURE:
<221> NAME/KEY: MISC_FEATURE
<222> LOCATION: (1)..(714)
<223> OTHER INFORMATION: pta

<400> SEQUENCE: 12

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
            20                  25                  30

Arg Leu Ser Val Phe Lys Pro Ile Ala Gln Pro Arg Thr Gly Gly Asp
        35                  40                  45

Ala Pro Asp Gln Thr Thr Thr Ile Val Arg Ala Asn Ser Ser Thr Thr
    50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

Ala Asn Thr Lys Asp Ala Glu Val Val Leu Val Glu Gly Leu Val Pro
            100                 105                 110

Thr Arg Lys His Gln Phe Ala Gln Ser Leu Asn Tyr Glu Ile Ala Lys
        115                 120                 125

Thr Leu Asn Ala Glu Ile Val Phe Val Met Ser Gln Gly Thr Asp Thr
    130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn

-continued

```
            165                 170                 175
Ala Pro Val Asp Glu Gln Gly Arg Thr Arg Pro Asp Leu Ser Glu Ile
            180                 185                 190
Phe Asp Ser Ser Lys Ala Lys Val Asn Asn Val Asp Pro Ala Lys
            195                 200                 205
Leu Gln Glu Ser Ser Pro Leu Pro Val Leu Gly Ala Val Pro Trp Ser
    210                 215                 220
Phe Asp Leu Ile Ala Thr Arg Ala Ile Asp Met Ala Arg His Leu Asn
225                 230                 235                 240
Ala Thr Ile Ile Asn Glu Gly Asp Ile Asn Thr Arg Arg Val Lys Ser
            245                 250                 255
Val Thr Phe Cys Ala Arg Ser Ile Pro His Met Leu Glu His Phe Arg
            260                 265                 270
Ala Gly Ser Leu Leu Val Thr Ser Ala Asp Arg Pro Asp Val Leu Val
            275                 280                 285
Ala Ala Cys Leu Ala Ala Met Asn Gly Val Glu Ile Gly Ala Leu Leu
            290                 295                 300
Leu Thr Gly Gly Tyr Glu Met Asp Ala Arg Ile Ser Lys Leu Cys Glu
305                 310                 315                 320
Arg Ala Phe Ala Thr Gly Leu Pro Val Phe Met Val Asn Thr Asn Thr
                    325                 330                 335
Trp Gln Thr Ser Leu Ser Leu Gln Ser Phe Asn Leu Glu Val Pro Val
            340                 345                 350
Asp Asp His Glu Arg Ile Glu Lys Val Gln Glu Tyr Val Ala Asn Tyr
            355                 360                 365
Ile Asn Ala Asp Trp Ile Glu Ser Leu Thr Ala Thr Ser Glu Arg Ser
370                 375                 380
Arg Arg Leu Ser Pro Pro Ala Phe Arg Tyr Gln Leu Thr Glu Leu Ala
385                 390                 395                 400
Arg Lys Ala Gly Lys Arg Ile Val Leu Pro Glu Gly Asp Glu Pro Arg
                    405                 410                 415
Thr Val Lys Ala Ala Ala Ile Cys Ala Glu Arg Gly Ile Ala Thr Cys
            420                 425                 430
Val Leu Leu Gly Asn Pro Ala Glu Ile Asn Arg Val Ala Ala Ser Gln
            435                 440                 445
Gly Val Glu Leu Gly Ala Gly Ile Glu Ile Val Asp Pro Glu Val Val
            450                 455                 460
Arg Glu Ser Tyr Val Gly Arg Leu Val Glu Leu Arg Lys Asn Lys Gly
465                 470                 475                 480
Met Thr Glu Thr Val Ala Arg Glu Gln Leu Glu Asp Asn Val Val Leu
                    485                 490                 495
Gly Thr Leu Met Leu Glu Gln Asp Glu Val Asp Gly Leu Val Ser Gly
            500                 505                 510
Ala Val His Thr Thr Ala Asn Thr Ile Arg Pro Pro Leu Gln Leu Ile
            515                 520                 525
Lys Thr Ala Pro Gly Ser Ser Leu Val Ser Ser Val Phe Phe Met Leu
            530                 535                 540
Leu Pro Glu Gln Val Tyr Val Tyr Gly Asp Cys Ala Ile Asn Pro Asp
545                 550                 555                 560
Pro Thr Ala Glu Gln Leu Ala Glu Ile Ala Ile Gln Ser Ala Asp Ser
                    565                 570                 575
Ala Ala Ala Phe Gly Ile Glu Pro Arg Val Ala Met Leu Ser Tyr Ser
            580                 585                 590
```

```
Thr Gly Thr Ser Gly Ala Gly Ser Asp Val Glu Lys Val Arg Glu Ala
        595                 600                 605

Thr Arg Leu Ala Gln Glu Lys Arg Pro Asp Leu Met Ile Asp Gly Pro
610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
        675                 680                 685

Asp Leu Ser Arg Gly Ala Leu Val Asp Asp Ile Val Tyr Thr Ile Ala
    690                 695                 700

Leu Thr Ala Ile Gln Ser Ala Gln Gln Gln
705                 710
```

<210> SEQ ID NO 13
<211> LENGTH: 1809
<212> TYPE: DNA
<213> ORGANISM: E.coli
<220> FEATURE:
<221> NAME/KEY: misc_feature
<222> LOCATION: (1)..(1809)
<223> OTHER INFORMATION: frdA

<400> SEQUENCE: 13

```
gtgcaaacct tcaagccga tcttgccatt gtaggcgccg gtggcgcggg attacgtgct      60
gcaattgctg ccgcgcaggc aaatccgaat gcaaaaatcg cactaatctc aaaagtatac     120
ccgatgcgta gccataccgt tgctgcagaa gggggctccg ccgctgtcgc gcaggatcat     180
gacagcttcg aatatcactt tcacgataca gtagcgggtg gcgactggtt gtgtgagcag     240
gatgtcgtgg attatttcgt ccaccactgc ccaaccgaaa tgacccaact ggaactgtgg     300
ggatgcccat ggagccgtcg cccggatggt agcgtcaacg tacgtcgctt cggcggcatg     360
aaaatcgagc gcacctggtt cgccgccgat aagaccggct tccatatgct gcacacgctg     420
ttccagacct ctctgcaatt cccgcagatc cagcgttttg acgaacattt cgtgctggat     480
attctggttg atgatggtca tgttcgcggc ctggtagcaa tgaacatgat ggaaggcacg     540
ctggtgcaga tccgtgctaa cgcggtcgtt atggctactg cggtgcgggt cgcgtttat      600 cgttacaaca ccaacggcgg catcgttacc ggtgacggta tgggtatggc gctaagccac     660
ggcgttccgc tgcgtgacat ggaattcgtt cagtatcacc caaccggtct gccaggttcc     720
ggtatcctga tgaccgaagg ctgccgcggt gaaggcggta ttctggtcaa caaaaatggc     780
taccgttatc tgcaagatta cggcatgggc ccggaaactc gctgggcga ccgaaaaac      840 aaatatatgg aactgggtcc acgcgacaaa gtttctcagg ccttctggca cgaatggcgt     900
aaaggcaaca ccatctccac gccgcgtggc gatgtggttt atctcgacct gcgtcacctc     960
ggcgagaaaa aactgcatga acgtctgccg ttcatctgcg aactggcgaa agcgtacgtt    1020
ggcgtcgatc cggttaaaga accgattccg gtacgtccga ccgcacacta ccccatgggc    1080
ggtatcgaaa ccgatcagaa ctgtgaaacc cgcattaaag gtctgttcgc cgtgggtgaa    1140
tgttcctctg ttggtctgca cggtgcaaac cgtctgggtt ctaactccct ggcggaactg    1200
gtggtcttcg gccgtctggc cggtgaacaa gcgacagagc gtgcagcaac tgccggtaat    1260
```

-continued

```
ggcaacgaag cggcaattga agcgcaggca gctggcgttg aacaacgtct gaaagatctg    1320
gttaaccagg atggcggcga aaactgggcg aagatccgcg acgaaatggg cctggcaatg    1380
gaagaaggtt gcggtatcta ccgtacgccg gaactgatgc agaaaaccat cgacaagctg    1440
gcagagctgc aggaacgctt caagcgcgtg cgcatcaccg acacctccag cgtgttcaac    1500
accgacctgc tctacaccat tgaactgggc cacggtctga cgttgctga atgtatggcg     1560 cactccgcaa tggcacgtaa agagtcccgc ggcgcacacc agcgtctgga cgaaggttgc    1620
accgagcgtg acgacgtcaa cttcctcaaa cacaccctcg ccttccgcga tgctgatggc    1680
acgactcgcc tggagtacag cgacgtgaag attactacgc tgccgccagc taaacgcgtt    1740
tacggtggcg aagcggatgc agccgataag gcggaagcag ccaataagaa ggagaaggcg    1800
aatggctga                                                             1809
```

```
<210> SEQ ID NO 14
<211> LENGTH: 602
<212> TYPE: PRT
<213> ORGANISM: E.coli
<220> FEATURE:
<221> NAME/KEY: MISC_FEATURE
<222> LOCATION: (1)..(602)
<223> OTHER INFORMATION: frdA

<400> SEQUENCE: 14

Met Gln Thr Phe Gln Ala Asp Leu Ala Ile Val Gly Ala Gly Gly Ala
1               5                   10                  15

Gly Leu Arg Ala Ala Ile Ala Ala Gln Ala Asn Pro Asn Ala Lys
            20                  25                  30

Ile Ala Leu Ile Ser Lys Val Tyr Pro Met Arg Ser His Thr Val Ala
        35                  40                  45

Ala Glu Gly Gly Ser Ala Ala Val Ala Gln Asp His Asp Ser Phe Glu
    50                  55                  60

Tyr His Phe His Asp Thr Val Ala Gly Gly Asp Trp Leu Cys Glu Gln
65                  70                  75                  80

Asp Val Val Asp Tyr Phe Val His His Cys Pro Thr Glu Met Thr Gln
                85                  90                  95

Leu Glu Leu Trp Gly Cys Pro Trp Ser Arg Arg Pro Asp Gly Ser Val
            100                 105                 110

Asn Val Arg Arg Phe Gly Gly Met Lys Ile Glu Arg Thr Trp Phe Ala
        115                 120                 125

Ala Asp Lys Thr Gly Phe His Met Leu His Thr Leu Phe Gln Thr Ser
    130                 135                 140

Leu Gln Phe Pro Gln Ile Gln Arg Phe Asp Glu His Phe Val Leu Asp
145                 150                 155                 160

Ile Leu Val Asp Asp Gly His Val Arg Gly Leu Val Ala Met Asn Met
                165                 170                 175

Met Glu Gly Thr Leu Val Gln Ile Arg Ala Asn Ala Val Val Met Ala
            180                 185                 190

Thr Gly Gly Ala Gly Arg Val Tyr Arg Tyr Asn Thr Asn Gly Gly Ile
        195                 200                 205

Val Thr Gly Asp Gly Met Gly Met Ala Leu Ser His Gly Val Pro Leu
    210                 215                 220

Arg Asp Met Glu Phe Val Gln Tyr His Pro Thr Gly Leu Pro Gly Ser
225                 230                 235                 240

Gly Ile Leu Met Thr Glu Gly Cys Arg Gly Glu Gly Gly Ile Leu Val
                245                 250                 255
```

Asn Lys Asn Gly Tyr Arg Tyr Leu Gln Asp Tyr Gly Met Pro Glu
            260                 265                 270

Thr Pro Leu Gly Glu Pro Lys Asn Lys Tyr Met Glu Leu Gly Pro Arg
        275                 280                 285

Asp Lys Val Ser Gln Ala Phe Trp His Glu Trp Arg Lys Gly Asn Thr
290                 295                 300

Ile Ser Thr Pro Arg Gly Asp Val Val Tyr Leu Asp Leu Arg His Leu
305                 310                 315                 320

Gly Glu Lys Lys Leu His Glu Arg Leu Pro Phe Ile Cys Glu Leu Ala
                325                 330                 335

Lys Ala Tyr Val Gly Val Asp Pro Val Lys Glu Pro Ile Pro Val Arg
            340                 345                 350

Pro Thr Ala His Tyr Thr Met Gly Gly Ile Glu Thr Asp Gln Asn Cys
        355                 360                 365

Glu Thr Arg Ile Lys Gly Leu Phe Ala Val Gly Glu Cys Ser Ser Val
370                 375                 380

Gly Leu His Gly Ala Asn Arg Leu Gly Ser Asn Ser Leu Ala Glu Leu
385                 390                 395                 400

Val Val Phe Gly Arg Leu Ala Gly Glu Gln Ala Thr Glu Arg Ala Ala
                405                 410                 415

Thr Ala Gly Asn Gly Asn Glu Ala Ala Ile Glu Ala Gln Ala Ala Gly
            420                 425                 430

Val Glu Gln Arg Leu Lys Asp Leu Val Asn Gln Asp Gly Gly Glu Asn
        435                 440                 445

Trp Ala Lys Ile Arg Asp Glu Met Gly Leu Ala Met Glu Glu Gly Cys
450                 455                 460

Gly Ile Tyr Arg Thr Pro Glu Leu Met Gln Lys Thr Ile Asp Lys Leu
465                 470                 475                 480

Ala Glu Leu Gln Glu Arg Phe Lys Arg Val Arg Ile Thr Asp Thr Ser
                485                 490                 495

Ser Val Phe Asn Thr Asp Leu Leu Tyr Thr Ile Glu Leu Gly His Gly
            500                 505                 510

Leu Asn Val Ala Glu Cys Met Ala His Ser Ala Met Ala Arg Lys Glu
        515                 520                 525

Ser Arg Gly Ala His Gln Arg Leu Asp Glu Gly Cys Thr Glu Arg Asp
530                 535                 540

Asp Val Asn Phe Leu Lys His Thr Leu Ala Phe Arg Asp Ala Asp Gly
545                 550                 555                 560

Thr Thr Arg Leu Glu Tyr Ser Asp Val Lys Ile Thr Thr Leu Pro Pro
                565                 570                 575

Ala Lys Arg Val Tyr Gly Gly Glu Ala Asp Ala Ala Asp Lys Ala Glu
            580                 585                 590

Ala Ala Asn Lys Lys Glu Lys Ala Asn Gly
        595                 600

<210> SEQ ID NO 15
<211> LENGTH: 1071
<212> TYPE: DNA
<213> ORGANISM: E. coli
<220> FEATURE:
<221> NAME/KEY: misc_feature
<222> LOCATION: (1)..(1071)
<223> OTHER INFORMATION: dadX

<400> SEQUENCE: 15

```
atgacccgtc cgatacaggc cagcctcgat ctgcaggcat taaaacagaa tctgtccatt      60
gtccgccagg ccgcgccgca cgcgcgcgtc tggtcggtgg taaaagcgaa cgcttacggg     120
catggtattg agcgtatctg gagcgcgctc ggggccaccg atggctttgc attacttaac     180
ctggaagagg caataacgtt acgtgagcgc ggctggaagg ggccgatcct gatgctggaa     240
ggattttttcc atgctcagga tctggagatt tatgaccagc accgcctgac cacctgcgta     300
cacagcaact ggcagctcaa agcactgcaa aatgcgcggc taaaagcacc gttggatatt     360
tatcttaaag tgaacagtgg gatgaatcgg ttgggcttcc agcccgatcg cgtgcttacc     420
gtctggcagc agttgcgggc aatggcgaat gttggcgaga tgaccctgat gtcgcatttt     480
gccgaagcgg aacatcctga tggaatttcc agcgcgatgg cgcgtattga gcaggcggcg     540
gaagggctgg agtgtcggcg ttcgttgtcc aattcggcgg cgactctgtg gcacccggaa     600
gcgcattttg actgggttcg gcctggcatt atttttgtatg gcgcttcgcc gtccggtcag     660
tggcgtgata tcgccaatac cggattacgt ccggtgatga cgctaagcag tgagattatt     720
ggtgtccaga cgctaaaagc gggtgagcgt gtgggctacg gcggtcgcta tactgcgcgc     780
gatgaacagc gaatcggcat tgtcgccgca gggtacgccg acggttatcc gcgccacgcg     840
cctaccggta cccctgtttt agtggacggc gtgcgcacca tgacggtggg gaccgtctcg     900
atggatatgc tagcggtcga tttaacgcct tgcccgcagg cggggattgg tacgccggtt     960
gagctgtggg gcaaggagat caaaattgat gatgtcgccg ccgctgccgg aacggtgggc    1020
tatgagttga tgtgcgcgct ggcgttacgc gtcccggttg tgacagtgta a             1071
```

<210> SEQ ID NO 16
<211> LENGTH: 356
<212> TYPE: PRT
<213> ORGANISM: E. coli
<220> FEATURE:
<221> NAME/KEY: MISC_FEATURE
<222> LOCATION: (1)..(356)
<223> OTHER INFORMATION: dadX

<400> SEQUENCE: 16

```
Met Thr Arg Pro Ile Gln Ala Ser Leu Asp Leu Gln Ala Leu Lys Gln
1               5                   10                  15

Asn Leu Ser Ile Val Arg Gln Ala Ala Pro His Ala Arg Val Trp Ser
            20                  25                  30

Val Val Lys Ala Asn Ala Tyr Gly His Gly Ile Glu Arg Ile Trp Ser
        35                  40                  45

Ala Leu Gly Ala Thr Asp Gly Phe Ala Leu Leu Asn Leu Glu Glu Ala
    50                  55                  60

Ile Thr Leu Arg Glu Arg Gly Trp Lys Gly Pro Ile Leu Met Leu Glu
65                  70                  75                  80

Gly Phe Phe His Ala Gln Asp Leu Glu Ile Tyr Asp Gln His Arg Leu
                85                  90                  95

Thr Thr Cys Val His Ser Asn Trp Gln Leu Lys Ala Leu Gln Asn Ala
            100                 105                 110

Arg Leu Lys Ala Pro Leu Asp Ile Tyr Leu Lys Val Asn Ser Gly Met
        115                 120                 125

Asn Arg Leu Gly Phe Gln Pro Asp Arg Val Leu Thr Val Trp Gln Gln
    130                 135                 140

Leu Arg Ala Met Ala Asn Val Gly Glu Met Thr Leu Met Ser His Phe
145                 150                 155                 160

Ala Glu Ala Glu His Pro Asp Gly Ile Ser Ser Ala Met Ala Arg Ile
```

```
                165                 170                 175
        Glu Gln Ala Ala Glu Gly Leu Glu Cys Arg Arg Ser Leu Ser Asn Ser
                    180                 185                 190

Ala Ala Thr Leu Trp His Pro Glu Ala His Phe Asp Trp Val Arg Pro
                    195                 200                 205

Gly Ile Ile Leu Tyr Gly Ala Ser Pro Ser Gly Gln Trp Arg Asp Ile
                    210                 215                 220

Ala Asn Thr Gly Leu Arg Pro Val Met Thr Leu Ser Ser Glu Ile Ile
        225                 230                 235                 240

Gly Val Gln Thr Leu Lys Ala Gly Glu Arg Val Gly Tyr Gly Gly Arg
                        245                 250                 255

Tyr Thr Ala Arg Asp Glu Gln Arg Ile Gly Ile Val Ala Ala Gly Tyr
                        260                 265                 270

Ala Asp Gly Tyr Pro Arg His Ala Pro Thr Gly Thr Pro Val Leu Val
                        275                 280                 285

Asp Gly Val Arg Thr Met Thr Val Gly Thr Val Ser Met Asp Met Leu
                        290                 295                 300

Ala Val Asp Leu Thr Pro Cys Pro Gln Ala Gly Ile Gly Thr Pro Val
        305                 310                 315                 320

Glu Leu Trp Gly Lys Glu Ile Lys Ile Asp Asp Val Ala Ala Ala Ala
                        325                 330                 335

Gly Thr Val Gly Tyr Glu Leu Met Cys Ala Leu Ala Leu Arg Val Pro
                        340                 345                 350

Val Val Thr Val
                355

<210> SEQ ID NO 17
<211> LENGTH: 450
<212> TYPE: DNA
<213> ORGANISM: E.coli
<220> FEATURE:
<221> NAME/KEY: misc_feature
<222> LOCATION: (1)..(450)
<223> OTHER INFORMATION: ygaW

<400> SEQUENCE: 17
atgttctcac cgcagtcacg cttgcgtcat gcagttgcag atacgttcgc gatggttgtt      60
tactgttctg tcgtgaacat gtgtattgaa gttttcctct ccggaatgag cttcgaacag     120
tctttttatt ccagattggt agcgattccg gtgaacatct taattgcatg gccatacggt     180
atgtaccgtg atctgtttat gcgcgcggca cgcaaagtta gcccgtcggg ctggataaaa     240
aatctggctg atatcctggc ttatgtgacg ttccagtcac cggtgtatgt ggcgatcttg     300
ttagtggtgg cgcagactg gcatcagatt atggcggcgg tcagttcaaa catcgttgtt     360
tcgatgttga tggggcggt ttatggctac ttcctcgatt attgccgccg actgtttaaa     420
gtcagccgtt accagcaggt aaaagcctga                                     450

<210> SEQ ID NO 18
<211> LENGTH: 149
<212> TYPE: PRT
<213> ORGANISM: E.coli
<220> FEATURE:
<221> NAME/KEY: MISC_FEATURE
<222> LOCATION: (1)..(149)
<223> OTHER INFORMATION: ygaW

<400> SEQUENCE: 18

Met Phe Ser Pro Gln Ser Arg Leu Arg His Ala Val Ala Asp Thr Phe
```

```
  1               5                  10                 15
Ala Met Val Val Tyr Cys Ser Val Val Asn Met Cys Ile Glu Val Phe
         20                 25                 30

Leu Ser Gly Met Ser Phe Glu Gln Ser Phe Tyr Ser Arg Leu Val Ala
         35                 40                 45

Ile Pro Val Asn Ile Leu Ile Ala Trp Pro Tyr Gly Met Tyr Arg Asp
         50                 55                 60

Leu Phe Met Arg Ala Ala Arg Lys Val Ser Pro Ser Gly Trp Ile Lys
 65                 70                 75                 80

Asn Leu Ala Asp Ile Leu Ala Tyr Val Thr Phe Gln Ser Pro Val Tyr
                 85                 90                 95

Val Ala Ile Leu Leu Val Val Gly Ala Asp Trp His Gln Ile Met Ala
             100                105                110

Ala Val Ser Ser Asn Ile Val Val Ser Met Leu Met Gly Ala Val Tyr
             115                120                125

Gly Tyr Phe Leu Asp Tyr Cys Arg Arg Leu Phe Lys Val Ser Arg Tyr
         130                135                140

Gln Gln Val Lys Ala
145
```

<210> SEQ ID NO 19
<211> LENGTH: 987
<212> TYPE: DNA
<213> ORGANISM: E.coli
<220> FEATURE:
<221> NAME/KEY: misc_feature
<222> LOCATION: (1)..(987)
<223> OTHER INFORMATION: zipA

<400> SEQUENCE: 19

```
atgatgcagg atttgcgtct gatattaatc attgttggcg cgatcgccat aatcgcttta      60
ctggtacatg gtttctggac cagccgtaaa gaacgatctt ctatgttccg cgatcggcca     120
ttaaaacgaa tgaagtcaaa acgtgacgac gattcttatg acgaggatgt cgaagatgat     180
gagggcgttg gtgaggttcg tgttcaccgc gtgaatcatg ccccggctaa cgctcaggag     240
catgaggctg ctcgtccgtc gccgcaacac cagtaccaac gccttatgc gtctgcgcag     300
ccgcgtcaac cggtccagca gccgcctgaa gcgcaggtac gccgcaaca tgctccgcgt     360
ccagcgcagc cggtgcagca gcctgccctat cagccgcagc ctgaacagcc gttgcagcag     420
ccagtttcgc cacaggtcgc gccagcgccg cagcctgtgc attcagcacc gcaaccggca     480
caacaggctt ccagcctgc agaacccgta gcggcaccac agcctgagcc tgtagcggaa     540
ccggctccag ttatggataa accgaagcgc aaagaagcgg tgattatcat gaacgtcgcg     600
gcgcatcacg gtagcgagct aaacggtgaa ctgcttctta acagcattca acaagcgggc     660
ttcattttg cgatatgaa tatttaccat cgtcatctta gcccggatgg cagcggcccg     720
gcgttattca gcctggcgaa tatggtgaaa ccgggaacct tgatcctga atgaaggat     780
ttcactactc cgggtgtcac catctttatg caggtaccgt cttacggtga cgagctgcag     840
aacttcaagc tgatgctgca atctgcgcag catattgccg atgaagtggg cggtgtcgtg     900
cttgacgatc agcgccgtat gatgactccg cagaaattgc gcgagtacca ggacatcatc     960
cgcgaagtca aagacgccaa cgcctga                                         987
```

<210> SEQ ID NO 20
<211> LENGTH: 328
<212> TYPE: PRT

<213> ORGANISM: E.coli
<220> FEATURE:
<221> NAME/KEY: MISC_FEATURE
<222> LOCATION: (1)..(328)
<223> OTHER INFORMATION: zipA

<400> SEQUENCE: 20

```
Met Met Gln Asp Leu Arg Leu Ile Leu Ile Ile Val Gly Ala Ile Ala
1               5                   10                  15
Ile Ile Ala Leu Leu Val His Gly Phe Trp Thr Ser Arg Lys Glu Arg
            20                  25                  30
Ser Ser Met Phe Arg Asp Arg Pro Leu Lys Arg Met Lys Ser Lys Arg
                35                  40                  45
Asp Asp Asp Ser Tyr Asp Glu Asp Val Glu Asp Asp Glu Gly Val Gly
        50                  55                  60
Glu Val Arg Val His Arg Val Asn His Ala Pro Ala Asn Ala Gln Glu
65                  70                  75                  80
His Glu Ala Ala Arg Pro Ser Pro Gln His Gln Tyr Gln Pro Pro Tyr
                85                  90                  95
Ala Ser Ala Gln Pro Arg Gln Pro Val Gln Gln Pro Pro Glu Ala Gln
            100                 105                 110
Val Pro Pro Gln His Ala Pro Arg Pro Ala Gln Pro Val Gln Gln Pro
        115                 120                 125
Ala Tyr Gln Pro Gln Pro Glu Gln Pro Leu Gln Gln Pro Val Ser Pro
130                 135                 140
Gln Val Ala Pro Ala Pro Gln Pro Val His Ser Ala Pro Gln Pro Ala
145                 150                 155                 160
Gln Gln Ala Phe Gln Pro Ala Glu Pro Val Ala Ala Pro Gln Pro Glu
                165                 170                 175
Pro Val Ala Glu Pro Ala Pro Val Met Asp Lys Pro Lys Arg Lys Glu
            180                 185                 190
Ala Val Ile Ile Met Asn Val Ala Ala His His Gly Ser Glu Leu Asn
        195                 200                 205
Gly Glu Leu Leu Leu Asn Ser Ile Gln Gln Ala Gly Phe Ile Phe Gly
    210                 215                 220
Asp Met Asn Ile Tyr His Arg His Leu Ser Pro Asp Gly Ser Gly Pro
225                 230                 235                 240
Ala Leu Phe Ser Leu Ala Asn Met Val Lys Pro Gly Thr Phe Asp Pro
                245                 250                 255
Glu Met Lys Asp Phe Thr Thr Pro Gly Val Thr Ile Phe Met Gln Val
            260                 265                 270
Pro Ser Tyr Gly Asp Glu Leu Gln Asn Phe Lys Leu Met Leu Gln Ser
        275                 280                 285
Ala Gln His Ile Ala Asp Glu Val Gly Gly Val Val Leu Asp Asp Gln
    290                 295                 300
Arg Arg Met Met Thr Pro Gln Lys Leu Arg Glu Tyr Gln Asp Ile Ile
305                 310                 315                 320
Arg Glu Val Lys Asp Ala Asn Ala
                325
```

<210> SEQ ID NO 21
<211> LENGTH: 1425
<212> TYPE: DNA
<213> ORGANISM: E.coli
<220> FEATURE:
<221> NAME/KEY: misc_feature
<222> LOCATION: (1)..(1425)

<223> OTHER INFORMATION: lpd

<400> SEQUENCE: 21

```
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
accgatattg acaagattcg tacctggaaa gagaaagtga tcaatcagct gaccggtggt     300
ctggctggta tggcgaaagg ccgcaaagtc aaagtggtca acggtctggg taaatttacc     360
ggggctaaca ccctggaagt tgaaggtgag aacggtaaaa ccgtgatcaa cttcgacaac     420
gcgatcattg cagcgggttc tcgcccgatc caactgccgt ttattccgca tgaagatccg     480
cgtatctggg actccactga cgcgctgaaa ctgaagaag taccagaacg cctgctggta     540
atgggtggcg gtatcatcgg tctggaaatg ggcaccgtat accacgcgct gggttcacag     600
attgacgtgg ttgaaatgtt cgaccaggtt atcccggcag ctgacaaaga catcgttaaa     660
gtcttcacca gcgtatcag caagaaattc aacctgatgc tggaaaccaa agttaccgcc     720
gttgaagcga agaagacgg tatttatgtg acgatggaag gcaaaaaagc acccgctgaa     780
ccgcagcgtt acgacgccgt gctggtagcg attggtcgtg tgccgaacgg taaaaacctc     840
gacgcaggca agctggcgt ggaagtggac gaccgtggtt tcatccgcgt tgacaaacag     900
ctgcgtacca acgtaccgca catctttgct atcggcgata tcgtcggtca gccgatgctg     960
gcacacaaag tgttcacga aggtcacgtt gccgctgaag ttatcgccgg taagaaacac    1020
tacttcgatc cgaaagttat cccgtccatc gcctataccg aaccagaagt tgcatgggta    1080
ggtctgactg agaagaagc gaaagagaaa ggcatcagct atgaaaccgc caccttcccg    1140
tgggctgctt ctggtcgtgc tatcgcttcc gactgcgcag acggtatgac caagctgatt    1200
ttcgacaaag aatctcaccg tgtgatcggt ggtgcgattg tcggtaccaa cggcggcgag    1260
ctgctgggtg aaatcggcct ggcaatcgaa atgggttgtg atgctgaaga catcgcactg    1320
accatccacg cgcacccgac tctgcacgag tctgtgggcc tggcggcaga agtgttcgaa    1380
ggtagcatta ccgacctgcc gaacccgaaa gcgaagaaga agtaa                   1425
```

<210> SEQ ID NO 22
<211> LENGTH: 474
<212> TYPE: PRT
<213> ORGANISM: E.coli
<220> FEATURE:
<221> NAME/KEY: MISC_FEATURE
<222> LOCATION: (1)..(474)
<223> OTHER INFORMATION: lpd

<400> SEQUENCE: 22

```
Met Ser Thr Glu Ile Lys Thr Gln Val Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80
```

```
Thr Asp Ile Asp Lys Ile Arg Thr Trp Lys Glu Lys Val Ile Asn Gln
             85                   90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
            130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Ile Ile Gly Leu Glu Met Gly Thr
                180                 185                 190

Val Tyr His Ala Leu Gly Ser Gln Ile Asp Val Val Glu Met Phe Asp
            195                 200                 205

Gln Val Ile Pro Ala Ala Asp Lys Asp Ile Val Lys Val Phe Thr Lys
            210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
                260                 265                 270

Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
            290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
            370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
            435                 440                 445

His Glu Ser Val Gly Leu Ala Ala Glu Val Phe Glu Gly Ser Ile Thr
            450                 455                 460

Asp Leu Pro Asn Pro Lys Ala Lys Lys Lys
465                 470

<210> SEQ ID NO 23
<211> LENGTH: 1320
<212> TYPE: DNA
```

<213> ORGANISM: E. coli
<220> FEATURE:
<221> NAME/KEY: misc_feature
<222> LOCATION: (1)..(1320)
<223> OTHER INFORMATION: brnQ

<400> SEQUENCE: 23

```
atgacccatc aattaagatc gcgcgatatc atcgctctgg gctttatgac atttgcgttg      60
ttcgtcggcg caggtaacat tatttttccct ccaatggtcg gcttgcaggc aggcgaacac    120
gtctggactg cggcattcgg cttcctcatt actgccgttg gcctgccggt attaacggta    180
gtggcgctgg caaaagttgg cggcggtgtt gacagcctca gcacgccaat cggtaaagtc    240
gctggcgtgc tgctggcaac ggtttgttac ctggcggtgg ggccgctttt cgctacgccg    300
cgtacagcta ccgtttcctt tgaagtgggg attgcgccgc tgacgggtga ttccgcgctg    360
ccgctgttta tctacagcct ggtctatttc gctatcgtta ttctggtttc gctctatccg    420
ggcaagctgc tggataccgt gggcaacttc cttgcgccgc tgaaaattat cgcgctggtc    480
atcctgtctg ttgccgcgat tgtctggccg gcgggttcta tcagcacggc gactgaggct    540
tatcaaaacg ctgcgttttc taacggcttc gttaacggct atctgaccat ggatacgctg    600
ggcgcaatgg tgtttggtat cgttattgtt aacgcggcg gttctcgtgg cgttaccgaa    660
gcgcgtctgc tgacccgtta taccgtctgg gctggcctga tggcgggtgt tggtctgact    720
ctgctgtacc tggcgctgtt ccgtctgggt tcagacagcg cgtcgctggt cgatcagtct    780
gcaaacggcg ctgctattct gcatgcttac gttcagcaca cctttggcgg cggcggtagc    840
ttcctgctgg cggcgttaat cttcatcgcc tgcctggtaa cggcagttgg cctgacctgt    900
gcttgtgcag aattctttgc ccagtacgta ccgctctctt atcgtacgct ggtgtttatc    960
ctcggcggct tctcgatggt ggtttctaac ctcggcttaa gccagctgat ccagatctcc   1020
gtaccggtgc tgaccgctat ttatccgccg tgtatcgcac tggttgtatt aagttttaca   1080
cgctcatggt ggcataattc gtcccgcgtg attgctccgc cgatgtttat cagcctgctt   1140
tttggtattc tcgacgggat caaagcatct gcattcagcg atatcttacc gtcctgggcg   1200
cagcgtttac cgctggccga acaaggtctg cgtggttaa tgccaacagt ggtgatggtg   1260
gttctggcca ttatctggga tcgcgcggca ggtcgtcagg tgacctccag cgctcactaa   1320
```

<210> SEQ ID NO 24
<211> LENGTH: 439
<212> TYPE: PRT
<213> ORGANISM: E. coli
<220> FEATURE:
<221> NAME/KEY: MISC_FEATURE
<222> LOCATION: (1)..(439)
<223> OTHER INFORMATION: brnQ

<400> SEQUENCE: 24

```
Met Thr His Gln Leu Arg Ser Arg Asp Ile Ile Ala Leu Gly Phe Met
1               5                   10                  15

Thr Phe Ala Leu Phe Val Gly Ala Gly Asn Ile Ile Phe Pro Pro Met
            20                  25                  30

Val Gly Leu Gln Ala Gly Glu His Val Trp Thr Ala Ala Phe Gly Phe
        35                  40                  45

Leu Ile Thr Ala Val Gly Leu Pro Val Leu Thr Val Ala Leu Ala
    50                  55                  60

Lys Val Gly Gly Gly Val Asp Ser Leu Ser Thr Pro Ile Gly Lys Val
65                  70                  75                  80
```

Ala Gly Val Leu Leu Ala Thr Val Cys Tyr Leu Ala Val Gly Pro Leu
            85                  90                  95

Phe Ala Thr Pro Arg Thr Ala Thr Val Ser Phe Glu Val Gly Ile Ala
        100                 105                 110

Pro Leu Thr Gly Asp Ser Ala Leu Pro Leu Phe Ile Tyr Ser Leu Val
    115                 120                 125

Tyr Phe Ala Ile Val Ile Leu Val Ser Leu Tyr Pro Gly Lys Leu Leu
130                 135                 140

Asp Thr Val Gly Asn Phe Leu Ala Pro Leu Lys Ile Ala Leu Val
145                 150                 155                 160

Ile Leu Ser Val Ala Ala Ile Val Trp Pro Ala Gly Ser Ile Ser Thr
                165                 170                 175

Ala Thr Glu Ala Tyr Gln Asn Ala Ala Phe Ser Asn Gly Phe Val Asn
            180                 185                 190

Gly Tyr Leu Thr Met Asp Thr Leu Gly Ala Met Val Phe Gly Ile Val
        195                 200                 205

Ile Val Asn Ala Ala Arg Ser Arg Gly Val Thr Glu Ala Arg Leu Leu
    210                 215                 220

Thr Arg Tyr Thr Val Trp Ala Gly Leu Met Ala Gly Val Gly Leu Thr
225                 230                 235                 240

Leu Leu Tyr Leu Ala Leu Phe Arg Leu Gly Ser Asp Ser Ala Ser Leu
                245                 250                 255

Val Asp Gln Ser Ala Asn Gly Ala Ala Ile Leu His Ala Tyr Val Gln
            260                 265                 270

His Thr Phe Gly Gly Gly Ser Phe Leu Leu Ala Ala Leu Ile Phe
        275                 280                 285

Ile Ala Cys Leu Val Thr Ala Val Gly Leu Thr Cys Ala Cys Ala Glu
    290                 295                 300

Phe Phe Ala Gln Tyr Val Pro Leu Ser Tyr Arg Thr Leu Val Phe Ile
305                 310                 315                 320

Leu Gly Gly Phe Ser Met Val Val Ser Asn Leu Gly Leu Ser Gln Leu
                325                 330                 335

Ile Gln Ile Ser Val Pro Val Leu Thr Ala Ile Tyr Pro Pro Cys Ile
            340                 345                 350

Ala Leu Val Val Leu Ser Phe Thr Arg Ser Trp Trp His Asn Ser Ser
        355                 360                 365

Arg Val Ile Ala Pro Pro Met Phe Ile Ser Leu Leu Phe Gly Ile Leu
    370                 375                 380

Asp Gly Ile Lys Ala Ser Ala Phe Ser Asp Ile Leu Pro Ser Trp Ala
385                 390                 395                 400

Gln Arg Leu Pro Leu Ala Glu Gln Gly Leu Ala Trp Leu Met Pro Thr
                405                 410                 415

Val Val Met Val Val Leu Ala Ile Ile Trp Asp Arg Ala Ala Gly Arg
            420                 425                 430

Gln Val Thr Ser Ser Ala His
        435

<210> SEQ ID NO 25
<211> LENGTH: 1104
<212> TYPE: DNA
<213> ORGANISM: E. coli
<220> FEATURE:
<221> NAME/KEY: misc_feature
<222> LOCATION: (1)..(1104)
<223> OTHER INFORMATION: asd

<400> SEQUENCE: 25

```
atgaaaaatg ttggttttat cggctggcgc ggtatggtcg gctccgttct catgcaacgc        60
atggttgaag agcgcgactt cgacgccatt cgccctgtct tcttttctac ttctcagctt       120
ggccaggctg cgccgtcttt tggcggaacc actggcacac ttcaggatgc ctttgatctg       180
gaggcgctaa aggccctcga tatcattgtg acctgtcagg gcggcgatta taccaacgaa       240
atctatccaa agcttcgtga agcggatgg caaggttact ggattgacgc agcatcgtct        300
ctgcgcatga agatgacgc catcatcatt cttgaccccg tcaatcagga cgtcattacc        360
gacggattaa ataatggcat caggactttt gttggcggta actgtaccgt aagcctgatg       420
ttgatgtcgt tgggtggttt attcgccaat gatcttgttg attgggtgtc cgttgcaacc       480
taccaggccg cttccggcgg tggtgcgcga catatgcgtg agttattaac ccagatgggc       540
catctgtatg ccatgtggc agatgaactc gcgaccccgt cctctgctat tctcgatatc        600
gaacgcaaag tcacaacctt aacccgtagc ggtgagctgc cggtggataa ctttggcgtg       660
ccgctggcgg gtagcctgat tccgtggatc gacaaacagc tcgataacgg tcagagccgc       720
gaagagtgga agggcaggc ggaaaccaac aagatcctca acacatcttc cgtaattccg        780
gtagatggtt tatgtgtgcg tgtcggggca ttgcgctgcc acagccaggc attcactatt       840
aaattgaaaa aagatgtgtc tattccgacc gtggaagaac tgctggctgc gcacaatccg       900
tgggcgaaag tcgttccgaa cgatcgggaa atcactatgc gtgagctaac ccagctgcc        960
gttaccggca cgctgaccac gccggtaggc cgcctgcgta agctgaatat gggaccagag      1020
ttcctgtcag cctttaccgt gggcgaccag ctgctgtggg gggccgcgga gccgctgcgt      1080
cggatgcttc gtcaactggc gtaa                                              1104
```

<210> SEQ ID NO 26
<211> LENGTH: 367
<212> TYPE: PRT
<213> ORGANISM: E. coli
<220> FEATURE:
<221> NAME/KEY: MISC_FEATURE
<222> LOCATION: (1)..(367)
<223> OTHER INFORMATION: asd

<400> SEQUENCE: 26

```
Met Lys Asn Val Gly Phe Ile Gly Trp Arg Gly Met Val Gly Ser Val
1               5                   10                  15

Leu Met Gln Arg Met Val Glu Glu Arg Asp Phe Asp Ala Ile Arg Pro
            20                  25                  30

Val Phe Phe Ser Thr Ser Gln Leu Gly Gln Ala Ala Pro Ser Phe Gly
        35                  40                  45

Gly Thr Thr Gly Thr Leu Gln Asp Ala Phe Asp Leu Glu Ala Leu Lys
    50                  55                  60

Ala Leu Asp Ile Ile Val Thr Cys Gln Gly Gly Asp Tyr Thr Asn Glu
65                  70                  75                  80

Ile Tyr Pro Lys Leu Arg Glu Ser Gly Trp Gln Gly Tyr Trp Ile Asp
                85                  90                  95

Ala Ala Ser Ser Leu Arg Met Lys Asp Asp Ala Ile Ile Ile Leu Asp
            100                 105                 110

Pro Val Asn Gln Asp Val Ile Thr Asp Gly Leu Asn Asn Gly Ile Arg
        115                 120                 125

Thr Phe Val Gly Gly Asn Cys Thr Val Ser Leu Met Leu Met Ser Leu
    130                 135                 140
```

```
Gly Gly Leu Phe Ala Asn Asp Leu Val Asp Trp Val Ser Val Ala Thr
145                 150                 155                 160

Tyr Gln Ala Ala Ser Gly Gly Ala Arg His Met Arg Glu Leu Leu
            165                 170                 175

Thr Gln Met Gly His Leu Tyr Gly His Val Ala Asp Glu Leu Ala Thr
            180                 185                 190

Pro Ser Ser Ala Ile Leu Asp Ile Glu Arg Lys Val Thr Thr Leu Thr
            195                 200                 205

Arg Ser Gly Glu Leu Pro Val Asp Asn Phe Gly Val Pro Leu Ala Gly
            210                 215                 220

Ser Leu Ile Pro Trp Ile Asp Lys Gln Leu Asp Asn Gly Gln Ser Arg
225                 230                 235                 240

Glu Glu Trp Lys Gly Gln Ala Glu Thr Asn Lys Ile Leu Asn Thr Ser
                245                 250                 255

Ser Val Ile Pro Val Asp Gly Leu Cys Val Arg Val Gly Ala Leu Arg
                260                 265                 270

Cys His Ser Gln Ala Phe Thr Ile Lys Leu Lys Lys Asp Val Ser Ile
            275                 280                 285

Pro Thr Val Glu Glu Leu Leu Ala Ala His Asn Pro Trp Ala Lys Val
290                 295                 300

Val Pro Asn Asp Arg Glu Ile Thr Met Arg Glu Leu Thr Pro Ala Ala
305                 310                 315                 320

Val Thr Gly Thr Leu Thr Thr Pro Val Gly Arg Leu Arg Lys Leu Asn
                325                 330                 335

Met Gly Pro Glu Phe Leu Ser Ala Phe Thr Val Gly Asp Gln Leu Leu
            340                 345                 350

Trp Gly Ala Ala Glu Pro Leu Arg Arg Met Leu Arg Gln Leu Ala
            355                 360                 365

<210> SEQ ID NO 27
<211> LENGTH: 1026
<212> TYPE: DNA
<213> ORGANISM: E. coli
<220> FEATURE:
<221> NAME/KEY: misc_feature
<222> LOCATION: (1)..(1026)
<223> OTHER INFORMATION: lpxD mutated

<400> SEQUENCE: 27
atgccttcaa ttcgactggc tgatttagcg cagcagttgg atacagaact acacggtgat      60
ggcgatatcg tcatcaccgg cgttgcgtcc atgcaatctg cacaaacagg tcacattacg     120
ttcatggtta acccaaaata ccgtgagcat ttaggcttgt gccaggcgtc cgcggttgtc     180
atgacccagg acgatcttcc tttcgcgaaa agtgccgcgc tggtagtgaa gaatccctac     240
ctgacttacg cgcgcatggc gcaaatttta gataccacgc cgcagcccgc gcagaacatt     300
gcacccagtg cggtgatcga cgcgacggcg aagctgggta acaacgtatc gattggcgct     360
aacgcggtga ttgagtccgg cgttgaactg ggcgataacg tgattatcgg tgccggttgc     420
ttcgtaggta aaacagcaa atcggtgca ggttcgcgtc tctgggcgaa cgtaaccatt     480
taccatgaga tccagatcgg tcagaattgc ctgatccagt ccggaacagt ggtaggcgca     540
gacggctttg ttatgccaa cgatcgtggt aactgggtga agatcccaca gattggtcgc     600
gtaattattg gcgatcgcgt ggagatcggt gcctgcacaa ccatcgatcg cggcgcgctg     660
gatgacacta ttattggcaa tggcgtgatc attgataacc agtgccagat tgcacataac     720
gtcgtgattg gcgacaatac ggcggttgcc ggtggcgtca ttatggcggg cagcctgaaa     780
```

```
attggtcgtt actgcatgat cggcggagcc agcgtaatca acgggcatat ggaaatatgc    840
gacaaagtga cggttacggg catgggtatg gtgatgcgtc ccatcactga accaggcgtc    900
tattcctcag gcattccgct gcaacccaac aaagtctggc gcaaaaccgc tgcactggtg    960
atgaacattg atgacatgag caagcgtctg aaatcgcttg agcgcaaggt taatcaacaa   1020
gactaa                                                              1026
```

<210> SEQ ID NO 28
<211> LENGTH: 341
<212> TYPE: PRT
<213> ORGANISM: E. coli
<220> FEATURE:
<221> NAME/KEY: MISC_FEATURE
<222> LOCATION: (1)..(341)
<223> OTHER INFORMATION: lpxD mutated

<400> SEQUENCE: 28

```
Met Pro Ser Ile Arg Leu Ala Asp Leu Ala Gln Gln Leu Asp Thr Glu
1               5                   10                  15

Leu His Gly Asp Gly Asp Ile Val Ile Thr Gly Val Ala Ser Met Gln
            20                  25                  30

Ser Ala Gln Thr Gly His Ile Thr Phe Met Val Asn Pro Lys Tyr Arg
        35                  40                  45

Glu His Leu Gly Leu Cys Gln Ala Ser Ala Val Val Met Thr Gln Asp
    50                  55                  60

Asp Leu Pro Phe Ala Lys Ser Ala Ala Leu Val Val Lys Asn Pro Tyr
65                  70                  75                  80

Leu Thr Tyr Ala Arg Met Ala Gln Ile Leu Asp Thr Thr Pro Gln Pro
                85                  90                  95

Ala Gln Asn Ile Ala Pro Ser Ala Val Ile Asp Ala Thr Ala Lys Leu
            100                 105                 110

Gly Asn Asn Val Ser Ile Gly Ala Asn Ala Val Ile Glu Ser Gly Val
        115                 120                 125

Glu Leu Gly Asp Asn Val Ile Ile Gly Ala Gly Cys Phe Val Gly Lys
    130                 135                 140

Asn Ser Lys Ile Gly Ala Gly Ser Arg Leu Trp Ala Asn Val Thr Ile
145                 150                 155                 160

Tyr His Glu Ile Gln Ile Gly Gln Asn Cys Leu Ile Gln Ser Gly Thr
                165                 170                 175

Val Val Gly Ala Asp Gly Phe Gly Tyr Ala Asn Asp Arg Gly Asn Trp
            180                 185                 190

Val Lys Ile Pro Gln Ile Gly Arg Val Ile Ile Gly Asp Arg Val Glu
        195                 200                 205

Ile Gly Ala Cys Thr Thr Ile Asp Arg Gly Ala Leu Asp Asp Thr Ile
    210                 215                 220

Ile Gly Asn Gly Val Ile Ile Asp Asn Gln Cys Gln Ile Ala His Asn
225                 230                 235                 240

Val Val Ile Gly Asp Asn Thr Ala Val Ala Gly Val Ile Met Ala
                245                 250                 255

Gly Ser Leu Lys Ile Gly Arg Tyr Cys Met Ile Gly Gly Ala Ser Val
            260                 265                 270

Ile Asn Gly His Met Glu Ile Cys Asp Lys Val Thr Val Thr Gly Met
        275                 280                 285

Gly Met Val Met Arg Pro Ile Thr Glu Pro Gly Val Tyr Ser Ser Gly
    290                 295                 300
```

```
Ile Pro Leu Gln Pro Asn Lys Val Trp Arg Lys Thr Ala Ala Leu Val
305                 310                 315                 320

Met Asn Ile Asp Asp Met Ser Lys Arg Leu Lys Ser Leu Glu Arg Lys
            325                 330                 335

Val Asn Gln Gln Asp
            340
```

<210> SEQ ID NO 29
<211> LENGTH: 918
<212> TYPE: DNA
<213> ORGANISM: E. coli
<220> FEATURE:
<221> NAME/KEY: misc_feature
<222> LOCATION: (1)..(918)
<223> OTHER INFORMATION: gcvA

<400> SEQUENCE: 29

```
atgtctaaac gattaccacc gctaaatgcc ttacgagttt ttgatgccgc agcacgccat      60
ttaagtttca ctcgcgcagc agaagagctt tttgtgaccc aggccgcagt aagtcatcaa     120
atcaagtctc ttgaggattt tctggggcta aaactgttcc gccgccgtaa tcgttcactc     180
ctgctgaccg aggaaggtca agctatttc ctcgatatca aagagatatt ttcgcaatta     240
accgaagcga cgcgtaaact ccaggcccgt agcgccaagg gggcgttgac ggtcagttta     300
ctccccagtt tcgccattca ttggttggtt ccgcgacttt ccagctttaa ttcagcttat     360
ccgggaattg acgttcgaat ccaggcggtt gatcgtcagg aagataagct ggcggatgat     420
gttgatgtgg cgatatttta tggtcggggc aactggccgg gctacgggt ggaaaaactg     480
tacgccgaat atttattgcc ggtgtgttcg ccgctactgc tgacaggcga aaacccttg     540
aagaccccgg aagatctggc taaacatacg ttattacatg atgcgtcacg ccgtgactgg     600
cagacatata cccgacagtt gggggttaaat catatcaacg ttcagcaagg gccaattttt     660
agtcatagcg ccatggtgct gcaagcggct attcacgggc agggagtggc gctggcaaat     720
aacgtgatgg cgcaatctga atcgaggcc ggacgtcttg tttgcccgtt taatgatgtt     780
ctggtcagta aaaacgcttt ttatctggtt tgtcatgaca gccaggcaga actgggtaaa     840
atagccgcct ttcgccaatg gatcctggcg aaagccgctg ctgaacaaga aaaattccgc     900
tttcgttatg aacaataa                                                  918
```

<210> SEQ ID NO 30
<211> LENGTH: 305
<212> TYPE: PRT
<213> ORGANISM: E. coli
<220> FEATURE:
<221> NAME/KEY: MISC_FEATURE
<222> LOCATION: (1)..(305)
<223> OTHER INFORMATION: gcvA

<400> SEQUENCE: 30

```
Met Ser Lys Arg Leu Pro Pro Leu Asn Ala Leu Arg Val Phe Asp Ala
1               5                   10                  15

Ala Ala Arg His Leu Ser Phe Thr Arg Ala Ala Glu Glu Leu Phe Val
            20                  25                  30

Thr Gln Ala Ala Val Ser His Gln Ile Lys Ser Leu Glu Asp Phe Leu
        35                  40                  45

Gly Leu Lys Leu Phe Arg Arg Arg Asn Arg Ser Leu Leu Leu Thr Glu
    50                  55                  60

Glu Gly Gln Ser Tyr Phe Leu Asp Ile Lys Glu Ile Phe Ser Gln Leu
```

```
            65                  70                  75                  80
Thr Glu Ala Thr Arg Lys Leu Gln Ala Arg Ser Ala Lys Gly Ala Leu
                85                  90                  95

Thr Val Ser Leu Leu Pro Ser Phe Ala Ile His Trp Leu Val Pro Arg
            100                 105                 110

Leu Ser Ser Phe Asn Ser Ala Tyr Pro Gly Ile Asp Val Arg Ile Gln
            115                 120                 125

Ala Val Asp Arg Gln Glu Asp Lys Leu Ala Asp Val Asp Val Ala
        130                 135                 140

Ile Phe Tyr Gly Arg Gly Asn Trp Pro Gly Leu Arg Val Glu Lys Leu
145                 150                 155                 160

Tyr Ala Glu Tyr Leu Leu Pro Val Cys Ser Pro Leu Leu Leu Thr Gly
                165                 170                 175

Glu Lys Pro Leu Lys Thr Pro Glu Asp Leu Ala Lys His Thr Leu Leu
            180                 185                 190

His Asp Ala Ser Arg Arg Asp Trp Gln Thr Tyr Thr Arg Gln Leu Gly
            195                 200                 205

Leu Asn His Ile Asn Val Gln Gln Gly Pro Ile Phe Ser His Ser Ala
        210                 215                 220

Met Val Leu Gln Ala Ala Ile His Gly Gln Gly Val Ala Leu Ala Asn
225                 230                 235                 240

Asn Val Met Ala Gln Ser Glu Ile Glu Ala Gly Arg Leu Val Cys Pro
                245                 250                 255

Phe Asn Asp Val Leu Val Ser Lys Asn Ala Phe Tyr Leu Val Cys His
            260                 265                 270

Asp Ser Gln Ala Glu Leu Gly Lys Ile Ala Ala Phe Arg Gln Trp Ile
        275                 280                 285

Leu Ala Lys Ala Ala Ala Glu Gln Glu Lys Phe Arg Phe Arg Tyr Glu
                290                 295                 300

Gln
305

<210> SEQ ID NO 31
<211> LENGTH: 206
<212> TYPE: DNA
<213> ORGANISM: E. coli
<220> FEATURE:
<221> NAME/KEY: misc_feature
<222> LOCATION: (1)..(206)
<223> OTHER INFORMATION: gcvB

<400> SEQUENCE: 31
acttcctgag ccggaacgaa aagttttatc ggaatgcgtg ttctggtgaa ctttttggctt      60 acggttgtga tgttgtgttg ttgtgttttgc aattggtctg cgattcagac catggtagca    120
aagctacctt ttttcacttc ctgtacattt accctgtctg tccatagtga ttaatgtagc    180
accgcctaat tgcggtgctt tttttt                                           206

<210> SEQ ID NO 32
<211> LENGTH: 1203
<212> TYPE: DNA
<213> ORGANISM: Escherichia coli
<220> FEATURE:
<221> NAME/KEY: misc_feature
<222> LOCATION: (1)..(1203)
<223> OTHER INFORMATION: ackA

<400> SEQUENCE: 32
```

```
atgtcgagta agttagtact ggttctgaac tgcggtagtt cttcactgaa atttgccatc      60
atcgatgcag taaatggtga agagtacctt tctggtttag ccgaatgttt ccacctgccc     120
gaagcacgta tcaaatggaa aatggacggc aataaacagg aagcggcttt aggtgcaggc     180
gccgctcaca gcgaagcgct caactttatc gttaatacta ttctggcaca aaaaccagaa     240
ctgtctgcgc agctgactgc tatcggtcac cgtatcgtac acggcggcga aaagtatacc     300
agctccgtag tgatcgatga gtctgttatt cagggtatca agatgcagc ttcttttgca      360
ccgctgcaca acccggctca cctgatcggt atcgaagaag ctctgaaatc tttcccacag     420
ctgaaagaca aaaacgttgc tgtatttgac accgcgttcc accagactat gccggaagag     480
tcttacctct acgccctgcc ttacaacctg tacaagagc acggcatccg tcgttacggc      540
gcgcacggca ccagccactt ctatgtaacc caggaagcgg caaaaatgct gaacaaaccg     600
gtagaagaac tgaacatcat cacctgccac ctgggcaacg gtggttccgt ttctgctatc     660
cgcaacggta atgcgttga cacctctatg ggcctgaccc cgctggaagg tctggtcatg      720
ggtacccgtt ctggtgatat cgatccggcg atcatcttcc acctgcacga cacccctgggc    780
atgagcgttg acgcaatcaa caaactgctg accaaagagt ctggcctgct gggtctgacc     840
gaagtgacca gcgactgccg ctatgttgaa gacaactacg cgacgaaaga agacgcgaag     900
cgcgcaatgg acgtttactg ccaccgcctg gcgaaataca tcggtgccta cactgcgctg     960
atggatggtc gtctggacgc tgttgtattc actggtggta tcggtgaaaa tgccgcaatg    1020
gttcgtgaac tgtctctggg caaactgggc gtgctgggct ttgaagttga tcatgaacgc    1080
aacctggctg cacgtttcgg caaatctggt ttcatcaaca aagaaggtac ccgtcctgcg    1140
gtggttatcc caaccaacga gaactggtt atcgcgcaag acgcgagccg cctgactgcc     1200
tga                                                                   1203
```

<210> SEQ ID NO 33
<211> LENGTH: 400
<212> TYPE: PRT
<213> ORGANISM: Escherichia coli
<220> FEATURE:
<221> NAME/KEY: MISC_FEATURE
<222> LOCATION: (1)..(400)
<223> OTHER INFORMATION: ackA

<400> SEQUENCE: 33

```
Met Ser Ser Lys Leu Val Leu Val Leu Asn Cys Gly Ser Ser Ser Leu
1               5                  10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
```

```
                130             135             140
Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
                180                 185                 190

Ala Ala Lys Met Leu Asn Lys Pro Val Glu Glu Leu Asn Ile Ile Thr
                195                 200                 205

Cys His Leu Gly Asn Gly Gly Ser Val Ser Ala Ile Arg Asn Gly Lys
                210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
                260                 265                 270

Glu Ser Gly Leu Leu Gly Leu Thr Glu Val Thr Ser Asp Cys Arg Tyr
                275                 280                 285

Val Glu Asp Asn Tyr Ala Thr Lys Glu Asp Ala Lys Arg Ala Met Asp
290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
                340                 345                 350

Gly Phe Glu Val Asp His Glu Arg Asn Leu Ala Ala Arg Phe Gly Lys
                355                 360                 365

Ser Gly Phe Ile Asn Lys Glu Gly Thr Arg Pro Ala Val Val Ile Pro
                370                 375                 380

Thr Asn Glu Glu Leu Val Ile Ala Gln Asp Ala Ser Arg Leu Thr Ala
385                 390                 395                 400

<210> SEQ ID NO 34
<211> LENGTH: 5003
<212> TYPE: DNA
<213> ORGANISM: Artificial
<220> FEATURE:
<223> OTHER INFORMATION: Plasmid pACYC-asd
<220> FEATURE:
<221> NAME/KEY: misc_feature
<222> LOCATION: (1)..(5003)
<223> OTHER INFORMATION: Plasmid pACYC-asd

<400> SEQUENCE: 34
gaattccgga tgagcattca tcaggcgggc aagaatgtga ataaaggccg gataaaactt    60
gtgcttattt ttctttacgg tctttaaaaa ggccgtaata tccagctgaa cggtctggtt   120
ataggtacat tgagcaactg actgaaatgc ctcaaaatgt tctttacgat gccattggga   180
tatatcaacg gtggtatatc cagtgatttt tttctccatt ttagcttcct tagctcctga   240
aaatctcgat aactcaaaaa atacgcccgg tagtgatctt atttcattat ggtgaaagtt   300
ggaacctctt acgtgccgat caacgtctca ttttcgccaa agttggccc agggcttccc   360 ggtatcaaca gggacaccag gatttattta ttctgcgaag tgatcttccg tcacaggtat   420
ttattcggcg caaagtgcgt cgggtgatgc tgccaactta ctgatttagt gtatgatggt   480
```

```
gttttttgagg tgctccagtg gcttctgttt ctatcagctg tccctcctgt tcagctactg      540
acggggtggt gcgtaacggc aaaagcaccg ccggacatca gcgctagcgg agtgtatact      600
ggcttactat gttggcactg atgagggtgt cagtgaagtg cttcatgtgg caggagaaaa      660
aaggctgcac cggtgcgtca gcagaatatg tgatacagga tatattccgc ttcctcgctc      720
actgactcgc tacgctcggt cgttcgactg cggcgagcgg aaatggctta cgaacggggc      780
ggagatttcc tggaagatgc caggaagata cttaacaggg aagtgagagg gccgcggcaa      840
agccgttttt ccataggctc cgccccctg acaagcatca cgaaatctga cgctcaaatc       900
agtggtggca aacccgaca ggactataaa gataccaggc gtttccccct ggcggctccc       960
tcgtgcgctc tcctgttcct gcctttcggt ttaccggtgt cattccgctg ttatggccgc     1020
gtttgtctca ttccacgcct gacactcagt tccgggtagg cagttcgctc caagctggac     1080
tgtatgcacg aaccccccgt tcagtccgac cgctgcgcct tatccggtaa ctatcgtctt     1140
gagtccaacc cggaaagaca tgcaaaagca ccactggcag cagccactgg taattgattt     1200
agaggagtta gtcttgaagt catgcgccgg ttaaggctaa actgaaagga caagttttgg     1260
tgactgcgct cctccaagcc agttacctcg gttcaaagag ttggtagctc agagaacctt     1320
cgaaaaaccg ccctgcaagg cggttttttc gttttcagag caagagatta gcgcagacc      1380 aaaacgatct caagaagatc atcttattaa tcagataaaa tatttctaga tttcagtgca     1440
atttatctct tcaaatgtag cacctgaagt cagccccata cgatataagt tgtaattctc     1500
atgtttgaca gcttatcatc gataagcttc gactgcacgg tgcaccaatg cttctggcgt     1560
caggcagcca tcggaagctg tggtatggct gtgcaggtcg taaatcactg cataattcgt     1620
gtcgctcaag gcgcactccc gttctggata atgttttttg cgccgacatc ataacggttc     1680
tggcaaatat tctgaaatga ctgttgacaa ttaatcatcg gctcgtat aatgtgtgga       1740 attgtgagcg gataacaatt tcagaattca aagatcttt taagaaggag atatacatat      1800
gaaaaatgtt ggttttatcg gctggcgcgg tatggtcggc tccgttctca tgcaacgcat     1860
ggttgaagag cgcgacttcg acgccattcg ccctgtcttc ttttctactt ctcagcttgg     1920
ccaggctgcg ccgtctttg gcggaaccac tggcacactt caggatgcct ttgatctgga     1980
ggcgctaaag gccctcgata tcattgtgac ctgtcagggc ggcgattata ccaacgaaat     2040
ctatccaaag cttcgtgaaa gcggatggca aggttactgg attgacgcag catcgtctct     2100
gcgcatgaaa gatgacgcca tcatcattct tgaccccgtc aatcaggacg tcattaccga     2160
cggattaaat aatggcatca ggacttttgt tggcggtaac tgtaccgtaa gcctgatgtt     2220
gatgtcgttg ggtggtttat cgccaatga tcttgttgat tgggtgtccg ttgcaaccta     2280
ccaggccgct tccggcggtg gtgcgcgaca tatgcgtgag ttattaaccc agatgggcca     2340
tctgtatggc catgtggcag atgaactcgc gaccccgtcc tctgctattc tcgatatcga     2400
acgcaaagtc acaaccttaa cccgtagcgg tgagctgccg gtggataact ttggcgtgcc     2460
gctggcgggt agcctgattc cgtggatcga caaacagctc gataacggtc agagccgcga     2520
agagtggaaa gggcaggcgg aaaccaacaa gatcctcaac acatcttccg taattccggt     2580
agatggttta tgtgtgcgtg tcgggcatt gcgctgccac agccaggcat tcactattaa     2640
attgaaaaaa gatgtgtcta ttccgaccgt ggaagaactg ctggctgcgc acaatccgtg     2700
ggcgaaagtc gttccgaacg atcgggaaat cactatgcgt gagctaaccc cagctgccgt     2760
taccggcacg ctgaccacgc cggtaggccg cctgcgtaag ctgaatatgg gaccagagtt     2820
```

```
cctgtcagcc tttaccgtgg gcgaccagct gctgtggggg gccgcggagc cgctgcgtcg    2880
gatgcttcgt caactggcgt aatgtcgacc gatgcccttg agagccttca acccagtcag    2940
ctccttccgg tgggcgcggg gcatgactat cgtcgccgca cttatgactg tcttctttat    3000
catgcaactc gtaggacagg tgccggcagc gctctgggtc attttcggcg aggaccgctt    3060
tcgctggagc gcgacgatga tcggcctgtc gcttgcggta ttcggaatct tgcacgccct    3120
cgctcaagcc ttcgtcactg gtcccgccac caaacgtttc ggcgagaagc aggccattat    3180
cgccggcatg gcggccgacg cgctgggcta cgtcttgctg gcgttcgcga cgcgaggctg    3240
gatggccttc cccattatga ttcttctcgc ttccggcggc atcggatgc cgcgttgca    3300 ggccatgctg tccaggcagg tagatgacga ccatcaggga cagcttcaag gatcgctcgc    3360
ggctcttacc agcctaactt cgatcactgg accgctgatc gtcacggcga tttatgccgc    3420
ctcggcgagc acatggaacg ggttggcatg gattgtaggc gccgccctat accttgtctg    3480 cctcccgcg ttgcgtcgcg gtgcatggag ccgggccacc tcgacctgaa tggaagccgg    3540
cggcacctcg ctaacggatt caccactcca agaattggag ccaatcaatt cttgcggaga    3600
actgtgaatg cgcaaaccaa cccttggcag aacatatcca tcgcgtccgc catctccagc    3660
agccgcacgg ggcgcatctc gggcagcgtt gggtcctggc cacgggtgcg catgatcgtg    3720
ctcctgtcgt tgaggacccg gctaggctgg cggggttgcc ttactggtta gcagaatgaa    3780
tcaccgatac gcgagcgaac gtgaagcgac tgctgctgca aaacgtctgc gacctgagca    3840
acaacatgaa tggtcttcgg tttccgtgtt tcgtaaagtc tggaaacgcg gaagtcccct    3900
acgtgctgct gaagttgccc gcaacagaga gtggaaccaa ccggtgatac cacgatacta    3960
tgactgagag tcaacgccat gagcggcctc atttcttatt ctgagttaca acagtccgca    4020
ccgctgtccg gtagctcctt ccggtgggcg cggggcatga ctatcgtcgc cgcacttatg    4080
actgtcttct ttatcatgca actcgtagga caggtgccgg cagcgcccaa cagtcccccg    4140
gccacggggc ctgccaccat acccacgccg aaacaagcgc cctgcaccat tatgttccgg    4200
atctgcatcg caggatgctg ctggctaccc tgtggaacac ctacatctgt attaacgaag    4260
cgctaaccgt ttttatcagg ctctgggagg cagaataaat gatcatatcg tcaattatta    4320
cctccacggg gagagcctga gcaaactggc ctcaggcatt tgagaagcac acggtcacac    4380
tgcttccggt agtcaataaa ccggtaaacc agcaatagac ataagcggct atttaacgac    4440
cctgccctga accgacgacc gggtcgaatt tgctttcgaa tttctgccat tcatccgctt    4500
attatcactt attcaggcgt agcaccaggc gtttaagggc accaataact gccttaaaaa    4560
aattacgccc cgccctgcca ctcatcgcag tactgttgta attcattaag cattctgccg    4620
acatggaagc catcacagac ggcatgatga acctgaatcg ccagcggcat cagcaccttg    4680
tcgccttgcg tataatattt gcccatggtg aaaacggggg cgaagaagtt gtccatattg    4740
gccacgttta aatcaaaact ggtgaaactc acccagggat tggctgagac gaaaaacata    4800
ttctcaataa acccttagg gaataggcc aggttttcac cgtaacacgc cacatcttgc    4860
gaatatatgt gtagaaactg ccggaaatcg tcgtggtatt cactccagag cgatgaaaac    4920
gtttcagttt gctcatggaa aacggtgtaa caagggtgaa cactatccca tatcaccagc    4980
tcaccgtctt tcattgccat acg                                            5003
```

<210> SEQ ID NO 35
<211> LENGTH: 38
<212> TYPE: DNA
<213> ORGANISM: Artificial

<220> FEATURE:
<223> OTHER INFORMATION: pACYC-asd-F
<220> FEATURE:
<221> NAME/KEY: misc_feature
<222> LOCATION: (1)..(38)
<223> OTHER INFORMATION: pACYA-asd-F

<400> SEQUENCE: 35
gaaggagata tacatatgaa aaatgttggt tttatcgg                       38

<210> SEQ ID NO 36
<211> LENGTH: 36
<212> TYPE: DNA
<213> ORGANISM: Artificial
<220> FEATURE:
<223> OTHER INFORMATION: pACYC-asd_R
<220> FEATURE:
<221> NAME/KEY: misc_feature
<222> LOCATION: (1)..(36)
<223> OTHER INFORMATION: pACYA-asd-R

<400> SEQUENCE: 36
aagggcatcg gtcgacatta cgccagttga cgaagc                         36

<210> SEQ ID NO 37
<211> LENGTH: 1344
<212> TYPE: DNA
<213> ORGANISM: E. coli
<220> FEATURE:
<221> NAME/KEY: misc_feature
<222> LOCATION: (1)..(1344)
<223> OTHER INFORMATION: gdhA

<400> SEQUENCE: 37

| | | | | |
|---|---|---|---|---|
| atggatcaga | catattctct | ggagtcattc | ctcaaccatg | tccaaaagcg cgacccgaat | 60 |
| caaaccgagt | tcgcgcaagc | cgttcgtgaa | gtaatgacca | cactctggcc tttctcttgaa | 120 |
| caaaatccaa | aatatcgcca | gatgtcatta | ctggagcgtc | tggttgaacc ggagcgcgtg | 180 |
| atccagtttc | gcgtggtatg | ggttgatgat | cgcaatcagg | tacaggtcaa ccgtgcatgg | 240 |
| cgtgtgcagt | tcagctctgc | catcggcccg | tacaaaggcg | gtatgcgctt ccatccgtca | 300 |
| gttaacctct | ccattctcaa | attcctcggc | ttcgaacaaa | ccttcaaaaa tgccctgact | 360 |
| accctgccga | tgggcggtgg | taaaggcggt | agcgattttg | acccgaaagg taaaagcgaa | 420 |
| ggcgaagtga | tgcgttttct | gccaggcgctg | atgaccgagc | tttatcgtca tctgggcgcg | 480 |
| gataccgacg | ttccggcagg | tgatatcggc | gttggtggtc | gtgaagtcgg ctttatggcg | 540 |
| gggatgatga | aaaagctctc | caacaatacc | gcctgcgtct | tcaccggtaa gggccttttca | 600 |
| tttggcggta | gtcttattcg | cccggaagct | accggctacg | gtctggttta tttcacagaa | 660 |
| gcaatgttaa | aacgccacgg | tatgggtttt | gaagggatgc | gcgtttccgt ttctggctcc | 720 |
| ggcaacgtcg | cccagtacgc | tatcgaaaaa | gcgatggaat | tggtgctcg tgtgatcact | 780 |
| gcgtcagact | ccagcggcac | tgtagttgat | gaaagcggat | tcacgaaaga gaaactggca | 840 |
| cgtcttatcg | aaatcaaagc | cagccgcgat | ggtcgagtgg | cagattacgc caaagaattt | 900 |
| ggtctggtct | atctcgaagg | ccaacagccg | tggtctgtac | cggttgatat cgccctgcct | 960 |
| tgcgccaccc | agaacgaact | ggatgttgac | gccgcgcatc | agcttatcgc caatggcgtt | 1020 |
| aaagccgtcg | ctgaaggggc | aaatatgccg | accaccatcg | aagcgactga actgttccag | 1080 |
| caggcaggcg | tactgtttgc | accgggtaaa | gcggctaatg | ctggcggtgt agcaacgtcg | 1140 |
| ggcctggaaa | tggcacaaaa | cgctgcgcgc | ctgggctgga | aagccgagaa agttgacgca | 1200 |

```
cgtttgcatc acatcatgct ggatatccac catgcctgtg ttgagcatgg tggtgaaggt    1260
gagcaaacca actacgtgca gggcgcgaac attgccggtt ttgtgaaggt tgccgatgcg    1320
atgctggcgc agggtgtgat ttaa                                           1344
```

<210> SEQ ID NO 38
<211> LENGTH: 447
<212> TYPE: PRT
<213> ORGANISM: E. coli
<220> FEATURE:
<221> NAME/KEY: MISC_FEATURE
<222> LOCATION: (1)..(447)
<223> OTHER INFORMATION: gdhA

<400> SEQUENCE: 38

```
Met Asp Gln Thr Tyr Ser Leu Glu Ser Phe Leu Asn His Val Gln Lys
1               5                   10                  15

Arg Asp Pro Asn Gln Thr Glu Phe Ala Gln Ala Val Arg Glu Val Met
            20                  25                  30

Thr Thr Leu Trp Pro Phe Leu Glu Gln Asn Pro Lys Tyr Arg Gln Met
        35                  40                  45

Ser Leu Leu Glu Arg Leu Val Glu Pro Glu Arg Val Ile Gln Phe Arg
    50                  55                  60

Val Val Trp Val Asp Asp Arg Asn Gln Val Gln Val Asn Arg Ala Trp
65                  70                  75                  80

Arg Val Gln Phe Ser Ser Ala Ile Gly Pro Tyr Lys Gly Gly Met Arg
                85                  90                  95

Phe His Pro Ser Val Asn Leu Ser Ile Leu Lys Phe Leu Gly Phe Glu
            100                 105                 110

Gln Thr Phe Lys Asn Ala Leu Thr Thr Leu Pro Met Gly Gly Gly Lys
        115                 120                 125

Gly Gly Ser Asp Phe Asp Pro Lys Gly Lys Ser Glu Gly Glu Val Met
    130                 135                 140

Arg Phe Cys Gln Ala Leu Met Thr Glu Leu Tyr Arg His Leu Gly Ala
145                 150                 155                 160

Asp Thr Asp Val Pro Ala Gly Asp Ile Gly Val Gly Gly Arg Glu Val
                165                 170                 175

Gly Phe Met Ala Gly Met Met Lys Lys Leu Ser Asn Asn Thr Ala Cys
            180                 185                 190

Val Phe Thr Gly Lys Gly Leu Ser Phe Gly Gly Ser Leu Ile Arg Pro
        195                 200                 205

Glu Ala Thr Gly Tyr Gly Leu Val Tyr Phe Thr Glu Ala Met Leu Lys
    210                 215                 220

Arg His Gly Met Gly Phe Glu Gly Met Arg Val Ser Val Ser Gly Ser
225                 230                 235                 240

Gly Asn Val Ala Gln Tyr Ala Ile Glu Lys Ala Met Glu Phe Gly Ala
                245                 250                 255

Arg Val Ile Thr Ala Ser Asp Ser Ser Gly Thr Val Val Asp Glu Ser
            260                 265                 270

Gly Phe Thr Lys Glu Lys Leu Ala Arg Leu Ile Glu Ile Lys Ala Ser
        275                 280                 285

Arg Asp Gly Arg Val Ala Asp Tyr Ala Lys Glu Phe Gly Leu Val Tyr
    290                 295                 300

Leu Glu Gly Gln Gln Pro Trp Ser Val Pro Val Asp Ile Ala Leu Pro
305                 310                 315                 320

Cys Ala Thr Gln Asn Glu Leu Asp Val Asp Ala Ala His Gln Leu Ile
```

|   |   |   | 325 |   |   |   | 330 |   |   |   | 335 |
|---|---|---|---|---|---|---|---|---|---|---|---|

Ala Asn Gly Val Lys Ala Val Ala Glu Gly Ala Asn Met Pro Thr Thr
            340                 345                 350

Ile Glu Ala Thr Glu Leu Phe Gln Gln Ala Gly Val Leu Phe Ala Pro
            355                 360                 365

Gly Lys Ala Ala Asn Ala Gly Gly Val Ala Thr Ser Gly Leu Glu Met
            370                 375                 380

Ala Gln Asn Ala Ala Arg Leu Gly Trp Lys Ala Glu Lys Val Asp Ala
385                 390                 395                 400

Arg Leu His His Ile Met Leu Asp Ile His His Ala Cys Val Glu His
                405                 410                 415

Gly Gly Glu Gly Glu Gln Thr Asn Tyr Val Gln Gly Ala Asn Ile Ala
                420                 425                 430

Gly Phe Val Lys Val Ala Asp Ala Met Leu Ala Gln Gly Val Ile
            435                 440                 445

<210> SEQ ID NO 39
<211> LENGTH: 5242
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(5242)
<223> OTHER INFORMATION: pACYC-gdhA plasmid

<400> SEQUENCE: 39

| | |
|---|---|
| gaattccgga tgagcattca tcaggcgggc aagaatgtga ataaaggccg gataaaactt | 60 |
| gtgcttattt ttctttacgg tctttaaaaa ggccgtaata tccagctgaa cggtctggtt | 120 |
| ataggtacat tgagcaactg actgaaatgc ctcaaaatgt tctttacgat gccattggga | 180 |
| tatatcaacg gtggtatatc cagtgatttt tttctccatt ttagcttcct tagctcctga | 240 |
| aaatctcgat aactcaaaaa atacgcccgg tagtgatctt atttcattat ggtgaaagtt | 300 |
| ggaacctctt acgtgccgat caacgtctca ttttcgccaa aagttggccc agggcttccc | 360 |
| ggtatcaaca gggacaccag gatttattta ttctgcgaag tgatcttccg tcacaggtat | 420 |
| ttattcggcg caaagtgcgt cgggtgatgc tgccaactta ctgatttagt gtatgatggt | 480 |
| gtttttgagg tgctccagtg gcttctgttt ctatcagctg tccctcctgt tcagctactg | 540 |
| acggggtggt gcgtaacggc aaaagcaccg ccggacatca gcgctagcgg agtgtatact | 600 |
| ggcttactat gttggcactg atgagggtgt cagtgaagtg cttcatgtgg caggagaaaa | 660 |
| aaggctgcac cggtgcgtca gcagaatatg tgatacagga tatattccgc ttcctcgctc | 720 |
| actgactcgc tacgctcggt cgttcgactg cggcgagcgg aaatggctta cgaacggggc | 780 |
| ggagatttcc tggaagatgc caggaagata cttaacaggg aagtgagagg gccgcggcaa | 840 |
| agccgttttt ccataggctc cgcccccctg acaagcatca cgaaatctga cgctcaaatc | 900 |
| agtggtggcg aaacccgaca ggactataaa gataccaggc gtttccccct ggcggctccc | 960 |
| tcgtgcgctc tcctgttcct gcctttcggt ttaccggtgt cattccgctg ttatggccgc | 1020 |
| gtttgtctca ttccacgcct gacactcagt tccgggtagg cagttcgctc caagctggac | 1080 |
| tgtatgcacg aaccccccgt tcagtccgac cgctgcgcct tatccggtaa ctatcgtctt | 1140 |
| gagtccaacc cggaaagaca tgcaaaagca ccactggcag cagccactgg taattgattt | 1200 |
| agaggagtta gtcttgaagt catgcgccgg ttaaggctaa actgaaagga caagttttgg | 1260 |

-continued

```
tgactgcgct cctccaagcc agttacctcg gttcaaagag ttggtagctc agagaacctt    1320
cgaaaaaccg ccctgcaagg cggttttttc gttttcagag caagagatta cgcgcagacc    1380
aaaacgatct caagaagatc atcttattaa tcagataaaa tatttctaga tttcagtgca    1440
atttatctct tcaaatgtag cacctgaagt cagccccata cgatataagt tgtaattctc    1500
atgtttgaca gcttatcatc gataagcttc gactgcacgg tgcaccaatg cttctggcgt    1560
caggcagcca tcgaagctg tggtatggct gtgcaggtcg taaatcactg cataattcgt     1620
gtcgctcaag gcgcactccc gttctggata atgttttttg cgccgacatc ataacggttc    1680
tggcaaatat tctgaaatga gctgttgaca attaatcatc cggctcgtat aatgtgtgga    1740
attgtgagcg gataacaatt tcagaattca aagatctttt aagaaggag atatacatat     1800 ggatcagaca tattctctgg agtcattcct caaccatgtc caaaagcgcg acccgaatca    1860
aaccgagttc gcgcaagccg ttcgtgaagt aatgaccaca ctctggcctt tcttgaaca    1920 aaatccaaaa tatcgccaga tgtcattact ggagcgtctg gttgaaccgg agcgcgtgat    1980
ccagtttcgc gtggtatggg ttgatgatcg caatcaggta caggtcaacc gtgcatggcg    2040
tgtgcagttc agctctgcca tcggcccgta caaaggcggt atgcgcttcc atccgtcagt    2100
taacctctcc attctcaaat tcctcggctt cgaacaaacc ttcaaaaatg ccctgactac    2160
cctgccgatg ggcggtggta aaggcggtag cgattttgac ccgaaaggta aaagcgaagg    2220
cgaagtgatg cgtttctgcc aggcgctgat gaccgagctt tatcgtcatc tgggcgcgga    2280
taccgacgtt ccggcaggtg atatcggcgt tggtggtcgt gaagtcggct ttatggcggg    2340
gatgatgaaa aagctctcca acaataccgc ctgcgtcttc accggtaagg cctttcatt     2400 tggcggtagt cttattcgcc cggaagctac cggctacggt ctggtttatt tcacagaagc    2460
aatgttaaaa cgccacgta tgggttttga agggatgcgc gtttccgttt ctggctccgg    2520
caacgtcgcc cagtacgcta tcgaaaaagc gatggaattt ggtgctcgtg tgatcactgc    2580
gtcagactcc agcggcactg tagttgatga agcggattc acgaaagaga aactggcacg     2640
tcttatcgaa atcaaagcca gccgcgatgg tcgagtggca gattacgcca agaatttgg     2700 tctggtctat ctcgaaggcc aacagccgtg gtctgtaccg gttgatatcg ccctgccttg    2760
cgccacccag aacgaactgg atgttgacgc cgcgcatcag cttatcgcca atggcgttaa    2820
agccgtcgct gaaggggcaa atatgccgac caccatcgaa gcgactgaac tgttccagca    2880
ggcaggcgta ctgtttgcac cgggtaaagc ggctaatgct ggcggtgtag caacgtcggg    2940
cctggaaatg gcacaaaacg ctgcgcgcct gggctggaaa gccagaaaag ttgacgcacg    3000
tttgcatcac atcatgctgg atatccacca tgcctgtgtt gagcatggtg gtgaaggtga    3060
gcaaaccaac tacgtgcagg gcgcgaacat tgccggtttt tgtgaaggttg ccgatgcgat    3120 gctggcgcag ggtgtgattt aagtcgaccg atgcccttga gagccttcaa cccagtcagc    3180
tccttccggt gggcgcgggg catgactatc gtcgccgcac ttatgactgt cttctttatc    3240
atgcaactcg taggacaggt gccggcagcg ctctgggtca ttttcggcga ggaccgcttt    3300
cgctggagcg cgacgatgat cggcctgtcg cttgcggtat tcggaatctt gcacgccctc    3360
gctcaagcct tcgtcactgg tcccgccacc aaacgtttcg gcgagaagca ggccattatc    3420
gccggcatgg cggccgacgc gctgggctac gtcttgctgg cgttcgcgac gcgaggctgg    3480
atggccttcc ccattatgat tcttctcgct tccggcggca tcgggatgcc cgcgttgcag    3540
gccatgctgt ccaggcaggt agatgacgac catcaggac agcttcaagg atcgctcgcg    3600
gctcttacca gcctaacttc gatcactgga ccgctgatcg tcacggcgat ttatgccgcc    3660
```

-continued

| | |
|---|---|
| tcggcgagca catggaacgg gttggcatgg attgtaggcg ccgccctata ccttgtctgc | 3720 |
| ctccccgcgt tgcgtcgcgg tgcatggagc cgggccacct cgacctgaat ggaagccggc | 3780 |
| ggcacctcgc taacggattc accactccaa gaattggagc caatcaattc ttgcggagaa | 3840 |
| ctgtgaatgc gcaaaccaac ccttggcaga acatatccat cgcgtccgcc atctccagca | 3900 |
| gccgcacgcg gcgcatctcg ggcagcgttg gtcctggcc acgggtgcgc atgatcgtgc | 3960 |
| tcctgtcgtt gaggacccgg ctaggctggc ggggttgcct tactggttag cagaatgaat | 4020 |
| caccgatacg cgagcgaacg tgaagcgact gctgctgcaa aacgtctgcg acctgagcaa | 4080 |
| caacatgaat ggtcttcggt ttccgtgttt cgtaaagtct ggaaacgcgg aagtccccta | 4140 |
| cgtgctgctg aagttgcccg caacagagag tggaaccaac cggtgatacc acgatactat | 4200 |
| gactgagagt caacgccatg agcggcctca tttcttattc tgagttacaa cagtccgcac | 4260 |
| cgctgtccgg tagctccttc cggtgggcgc ggggcatgac tatcgtcgcc gcacttatga | 4320 |
| ctgtcttctt tatcatgcaa ctcgtaggac aggtgccggc agcgcccaac agtccccgg | 4380 |
| ccacggggcc tgccaccata cccacgccga aacaagcgcc ctgcaccatt atgttccgga | 4440 |
| tctgcatcgc aggatgctgc tggctaccct gtggaacacc tacatctgta ttaacgaagc | 4500 |
| gctaaccgtt tttatcaggc tctgggaggc agaataaatg atcatatcgt caattattac | 4560 |
| ctccacgggg agagcctgag caaactggcc tcaggcattt gagaagcaca cggtcacact | 4620 |
| gcttccggta gtcaataaac cggtaaacca gcaatagaca taagcggcta tttaacgacc | 4680 |
| ctgccctgaa ccgacgaccg ggtcgaattt gctttcgaat ttctgccatt catccgctta | 4740 |
| ttatcactta ttcaggcgta gcaccaggcg tttaagggca ccaataactg ccttaaaaaa | 4800 |
| attacgcccc gccctgccac tcatcgcagt actgttgtaa ttcattaagc attctgccga | 4860 |
| catggaagcc atcacagacg gcatgatgaa cctgaatcgc cagcggcatc agcaccttgt | 4920 |
| cgccttgcgt ataatatttg cccatggtga aacggggggc gaagaagttg tccatattgg | 4980 |
| ccacgtttaa atcaaaactg gtgaaactca cccagggatt ggctgagacg aaaaacatat | 5040 |
| tctcaataaa cccctttaggg aaataggcca ggttttcacc gtaacacgcc acatcttgcg | 5100 |
| aatatatgtg tagaaactgc cggaaatcgt cgtggtattc actccagagc gatgaaaacg | 5160 |
| tttcagtttg ctcatggaaa acggtgtaac aagggtgaac actatcccat atcaccagct | 5220 |
| caccgtcttt cattgccata cg | 5242 |

<210> SEQ ID NO 40
<211> LENGTH: 40
<212> TYPE: DNA
<213> ORGANISM: Artificial
<220> FEATURE:
<223> OTHER INFORMATION: Synthetic DNA
<220> FEATURE:
<221> NAME/KEY: misc_feature
<222> LOCATION: (1)..(40)
<223> OTHER INFORMATION: Primer pACYC-gdhA-F

<400> SEQUENCE: 40
gaaggagata tacatatgga tcagacatat tctctggagt                                40

<210> SEQ ID NO 41
<211> LENGTH: 35
<212> TYPE: DNA
<213> ORGANISM: Artificial
<220> FEATURE:
<223> OTHER INFORMATION: Synthetic DNA
<220> FEATURE:

```
<221> NAME/KEY: misc_feature
<222> LOCATION: (1)..(35)
<223> OTHER INFORMATION: Primer pACYC-gdhA-R

<400> SEQUENCE: 41
aagggcatcg gtcgacttaa atcacaccct gcgcc                                35
```